United States Patent
Shelton, IV et al.

(10) Patent No.: US 7,472,815 B2
(45) Date of Patent: Jan. 6, 2009

(54) SURGICAL STAPLING INSTRUMENTS WITH COLLAPSIBLE FEATURES FOR CONTROLLING STAPLE HEIGHT

(75) Inventors: Frederick E. Shelton, IV, New Vienna, OH (US); Jeffrey S. Swayze, Hamilton, OH (US); Leslie M. Fugikawa, Cincinnati, OH (US); Eugene L. Timperman, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 84 days.

(21) Appl. No.: 11/540,734

(22) Filed: Sep. 29, 2006

(65) Prior Publication Data
US 2007/0073340 A1  Mar. 29, 2007

Related U.S. Application Data

(63) Continuation-in-part of application No. 11/231,456, filed on Sep. 21, 2005.

(51) Int. Cl.
*B25C 1/04* (2006.01)
(52) U.S. Cl. ............................. 227/176.1; 227/19
(58) Field of Classification Search ............ 227/19, 227/175.1, 176.1, 177.1, 178.1, 179
See application file for complete search history.

(56) References Cited

U.S. PATENT DOCUMENTS

| | | | |
|---|---|---|---|
| 2,037,727 A | 4/1936 | Chapelle | |
| 3,269,630 A | 8/1966 | Fleischer | |
| 3,551,987 A | 1/1971 | Wilkinson | |
| 3,643,851 A | 2/1972 | Green et al. | |
| 3,662,939 A | 5/1972 | Bryan | |
| 3,717,294 A | 2/1973 | Green | |
| 3,734,207 A | 5/1973 | Fishbein | |
| 3,819,100 A | 6/1974 | Noiles et al. | |
| 3,894,174 A | 7/1975 | Cartun | |
| 3,940,844 A | 3/1976 | Colby et al. | |
| 4,317,451 A | 3/1982 | Cerwin et al. | |

(Continued)

FOREIGN PATENT DOCUMENTS

CA   2458946 A1   3/2003

(Continued)

OTHER PUBLICATIONS

U.S. Appl. No. 11/475,412, filed Jun. 27, 2006.

(Continued)

*Primary Examiner*—Brian D Nash

(57) ABSTRACT

A surgical instrument for being endoscopically or laparoscopically inserted into a surgical site for simultaneous stapling and severing of tissue includes force adjusted spacing between an upper jaw (anvil) and a lower jaw (staple cartridge engaged to an elongate staple channel) so that the height of staple formation corresponds to the thickness of the tissue, yet does not exceed the height range that may be accommodated by the length of the staples. In particular, collapsible staple drivers may be supported within the cartridge for driving a staple or staples supported thereon into forming contact with an underside of an anvil attached to the instrument. As the staples contact the anvil, the drivers can compress or collapse to control the overall formed height of the staple or staples based upon the amount of compression forces experienced by the drivers during the stapling process.

22 Claims, 34 Drawing Sheets

U.S. PATENT DOCUMENTS

| | | | |
|---|---|---|---|
| 4,321,002 A * | 3/1982 | Froehlich | 411/457 |
| 4,331,277 A | 5/1982 | Green | |
| 4,379,457 A | 4/1983 | Gravener et al. | |
| 4,380,312 A * | 4/1983 | Landrus | 227/116 |
| 4,383,634 A | 5/1983 | Green | |
| 4,396,139 A * | 8/1983 | Hall et al. | 227/19 |
| 4,402,445 A | 9/1983 | Green | |
| 4,428,376 A | 1/1984 | Mericle | |
| 4,442,964 A * | 4/1984 | Becht | 227/8 |
| 4,485,816 A | 12/1984 | Krumme | |
| 4,500,024 A | 2/1985 | DiGiovanni et al. | |
| 4,520,817 A | 6/1985 | Green | |
| 4,522,327 A | 6/1985 | Korthoff et al. | |
| 4,526,174 A | 7/1985 | Froehlich | |
| 4,530,453 A | 7/1985 | Green | |
| 4,548,202 A | 10/1985 | Duncan | |
| 4,566,620 A | 1/1986 | Green et al. | |
| 4,573,622 A | 3/1986 | Green et al. | |
| 4,580,712 A | 4/1986 | Green | |
| 4,589,416 A | 5/1986 | Green | |
| 4,605,001 A * | 8/1986 | Rothfuss et al. | 227/178.1 |
| 4,606,343 A | 8/1986 | Conta et al. | |
| 4,608,981 A | 9/1986 | Rothfuss et al. | |
| 4,610,383 A | 9/1986 | Rothfuss et al. | |
| 4,629,107 A | 12/1986 | Fedotov et al. | |
| 4,633,874 A | 1/1987 | Chow et al. | |
| 4,671,445 A | 6/1987 | Barker et al. | |
| 4,709,120 A | 11/1987 | Pearson | |
| 4,715,520 A | 12/1987 | Roehr, Jr. et al. | |
| 4,719,917 A | 1/1988 | Barrows et al. | |
| 4,728,020 A | 3/1988 | Green et al. | |
| 4,741,336 A | 5/1988 | Failla et al. | |
| 4,754,909 A | 7/1988 | Barker et al. | |
| 4,767,044 A | 8/1988 | Green | |
| 4,805,617 A | 2/1989 | Bedi et al. | |
| 4,821,939 A * | 4/1989 | Green | 227/19 |
| 4,869,414 A | 9/1989 | Green et al. | |
| 4,869,415 A | 9/1989 | Fox | |
| 4,892,244 A | 1/1990 | Fox et al. | |
| 4,915,100 A | 4/1990 | Green | |
| 4,941,623 A | 7/1990 | Pruitt | |
| 4,944,443 A | 7/1990 | Oddsen et al. | |
| 4,955,959 A | 9/1990 | Tompkins et al. | |
| 4,978,049 A | 12/1990 | Green | |
| 5,009,661 A | 4/1991 | Michelson | |
| 5,027,834 A | 7/1991 | Pruitt | |
| 5,031,814 A | 7/1991 | Tompkins et al. | |
| 5,040,715 A | 8/1991 | Green et al. | |
| 5,062,563 A * | 11/1991 | Green et al. | 227/175.3 |
| 5,065,929 A | 11/1991 | Schulze et al. | |
| 5,071,430 A | 12/1991 | de Salis et al. | |
| 5,080,556 A | 1/1992 | Carreno | |
| 5,104,025 A | 4/1992 | Main et al. | |
| 5,106,008 A | 4/1992 | Tompkins et al. | |
| 5,111,987 A | 5/1992 | Moeinzadeh et al. | |
| 5,129,570 A | 7/1992 | Schulze et al. | |
| 5,137,198 A | 8/1992 | Nobis et al. | |
| 5,156,315 A | 10/1992 | Green et al. | |
| 5,158,567 A * | 10/1992 | Green | 606/219 |
| 5,200,280 A | 4/1993 | Karasa | |
| 5,207,697 A | 5/1993 | Carusillo et al. | |
| 5,211,649 A | 5/1993 | Kohler et al. | |
| 5,219,111 A | 6/1993 | Bilotti et al. | |
| 5,221,036 A | 6/1993 | Takase | |
| 5,242,457 A | 9/1993 | Akopov et al. | |
| 5,246,156 A | 9/1993 | Rothfuss et al. | |
| 5,253,793 A | 10/1993 | Green et al. | |
| 5,258,009 A | 11/1993 | Conners | |
| 5,271,544 A | 12/1993 | Fox et al. | |
| RE34,519 E | 1/1994 | Fox et al. | |
| 5,275,323 A | 1/1994 | Schulze et al. | |
| 5,282,806 A | 2/1994 | Haber et al. | |
| 5,282,829 A | 2/1994 | Hermes | |
| 5,304,204 A | 4/1994 | Bregen | |
| 5,307,976 A | 5/1994 | Olson et al. | |
| 5,309,927 A | 5/1994 | Welch | |
| 5,318,221 A | 6/1994 | Green et al. | |
| 5,332,142 A | 7/1994 | Robinson et al. | |
| 5,342,395 A | 8/1994 | Jarrett et al. | |
| 5,342,396 A | 8/1994 | Cook | |
| 5,344,060 A | 9/1994 | Gravener et al. | |
| 5,350,400 A | 9/1994 | Esposito et al. | |
| 5,366,134 A | 11/1994 | Green et al. | |
| 5,366,479 A | 11/1994 | McGarry et al. | |
| 5,379,933 A | 1/1995 | Green et al. | |
| 5,383,880 A | 1/1995 | Hooven | |
| 5,389,098 A | 2/1995 | Tsuruta et al. | |
| 5,395,033 A | 3/1995 | Byrne et al. | |
| 5,397,046 A | 3/1995 | Savage et al. | |
| 5,403,312 A | 4/1995 | Yates et al. | |
| 5,413,267 A | 5/1995 | Solyntjes et al. | |
| 5,413,268 A | 5/1995 | Green et al. | |
| 5,415,335 A | 5/1995 | Knodell, Jr. | |
| 5,425,745 A | 6/1995 | Green et al. | |
| 5,431,322 A | 7/1995 | Green et al. | |
| 5,433,721 A | 7/1995 | Hooven et al. | |
| 5,441,193 A | 8/1995 | Gravener | |
| 5,445,304 A | 8/1995 | Plyley et al. | |
| 5,456,401 A | 10/1995 | Green et al. | |
| 5,462,215 A | 10/1995 | Viola et al. | |
| 5,465,895 A | 11/1995 | Knodel et al. | |
| 5,465,896 A | 11/1995 | Allen et al. | |
| 5,470,006 A | 11/1995 | Rodak | |
| 5,472,132 A | 12/1995 | Savage et al. | |
| 5,474,566 A | 12/1995 | Alesi et al. | |
| 5,480,089 A | 1/1996 | Blewett | |
| 5,482,197 A | 1/1996 | Green et al. | |
| 5,484,095 A | 1/1996 | Green et al. | |
| 5,484,451 A | 1/1996 | Akopov et al. | |
| 5,485,947 A | 1/1996 | Olson et al. | |
| 5,485,952 A | 1/1996 | Fontayne | |
| 5,487,499 A | 1/1996 | Sorrentino et al. | |
| 5,487,500 A | 1/1996 | Knodel et al. | |
| 5,489,058 A | 2/1996 | Plyley et al. | |
| 5,497,933 A | 3/1996 | DeFonzo et al. | |
| 5,503,320 A | 4/1996 | Webster et al. | |
| 5,503,635 A | 4/1996 | Sauer et al. | |
| 5,503,638 A | 4/1996 | Cooper et al. | |
| 5,509,596 A | 4/1996 | Green et al. | |
| 5,518,163 A | 5/1996 | Hooven | |
| 5,518,164 A | 5/1996 | Hooven | |
| 5,522,817 A | 6/1996 | Sander et al. | |
| 5,529,235 A | 6/1996 | Boiarski et al. | |
| 5,535,934 A | 7/1996 | Boiarski et al. | |
| 5,535,935 A | 7/1996 | Vidal et al. | |
| 5,535,937 A | 7/1996 | Boiarski et al. | |
| 5,540,375 A | 7/1996 | Bolanos et al. | |
| 5,547,117 A | 8/1996 | Hamblin et al. | |
| 5,549,628 A | 8/1996 | Cooper et al. | |
| 5,553,675 A | 9/1996 | Pitzen et al. | |
| 5,554,169 A | 9/1996 | Green et al. | |
| 5,560,532 A | 10/1996 | DeFonzo et al. | |
| 5,562,239 A | 10/1996 | Boiarski et al. | |
| 5,562,241 A | 10/1996 | Knodel et al. | |
| 5,562,682 A | 10/1996 | Oberlin et al. | |
| 5,564,615 A | 10/1996 | Bishop et al. | |
| 5,571,090 A | 11/1996 | Sherts | |
| 5,573,543 A | 11/1996 | Akopov et al. | |
| 5,574,431 A | 11/1996 | McKeown et al. | |
| 5,575,799 A | 11/1996 | Bolanos et al. | |
| 5,575,803 A | 11/1996 | Cooper et al. | |
| 5,577,654 A | 11/1996 | Bishop | |
| 5,580,067 A | 12/1996 | Hamblin et al. | |
| 5,582,611 A | 12/1996 | Tsuruta et al. | |

| | | | | | | |
|---|---|---|---|---|---|---|
| 5,584,425 | A | 12/1996 | Savage et al. | 5,782,396 | A | 7/1998 | Mastri et al. |
| 5,586,711 | A | 12/1996 | Plyley et al. | 5,782,397 | A | 7/1998 | Koukline |
| 5,588,579 | A | 12/1996 | Schnut et al. | 5,785,232 | A | 7/1998 | Vidal et al. |
| 5,588,580 | A | 12/1996 | Paul et al. | 5,794,834 | A | 8/1998 | Hamblin et al. |
| 5,588,581 | A | 12/1996 | Conlon et al. | 5,796,188 | A | 8/1998 | Bays |
| 5,597,107 | A | 1/1997 | Knodel et al. | 5,797,536 | A * | 8/1998 | Smith et al. ............... 227/175.1 |
| 5,601,224 | A | 2/1997 | Bishop et al. | 5,797,537 | A | 8/1998 | Oberlin et al. |
| 5,603,443 | A | 2/1997 | Clark et al. | 5,797,538 | A | 8/1998 | Heaton et al. |
| 5,605,272 | A | 2/1997 | Witt et al. | 5,807,393 | A | 9/1998 | Williamson, IV et al. |
| 5,605,273 | A | 2/1997 | Hamblin et al. | 5,817,093 | A | 10/1998 | Williamson, IV et al. |
| 5,607,094 | A | 3/1997 | Clark et al. | 5,820,009 | A | 10/1998 | Melling et al. |
| 5,607,095 | A * | 3/1997 | Smith et al. ............... 227/177.1 | 5,823,066 | A | 10/1998 | Huitema et al. |
| 5,624,452 | A | 4/1997 | Yates | 5,826,776 | A | 10/1998 | Schulze et al. |
| 5,628,446 | A | 5/1997 | Geiste et al. | 5,829,662 | A * | 11/1998 | Allen et al. ............... 227/177.1 |
| 5,630,539 | A | 5/1997 | Plyley et al. | 5,833,690 | A | 11/1998 | Yates et al. |
| 5,630,540 | A | 5/1997 | Blewett | 5,836,503 | A | 11/1998 | Ehrenfels et al. |
| 5,632,432 | A | 5/1997 | Schulze et al. | 5,839,639 | A | 11/1998 | Sauer et al. |
| 5,634,584 | A | 6/1997 | Okorocha et al. | 5,843,132 | A | 12/1998 | Ilvento |
| 5,636,779 | A | 6/1997 | Palmer | 5,846,254 | A * | 12/1998 | Schulze et al. ............... 606/148 |
| 5,636,780 | A | 6/1997 | Green et al. | 5,855,311 | A | 1/1999 | Hamblin et al. |
| 5,639,008 | A | 6/1997 | Gallagher et al. | 5,865,361 | A | 2/1999 | Milliman et al. |
| 5,645,209 | A | 7/1997 | Green et al. | 5,871,135 | A | 2/1999 | Williamson, IV et al. |
| 5,647,526 | A | 7/1997 | Green et al. | 5,878,937 | A | 3/1999 | Green et al. |
| 5,649,937 | A * | 7/1997 | Bito et al. ................... 606/139 | 5,878,938 | A | 3/1999 | Bittner et al. |
| 5,651,491 | A | 7/1997 | Heaton et al. | 5,891,160 | A | 4/1999 | Williamson, IV et al. |
| 5,653,373 | A | 8/1997 | Green et al. | 5,893,506 | A | 4/1999 | Powell |
| 5,653,374 | A | 8/1997 | Young et al. | 5,894,979 | A | 4/1999 | Powell |
| 5,653,721 | A | 8/1997 | Knodel et al. | 5,897,562 | A | 4/1999 | Bolanos et al. |
| 5,655,698 | A | 8/1997 | Yoon | 5,901,895 | A | 5/1999 | Heaton et al. |
| 5,657,921 | A | 8/1997 | Young et al. | 5,906,625 | A * | 5/1999 | Bito et al. ................... 606/142 |
| 5,658,300 | A | 8/1997 | Bito et al. | 5,911,353 | A | 6/1999 | Bolanos et al. |
| 5,662,258 | A | 9/1997 | Knodel et al. | 5,915,616 | A | 6/1999 | Viola et al. |
| 5,662,260 | A | 9/1997 | Yoon | 5,918,791 | A | 7/1999 | Sorrentino et al. |
| 5,662,662 | A | 9/1997 | Bishop et al. | 5,941,442 | A | 8/1999 | Geiste et al. |
| 5,667,517 | A | 9/1997 | Hooven | 5,954,259 | A | 9/1999 | Viola et al. |
| 5,667,527 | A | 9/1997 | Cook | 5,988,479 | A | 11/1999 | Palmer |
| 5,669,544 | A | 9/1997 | Schulze et al. | 6,010,054 | A | 1/2000 | Johnson et al. |
| 5,673,840 | A | 10/1997 | Schulze et al. | 6,017,356 | A | 1/2000 | Frederick et al. |
| 5,673,841 | A | 10/1997 | Schulze et al. | 6,022,352 | A | 2/2000 | Vandewalle |
| 5,673,842 | A | 10/1997 | Bittner et al. | 6,024,741 | A | 2/2000 | Williamson, IV et al. |
| 5,678,748 | A | 10/1997 | Plyley et al. | 6,024,748 | A | 2/2000 | Manzo et al. |
| 5,680,981 | A | 10/1997 | Mililli et al. | 6,032,849 | A | 3/2000 | Mastri et al. |
| 5,680,982 | A | 10/1997 | Schulze et al. | 6,079,606 | A | 6/2000 | Milliman et al. |
| 5,680,983 | A | 10/1997 | Plyley et al. | 6,083,234 | A | 7/2000 | Nicholas et al. |
| 5,688,270 | A | 11/1997 | Yates et al. | 6,086,600 | A | 7/2000 | Kortenbach |
| 5,690,269 | A | 11/1997 | Bolanos et al. | 6,102,271 | A | 8/2000 | Longo et al. |
| 5,692,668 | A | 12/1997 | Schulze et al. | 6,109,500 | A | 8/2000 | Alli et al. |
| 5,693,042 | A | 12/1997 | Boiarski et al. | H1904 | H | 10/2000 | Yates et al. |
| 5,697,543 | A | 12/1997 | Burdorff | 6,126,670 | A | 10/2000 | Walker et al. |
| 5,697,943 | A | 12/1997 | Sauer et al. | 6,131,789 | A | 10/2000 | Schulze et al. |
| 5,702,408 | A | 12/1997 | Wales et al. | 6,155,473 | A | 12/2000 | Tompkins et al. |
| 5,704,534 | A | 1/1998 | Huitema et al. | 6,156,056 | A | 12/2000 | Kearns et al. |
| 5,706,997 | A | 1/1998 | Green et al. | 6,171,316 | B1 | 1/2001 | Kovac et al. |
| 5,706,998 | A | 1/1998 | Plyley et al. | 6,171,330 | B1 | 1/2001 | Benchetrit |
| 5,709,680 | A | 1/1998 | Yates et al. | 6,202,914 | B1 | 3/2001 | Geiste et al. |
| 5,711,472 | A | 1/1998 | Bryan | 6,223,835 | B1 | 5/2001 | Habedank et al. |
| 5,713,505 | A | 2/1998 | Huitema | 6,241,139 | B1 | 6/2001 | Milliman et al. |
| 5,715,988 | A | 2/1998 | Palmer | 6,250,532 | B1 | 6/2001 | Green et al. |
| 5,716,366 | A | 2/1998 | Yates | 6,264,086 | B1 | 7/2001 | McGuckin, Jr. |
| 5,718,359 | A | 2/1998 | Palmer et al. | 6,264,087 | B1 | 7/2001 | Whitman |
| 5,725,536 | A | 3/1998 | Oberlin et al. | 6,273,897 | B1 | 8/2001 | Dalessandro et al. |
| 5,732,871 | A | 3/1998 | Clark et al. | 6,315,184 | B1 | 11/2001 | Whitman |
| 5,735,445 | A | 4/1998 | Vidal et al. | 6,320,123 | B1 | 11/2001 | Reimers |
| 5,738,474 | A | 4/1998 | Blewett | 6,325,810 | B1 | 12/2001 | Hamilton et al. |
| 5,743,456 | A | 4/1998 | Jones et al. | 6,330,965 | B1 | 12/2001 | Milliman et al. |
| 5,747,953 | A | 5/1998 | Philipp | 6,358,224 | B1 | 3/2002 | Tims et al. |
| 5,752,644 | A | 5/1998 | Bolanos et al. | 6,387,113 | B1 | 5/2002 | Hawkins et al. |
| 5,752,965 | A | 5/1998 | Francis et al. | 6,398,797 | B2 | 6/2002 | Bombard et al. |
| 5,758,814 | A | 6/1998 | Gallagher et al. | 6,416,486 | B1 | 7/2002 | Wampler |
| 5,762,255 | A | 6/1998 | Chrisman et al. | RE37,814 | E | 8/2002 | Allgeyer |
| 5,762,256 | A | 6/1998 | Mastri et al. | 6,440,146 | B2 | 8/2002 | Nicholas et al. |
| 5,779,130 | A | 7/1998 | Alesi et al. | 6,443,973 | B1 | 9/2002 | Whitman |
| 5,779,132 | A | 7/1998 | Knodel et al. | 6,488,197 | B1 | 12/2002 | Whitman |

| | | | | | | |
|---|---|---|---|---|---|---|
| 6,491,201 B1 | 12/2002 | Whitman | | 7,111,769 B2 | 9/2006 | Wales et al. |
| 6,503,257 B2 | 1/2003 | Grant et al. | | 7,114,642 B2 | 10/2006 | Whitman |
| 6,505,768 B2 | 1/2003 | Whitman | | 7,118,582 B1 | 10/2006 | Wang et al. |
| 6,522,101 B2 | 2/2003 | Malackowski | | 7,128,253 B2 | 10/2006 | Mastri et al. |
| 6,592,597 B2 | 7/2003 | Grant et al. | | 7,128,254 B2 | 10/2006 | Shelton, IV et al. |
| 6,602,252 B2 | 8/2003 | Mollenauer | | 7,140,527 B2 | 11/2006 | Ehrenfels et al. |
| 6,616,686 B2 | 9/2003 | Coleman et al. | | 7,143,924 B2 | 12/2006 | Scirica et al. |
| 6,619,529 B2 | 9/2003 | Green et al. | | 7,143,925 B2 | 12/2006 | Shelton, IV et al. |
| 6,620,166 B1 | 9/2003 | Wenstrom, Jr. et al. | | 7,143,926 B2 | 12/2006 | Shelton, IV et al. |
| 6,629,988 B2 | 10/2003 | Weadock | | 7,159,750 B2 | 1/2007 | Racenet et al. |
| 6,644,532 B2 | 11/2003 | Green et al. | | 7,168,604 B2 | 1/2007 | Milliman et al. |
| 6,656,193 B2 | 12/2003 | Grant et al. | | 7,188,758 B2 | 3/2007 | Viola et al. |
| 6,669,073 B2 | 12/2003 | Milliman et al. | | 7,207,471 B2 | 4/2007 | Heinrich et al. |
| 6,681,978 B2 | 1/2004 | Geiste et al. | | 7,207,472 B2 | 4/2007 | Wukusick et al. |
| 6,681,979 B2 | 1/2004 | Whitman | | 7,210,609 B2 | 5/2007 | Leiboff et al. |
| 6,695,199 B2 | 2/2004 | Whitman | | 7,225,964 B2 | 6/2007 | Mastri et al. |
| 6,698,643 B2 | 3/2004 | Whitman | | 7,246,734 B2 | 7/2007 | Shelton, IV |
| 6,716,233 B1 | 4/2004 | Whitman | | 7,258,262 B2 | 8/2007 | Mastri et al. |
| 6,755,338 B2 | 6/2004 | Hahnen et al. | | 2002/0117534 A1 | 8/2002 | Green et al. |
| 6,767,356 B2 | 7/2004 | Kanner et al. | | 2002/0165541 A1 | 11/2002 | Whitman |
| 6,773,438 B1 | 8/2004 | Knodel et al. | | 2003/0105478 A1 | 6/2003 | Whitman et al. |
| 6,786,382 B1 | 9/2004 | Hoffman | | 2003/0130677 A1 | 7/2003 | Whitman et al. |
| 6,793,652 B1 | 9/2004 | Whitman et al. | | 2003/0216778 A1 | 11/2003 | Weadock |
| 6,805,273 B2 | 10/2004 | Bilotti et al. | | 2003/0220660 A1 | 11/2003 | Kortenbach et al. |
| 6,806,808 B1 | 10/2004 | Watters et al. | | 2004/0002726 A1 | 1/2004 | Nunez et al. |
| 6,814,741 B2 | 11/2004 | Bowman et al. | | 2004/0006372 A1 | 1/2004 | Racenet et al. |
| 6,817,508 B1 | 11/2004 | Racenet et al. | | 2004/0028502 A1 | 2/2004 | Cummins |
| 6,817,509 B2 | 11/2004 | Geiste et al. | | 2004/0034357 A1 | 2/2004 | Beane et al. |
| 6,821,273 B2 | 11/2004 | Mollenauer | | 2004/0044364 A1 | 3/2004 | DeVries et al. |
| 6,828,902 B2 | 12/2004 | Casden | | 2004/0094597 A1 | 5/2004 | Whitman et al. |
| 6,830,174 B2 | 12/2004 | Hillstead et al. | | 2004/0097987 A1 | 5/2004 | Pugsley et al. |
| 6,835,199 B2 | 12/2004 | McGuckin, Jr. et al. | | 2004/0101822 A1 | 5/2004 | Weisner et al. |
| 6,843,403 B2 | 1/2005 | Whitman | | 2004/0108357 A1 | 6/2004 | Milliman et al. |
| 6,846,307 B2 | 1/2005 | Whitman et al. | | 2004/0111081 A1 | 6/2004 | Whitman et al. |
| 6,846,308 B2 | 1/2005 | Whitman et al. | | 2004/0122471 A1 | 6/2004 | Toby et al. |
| 6,846,309 B2 | 1/2005 | Whitman et al. | | 2004/0164123 A1 | 8/2004 | Racenet et al. |
| 6,849,071 B2 | 2/2005 | Whitman et al. | | 2004/0167572 A1 | 8/2004 | Roth et al. |
| RE38,708 E | 3/2005 | Bolanos et al. | | 2004/0173659 A1 | 9/2004 | Green et al. |
| 6,877,647 B2 | 4/2005 | Green et al. | | 2004/0222268 A1 | 11/2004 | Bilotti et al. |
| 6,905,057 B2 | 6/2005 | Swayze et al. | | 2004/0232199 A1 | 11/2004 | Shelton, IV et al. |
| 6,939,358 B2 | 9/2005 | Palacios et al. | | 2004/0232201 A1 | 11/2004 | Wenchell et al. |
| 6,945,444 B2 | 9/2005 | Gresham et al. | | 2004/0243151 A1 | 12/2004 | Demmy et al. |
| 6,953,138 B1 | 10/2005 | Dworak et al. | | 2004/0243176 A1 | 12/2004 | Hahnen et al. |
| 6,953,139 B2 | 10/2005 | Milliman et al. | | 2004/0254608 A1 | 12/2004 | Huitema et al. |
| 6,959,852 B2 | 11/2005 | Shelton, IV et al. | | 2005/0006434 A1 | 1/2005 | Wales et al. |
| 6,964,363 B2 | 11/2005 | Wales et al. | | 2005/0021026 A1 | 1/2005 | Baily |
| 6,978,921 B2 | 12/2005 | Shelton, IV et al. | | 2005/0023324 A1 | 2/2005 | Doll et al. |
| 6,978,922 B2 | 12/2005 | Bilotti et al. | | 2005/0070958 A1 | 3/2005 | Swayze et al. |
| 6,981,628 B2 | 1/2006 | Wales | | 2005/0072827 A1 | 4/2005 | Mollenauer |
| 6,981,941 B2 | 1/2006 | Whitman et al. | | 2005/0080454 A1 | 4/2005 | Drews et al. |
| 6,986,451 B1 | 1/2006 | Mastri et al. | | 2005/0103819 A1 | 5/2005 | Racenet et al. |
| 6,988,649 B2 | 1/2006 | Shelton, IV et al. | | 2005/0107824 A1 | 5/2005 | Hillstead et al. |
| 6,988,650 B2 | 1/2006 | Schwemberger et al. | | 2005/0119669 A1 | 6/2005 | Demmy |
| 7,000,818 B2 | 2/2006 | Shelton, IV et al. | | 2005/0125009 A1 | 6/2005 | Perry et al. |
| 7,000,819 B2 | 2/2006 | Swayze et al. | | 2005/0131390 A1 | 6/2005 | Heinrich et al. |
| 7,008,435 B2 | 3/2006 | Cummins | | 2005/0143759 A1 | 6/2005 | Kelly |
| 7,032,798 B2 | 4/2006 | Whitman et al. | | 2005/0145671 A1 | 7/2005 | Viola |
| 7,032,799 B2 | 4/2006 | Viola et al. | | 2005/0165415 A1 | 7/2005 | Wales |
| 7,044,352 B2 | 5/2006 | Shelton, IV et al. | | 2005/0169974 A1 | 8/2005 | Tenerz et al. |
| 7,044,353 B2 | 5/2006 | Mastri et al. | | 2005/0173490 A1 | 8/2005 | Shelton, IV |
| 7,048,687 B1 | 5/2006 | Reuss et al. | | 2005/0184121 A1 | 8/2005 | Heinrich |
| 7,055,730 B2 | 6/2006 | Ehrenfels et al. | | 2005/0187576 A1 | 8/2005 | Whitman et al. |
| 7,055,731 B2 | 6/2006 | Shelton, IV et al. | | 2005/0189397 A1 | 9/2005 | Jankowski |
| 7,059,508 B2 | 6/2006 | Shelton, IV et al. | | 2005/0203550 A1 | 9/2005 | Laufer et al. |
| 7,063,712 B2 | 6/2006 | Vargas et al. | | 2005/0216055 A1 | 9/2005 | Scirica et al. |
| 7,066,944 B2 | 6/2006 | Laufer et al. | | 2005/0230453 A1 | 10/2005 | Viola |
| 7,070,083 B2 | 7/2006 | Jankowski | | 2005/0263562 A1 | 12/2005 | Shelton, IV et al. |
| 7,077,856 B2 | 7/2006 | Whitman | | 2005/0263563 A1 | 12/2005 | Racenet et al. |
| 7,083,075 B2 | 8/2006 | Swayze et al. | | 2005/0274768 A1 | 12/2005 | Cummins et al. |
| 7,090,673 B2 | 8/2006 | Dycus et al. | | 2006/0011699 A1 | 1/2006 | Olson et al. |
| 7,090,684 B2 | 8/2006 | McGuckin, Jr. et al. | | 2006/0025813 A1 | 2/2006 | Shelton et al. |
| 7,097,089 B2 | 8/2006 | Marczyk | | 2006/0025816 A1 | 2/2006 | Shelton |
| 7,098,794 B2 | 8/2006 | Lindsay et al. | | 2006/0047307 A1 | 3/2006 | Ortiz et al. |

| Pub. No. | Date | Inventor |
|---|---|---|
| 2006/0047308 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0085033 A1 | 4/2006 | Criscuolo et al. |
| 2006/0087442 A1 | 4/2006 | Smith et al. |
| 2006/0097026 A1 | 5/2006 | Shelton, IV |
| 2006/0100643 A1 | 5/2006 | Laufer et al. |
| 2006/0122636 A1 | 6/2006 | Bailley et al. |
| 2006/0142772 A1 | 6/2006 | Ralph et al. |
| 2006/0151567 A1 | 7/2006 | Roy |
| 2006/0173470 A1 | 8/2006 | Oray et al. |
| 2006/0183246 A1 | 8/2006 | Wiesner et al. |
| 2006/0190028 A1 | 8/2006 | Wales et al. |
| 2006/0226196 A1 | 10/2006 | Hueil et al. |
| 2006/0245971 A1 | 11/2006 | Burns et al. |
| 2006/0278680 A1 | 12/2006 | Viola et al. |
| 2006/0278681 A1 | 12/2006 | Viola et al. |
| 2006/0289602 A1 | 12/2006 | Wales et al. |
| 2006/0291981 A1 | 12/2006 | Viola et al. |
| 2007/0034666 A1 | 2/2007 | Holsten et al. |
| 2007/0034668 A1 | 2/2007 | Holsten et al. |
| 2007/0045379 A1 | 3/2007 | Shelton, IV |
| 2007/0075114 A1 | 4/2007 | Shelton, IV et al. |
| 2007/0083234 A1 | 4/2007 | Shelton, IV et al. |
| 2007/0084897 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0102475 A1 | 5/2007 | Ortiz et al. |
| 2007/0102476 A1 | 5/2007 | Shelton, IV et al. |
| 2007/0106317 A1 | 5/2007 | Shelton, IV et al. |
| 2007/0158385 A1 | 7/2007 | Hueil et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175952 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175960 A1 | 8/2007 | Shelton, IV et al. |
| 2007/0175961 A1 | 8/2007 | Shelton, IV et al. |
| 2007/0175962 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0213750 A1 | 9/2007 | Weadock |
| 2007/0233053 A1 | 10/2007 | Shelton, IV et al. |
| 2007/0262116 A1 | 11/2007 | Hueil et al. |
| 2007/0295780 A1 | 12/2007 | Shelton et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0035701 A1 | 2/2008 | Racenet et al. |
| 2008/0041917 A1 | 2/2008 | Racenet et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |

FOREIGN PATENT DOCUMENTS

| | | |
|---|---|---|
| CA | 2512960 A1 | 1/2006 |
| CA | 2514274 A1 | 1/2006 |
| DE | 273689 C | 5/1914 |
| DE | 9412228 U | 9/1994 |
| DE | 69328576 T2 | 1/2001 |
| DE | 20112837 U1 | 10/2001 |
| DE | 20121753 U1 | 4/2003 |
| DE | 10314072 A1 | 10/2004 |
| EP | 0122046 A1 | 10/1984 |
| EP | 0033548 B1 | 5/1986 |
| EP | 0639349 A2 | 2/1994 |
| EP | 0593920 A1 | 4/1994 |
| EP | 0600182 A2 | 6/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0669104 A1 | 8/1995 |
| EP | 0679367 A2 | 11/1995 |
| EP | 0392547 B1 | 12/1995 |
| EP | 0685204 A1 | 12/1995 |
| EP | 0699418 A1 | 3/1996 |
| EP | 0702937 A1 | 3/1996 |
| EP | 0705571 A1 | 4/1996 |
| EP | 0484677 B2 | 6/1996 |
| EP | 0541987 B1 | 7/1996 |
| EP | 0667119 B1 | 7/1996 |
| EP | 0770355 A1 | 5/1997 |
| EP | 0503662 B1 | 6/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0603472 B1 | 11/1998 |
| EP | 0878169 A1 | 11/1998 |
| EP | 0760230 B1 | 2/1999 |
| EP | 0537572 B1 | 6/1999 |
| EP | 0552050 B1 | 5/2000 |
| EP | 1090592 A1 | 4/2001 |
| EP | 1256318 B1 | 5/2001 |
| EP | 0908152 B1 | 1/2002 |
| EP | 0872213 B1 | 5/2002 |
| EP | 1238634 A2 | 9/2002 |
| EP | 0656188 B1 | 1/2003 |
| EP | 0829235 B1 | 6/2003 |
| EP | 0813843 B1 | 10/2003 |
| EP | 0705570 B1 | 4/2004 |
| EP | 1086713 B1 | 5/2004 |
| EP | 1426012 A1 | 6/2004 |
| EP | 0888749 B1 | 9/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 1520523 A1 | 4/2005 |
| EP | 1520525 A1 | 4/2005 |
| EP | 1522264 A1 | 4/2005 |
| EP | 1550408 A1 | 7/2005 |
| EP | 1557129 A1 | 7/2005 |
| EP | 1064883 B1 | 8/2005 |
| EP | 1621141 A2 | 2/2006 |

| | | | | | | |
|---|---|---|---|---|---|---|
| EP | 1652481 | A2 | 5/2006 | WO | WO 03/088845 A2 | 10/2003 |
| EP | 1382303 | B1 | 6/2006 | WO | WO 03/090630 A2 | 11/2003 |
| EP | 1045672 | B1 | 8/2006 | WO | WO 03/094743 A1 | 11/2003 |
| EP | 1617768 | B1 | 8/2006 | WO | WO 03/094745 A1 | 11/2003 |
| EP | 1702567 | A2 | 9/2006 | WO | WO 03/094746 A1 | 11/2003 |
| EP | 1129665 | B1 | 11/2006 | WO | WO 03/094747 A1 | 11/2003 |
| EP | 1256317 | B1 | 12/2006 | WO | WO 03/101313 A1 | 12/2003 |
| EP | 1728473 | A1 | 12/2006 | WO | WO 03/105702 A2 | 12/2003 |
| EP | 1728475 | A2 | 12/2006 | WO | WO 2004/006980 A2 | 1/2004 |
| EP | 1484024 | B1 | 1/2007 | WO | WO 2004/032754 A2 | 4/2004 |
| EP | 1300117 | B1 | 8/2007 | WO | WO 2004/032760 A2 | 4/2004 |
| FR | 1112936 | A | 3/1956 | WO | WO 2004/032762 A1 | 4/2004 |
| GB | 939929 | A | 10/1963 | WO | WO 2004/032763 A2 | 4/2004 |
| GB | 2336214 | A | 10/1999 | WO | WO 2004/047653 A2 | 6/2004 |
| JP | 6007357 | A | 1/1994 | WO | WO 2004/049956 A2 | 6/2004 |
| JP | 7051273 | A | 2/1995 | WO | WO 2004/086987 A1 | 10/2004 |
| JP | 8033641 | A | 2/1996 | WO | WO 2004/096057 A2 | 11/2004 |
| JP | 8229050 | A | 9/1996 | WO | WO 2004/112618 A2 | 12/2004 |
| JP | 2001286477 | A | 10/2001 | WO | WO 2005/027983 A2 | 3/2005 |
| JP | 2002369820 | A | 12/2002 | WO | WO 2005/096954 A2 | 10/2005 |
| JP | 2005505322 | T | 2/2005 | WO | WO 2005/115251 A2 | 12/2005 |
| JP | 2005103293 | A | 4/2005 | WO | WO 2006/044490 A2 | 4/2006 |
| RU | 2187249 | C2 | 8/2002 | WO | WO 2006/044581 A2 | 4/2006 |
| RU | 2225170 | C2 | 3/2004 | WO | WO 2006/044810 A2 | 4/2006 |
| SU | 1377053 | A1 | 2/1988 | WO | WO 2006/083748 A1 | 8/2006 |
| SU | 1561964 | A1 | 5/1990 | WO | WO 2006/132992 A1 | 12/2006 |
| SU | 1722476 | A1 | 3/1992 | WO | WO 2007/016290 A2 | 2/2007 |
| WO | WO 93/08755 | A1 | 5/1993 | | | |
| WO | WO 95/18572 | A1 | 7/1995 | | | |
| WO | WO 95/29639 | A1 | 11/1995 | | | |
| WO | WO 96/35464 | A1 | 11/1996 | | | |
| WO | WO 98/30153 | A1 | 7/1998 | | | |
| WO | WO 99/12483 | A1 | 3/1999 | | | |
| WO | WO 99/15086 | A1 | 4/1999 | | | |
| WO | WO 99/34744 | A1 | 7/1999 | | | |
| WO | WO 00/57796 | A1 | 10/2000 | | | |
| WO | WO 00/72762 | A1 | 12/2000 | | | |
| WO | WO 00/72765 | A1 | 12/2000 | | | |
| WO | WO 01/05702 | A1 | 1/2001 | | | |
| WO | WO 01/10482 | A1 | 2/2001 | | | |
| WO | WO 01/62158 | A2 | 8/2001 | | | |
| WO | WO 01/62162 | A1 | 8/2001 | | | |
| WO | WO 01/62164 | A2 | 8/2001 | | | |
| WO | WO 01/91646 | A1 | 12/2001 | | | |
| WO | WO 02/17799 | A1 | 3/2002 | | | |
| WO | WO 02/30297 | A2 | 4/2002 | | | |
| WO | WO 02/32322 | A2 | 4/2002 | | | |
| WO | WO 02/043571 | A2 | 6/2002 | | | |
| WO | WO 02/067785 | A2 | 9/2002 | | | |
| WO | WO 02/098302 | A1 | 12/2002 | | | |
| WO | WO 03/000138 | A2 | 1/2003 | | | |
| WO | WO 03/001329 | A2 | 1/2003 | | | |
| WO | WO 03/013363 | A1 | 2/2003 | | | |
| WO | WO 03/020106 | A2 | 3/2003 | | | |
| WO | WO 03/079909 | A3 | 3/2003 | | | |
| WO | WO 03/030743 | A2 | 4/2003 | | | |
| WO | WO 03/037193 | A1 | 5/2003 | | | |
| WO | WO 03/047436 | A3 | 6/2003 | | | |
| WO | WO 03/057048 | A1 | 7/2003 | | | |
| WO | WO 03/057058 | A1 | 7/2003 | | | |
| WO | WO 03/063694 | A1 | 8/2003 | | | |
| WO | WO 03/077769 | A1 | 9/2003 | | | |
| WO | WO 03/082126 | A1 | 10/2003 | | | |

OTHER PUBLICATIONS

U.S. Appl. No. 11/497,898, filed Aug. 2, 2006.
U.S. Appl. No. 11/541,164, filed Sep. 29, 2006.
U.S. Appl. No. 11/529,879, filed Sep. 29, 2006.
U.S. Appl. No. 11/541,050, filed Sep. 29, 2006.
U.S. Appl. No. 11/541,151, filed Sep. 29, 2006.
U.S. Appl. No. 11/528,904, filed Sep. 29, 2006.
U.S. Appl. No. 11/529,935, filed Sep. 29, 2006.
U.S. Appl. No. 11/541,123, filed Sep. 29, 2006.
U.S. Appl. No. 11/541,182, filed Sep. 29, 2006.
U.S. Appl. No. 11/541,098, filed Sep. 29, 2006.
U.S. Appl. No. 11/541,374, filed Sep. 29, 2006.
International Search Report for PCT/US2007/011309, Jan. 22, 2008 (5 pages).
Disclosed Anonymously, "Motor-Driven Surgical Stapler Improvements," Research Disclosure Database No. 526041, Published: Feb. 2008.
U.S. Appl. No. 11/824,251, filed Jun. 29, 2007.
U.S. Appl. No. 12/038,939, filed Feb. 28, 2008.
U.S. Appl. No. 11/652,165, filed Jan. 11, 2007.
U.S. Appl. No. 11/824,389, filed Jun. 29, 2007.
U.S. Appl. No. 11/824,415, filed Jun. 29, 2007.
U.S. Appl. No. 11/824,274, filed Jun. 29, 2007.
U.S. Appl. No. 11/824,275, filed Jun. 29, 2007.
U.S. Appl. No. 11/823,988, filed Jun. 29, 2007.
U.S. Appl. No. 11/824,079, filed Jun. 29, 2007.
U.S. Appl. No. 11/824,524, filed Jun. 29, 2007.
U.S. Appl. No. 11/824,298, filed Jun. 29, 2007.
U.S. Appl. No. 11/824,252, filed Jun. 29, 2007.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

* cited by examiner

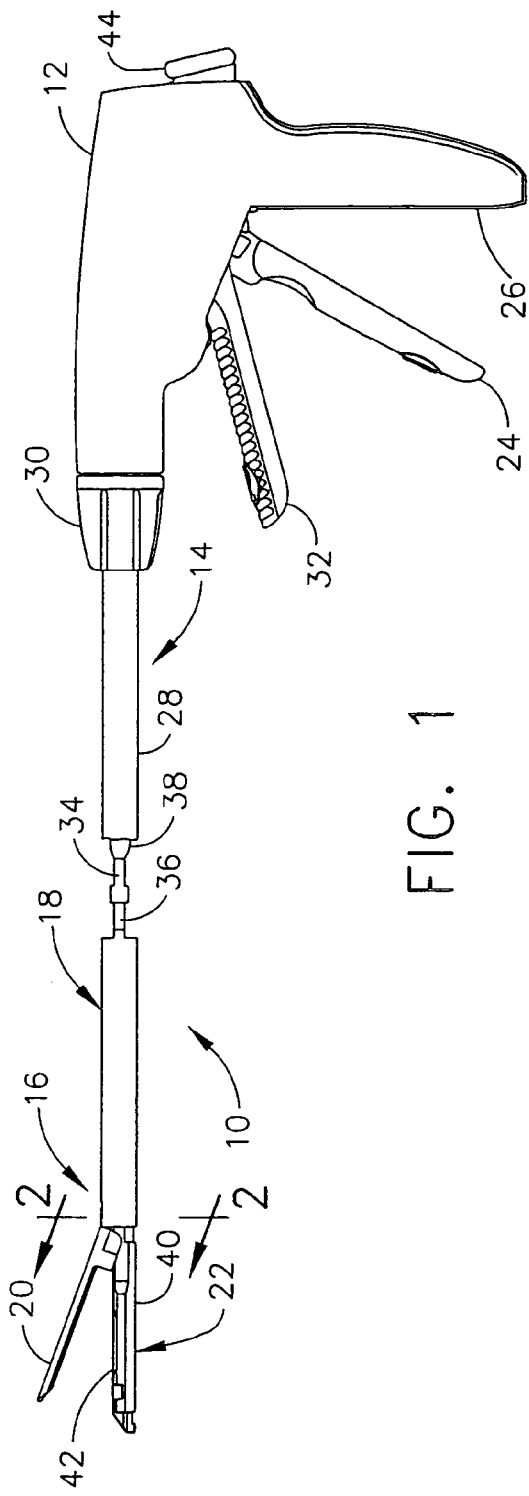
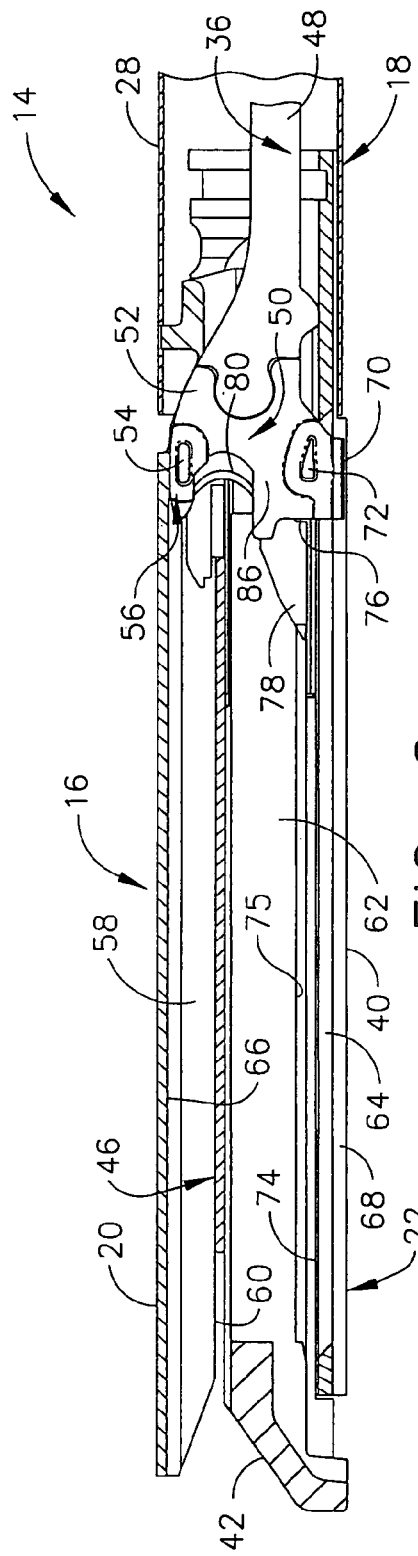
FIG. 1
FIG. 2

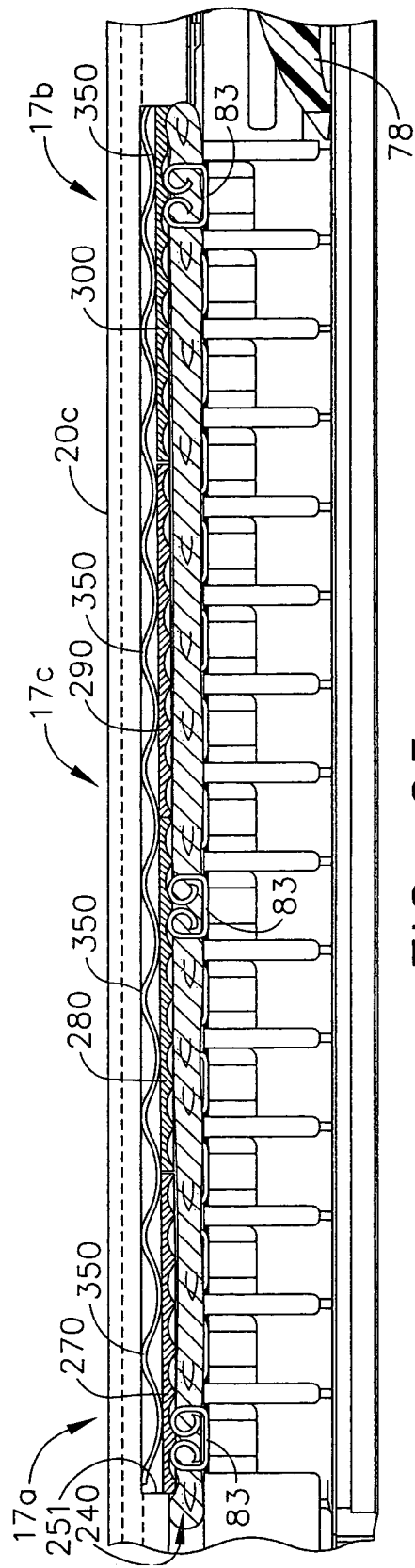
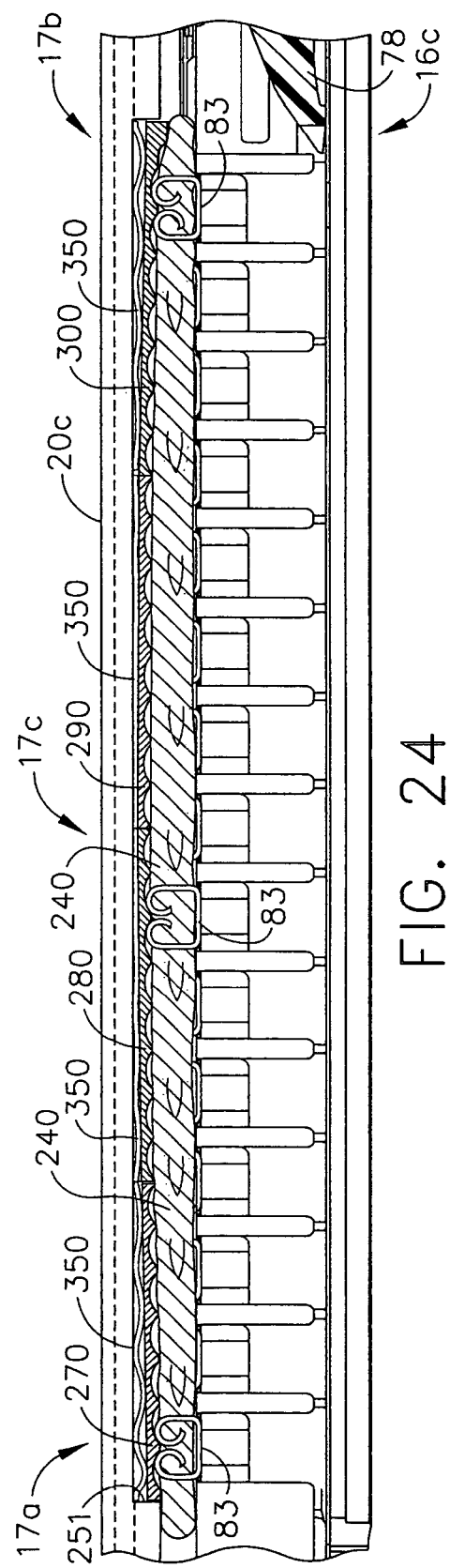
FIG. 23
FIG. 24

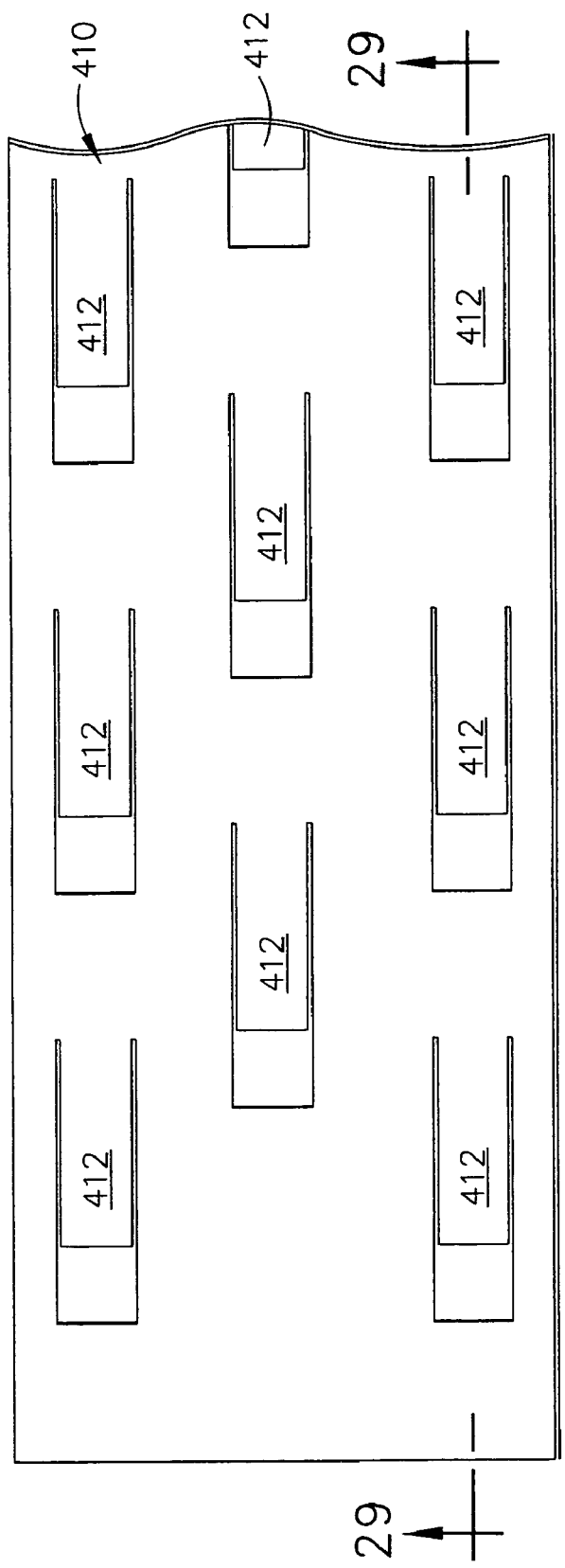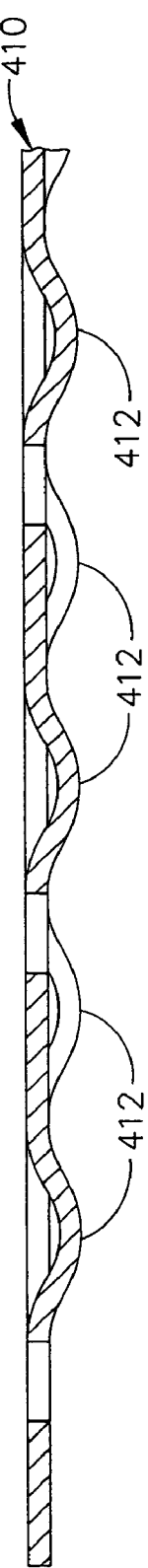
FIG. 28
FIG. 29

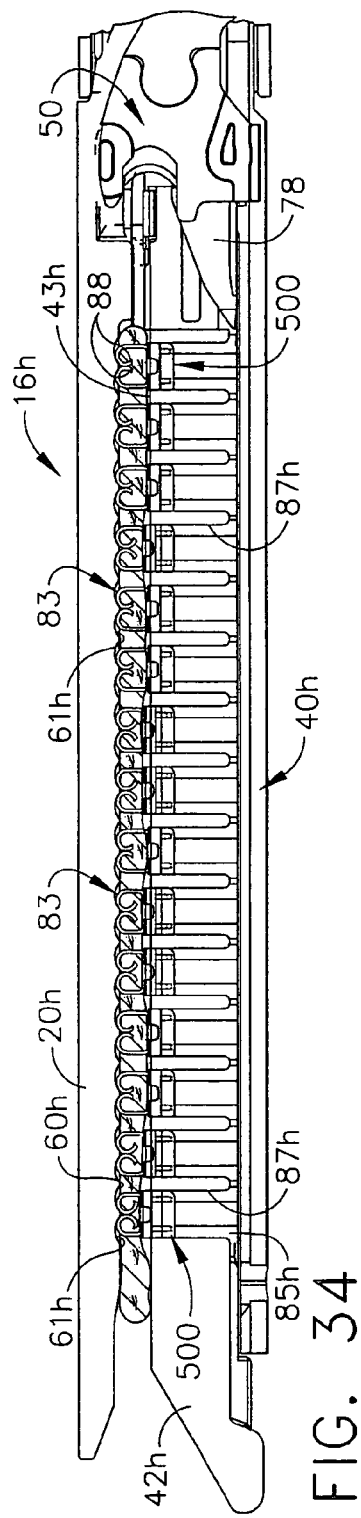
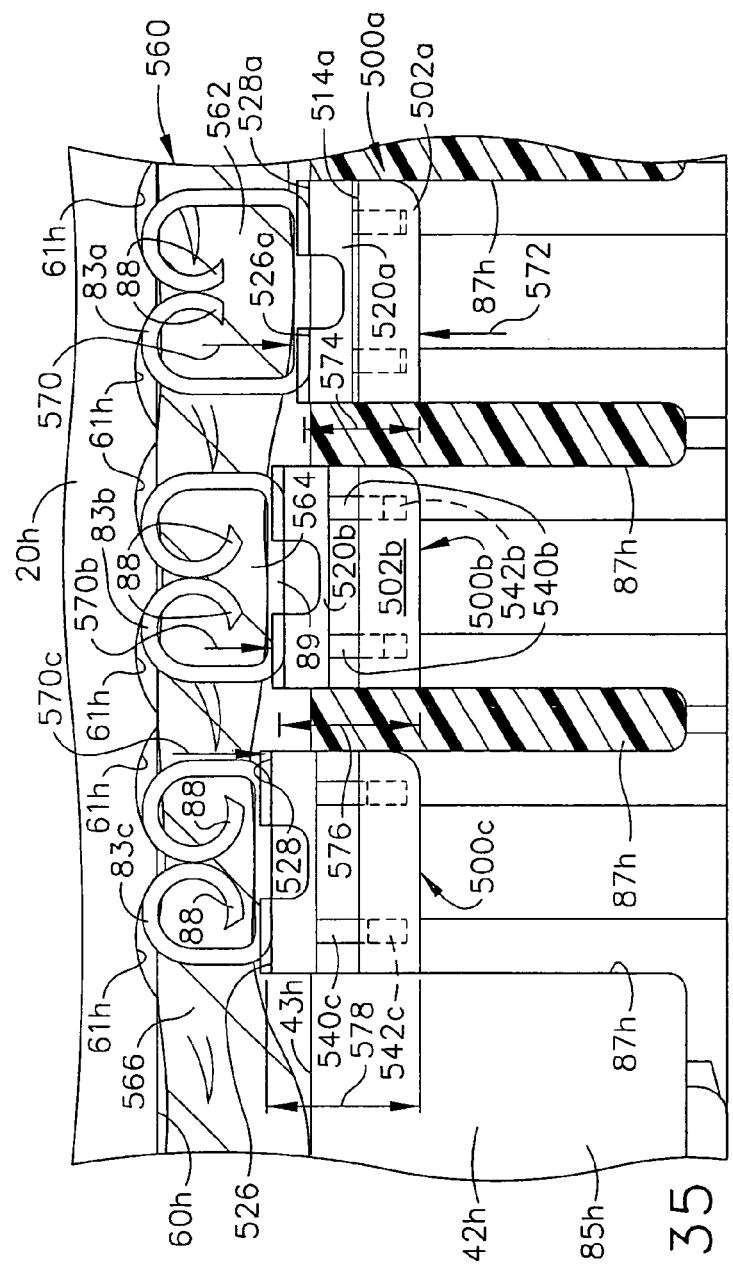
FIG. 34
FIG. 35

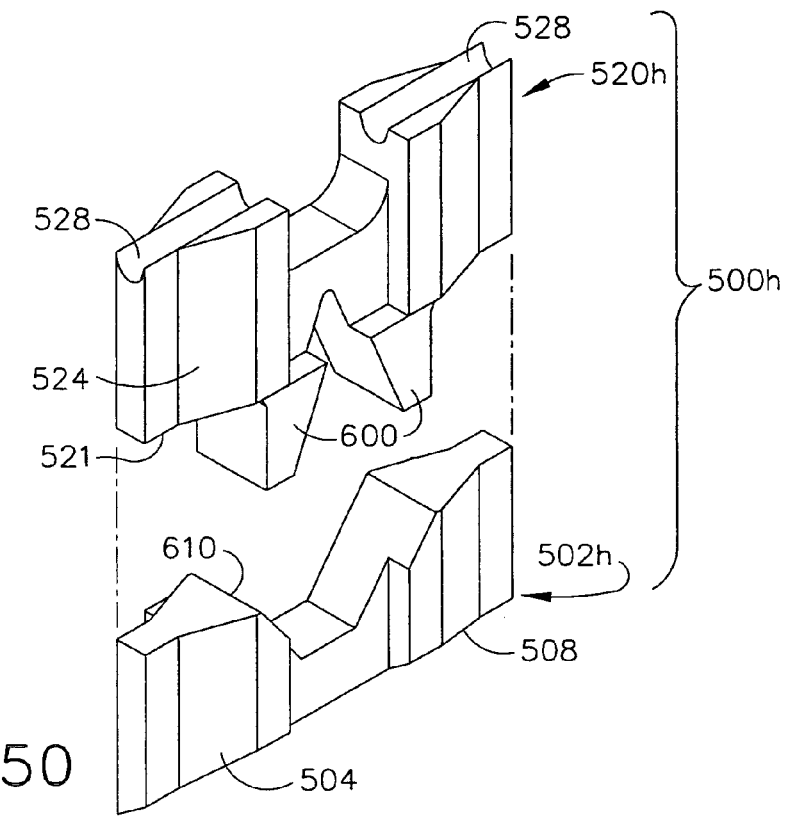
FIG. 50
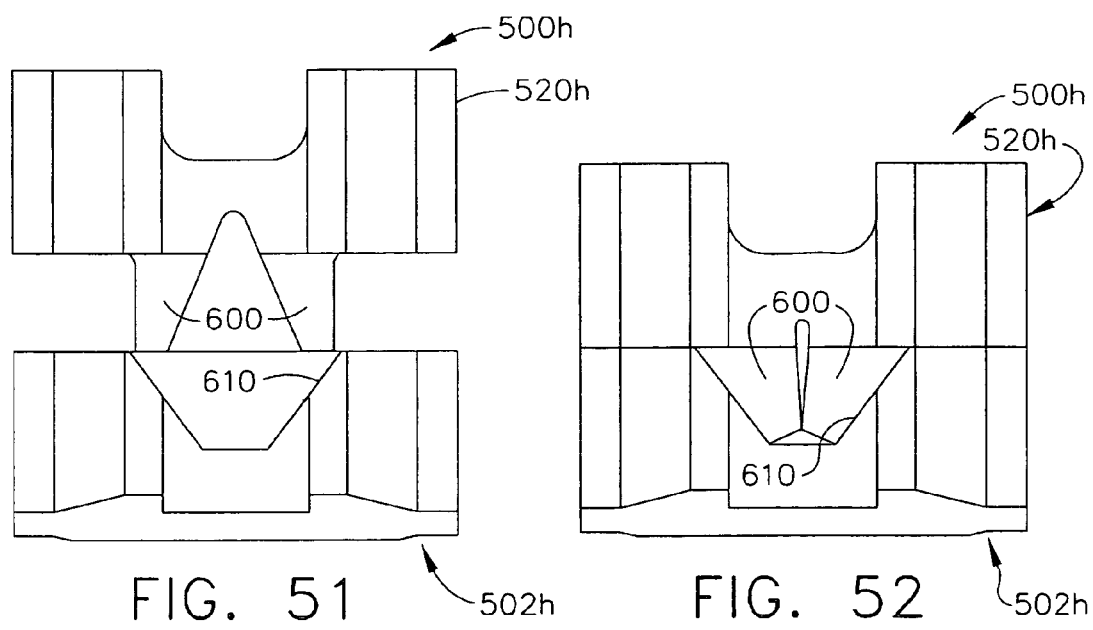
FIG. 51
FIG. 52

SURGICAL STAPLING INSTRUMENTS WITH COLLAPSIBLE FEATURES FOR CONTROLLING STAPLE HEIGHT

CROSS REFERENCE TO RELATED APPLICATIONS

The subject application is a continuation-in-part application of U.S. patent application Ser. No. 11/231,456, filed Sep. 21, 2005 and entitled "Surgical Stapling Instrument Having Force Controlled Spacing End Effector", the disclosure of which is herein incorporated by reference in its entirety. This application is also related to the following U.S patent application which is being concurrently filed herewith and which is herein incorporated by reference: Surgical Stapling Instruments Having Flexible Channel and Anvil Features For Adustable Staple Heights, Inventors: Frederick E. Shelton, IV, Jerome R. Morgan, Michael A. Murray, Richard W. Timm, James T. Spivey, James W. Voegele, Leslie M. Fugikawa, and Eugene L. Timperman, U.S. patent application Ser. No. 11/540,735, filed Sep. 29, 2006.

FIELD OF THE INVENTION

The present invention relates in general to surgical stapler instruments that are capable of applying lines of staples to tissue while cutting the tissue between those staple lines and, more particularly, to improvements relating to stapler instruments and improvements in processes for forming various components of such stapler instruments including adding bolstering material to the severed and stapled tissue.

BACKGROUND

Endoscopic and laparoscopic surgical instruments are often preferred over traditional open surgical devices since a smaller incision tends to reduce the post-operative recovery time and complications. The use of laparoscopic and endoscopic surgical procedures has been relatively popular and has provided additional incentive to develop the procedures further. In laparoscopic procedures, surgery is performed in the interior of the abdomen through a small incision. Similarly, in endoscopic procedures, surgery is performed in any hollow viscus of the body through narrow endoscopic tubes inserted through small entrance wounds in the skin.

Laparoscopic and endoscopic procedures generally require that the surgical region be insufflated. Accordingly, any instrumentation inserted into the body must be sealed to ensure that gases do not enter or exit the body through the incision. Moreover, laparoscopic and endoscopic procedures often require the surgeon to act on organs, tissues and/or vessels far removed from the incision. Thus, instruments used in such procedures are typically long and narrow while being functionally controllable from a proximal end of the instrument.

Significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

Recently, an improved "E-beam" firing bar was described for a surgical stapling and severing instrument that advantageously included a top pin that slides within an internal slot formed in the upper jaw (anvil) and has a middle pin and bottom foot that slides on opposite sides of a lower jaw of an end effector, or more particularly a staple applying assembly. Distal to the middle pin, a contacting surface actuates a staple cartridge held within an elongate staple channel that forms the lower jaw. Between the contacting surface and the top pin, a cutting surface, or knife, severs tissue clamped between the anvil and the staple cartridge of the lower jaw. Since both jaws are thus engaged by the E-beam, the E-beam maintains a desired spacing between the jaws to ensure proper staple formation. Thus, if a lesser amount of tissue is clamped, the E-beam holds up the anvil to ensure sufficient spacing for the staples to properly form against an undersurface of the anvil. In addition, if a greater amount of tissue is clamped, the E-beam draws down the anvil to ensure that the spacing does not exceed the length of the staple such that ends of each staple are not sufficiently bent to achieve a desired degree of retention. Such an E-beam firing bar is described in U.S. patent application Ser. No. 10/443,617, entitled "Surgical Stapling Instrument Incorporating an E-Beam Firing Mechanism", filed on May 20, 2003, now U.S. Pat. No. 6,978,921, issued Dec. 27, 2005, the disclosure of which is hereby incorporated by reference in its entirety.

While an E-beam firing bar has many advantages for a surgical stapling and severing instrument, often it is desirable to sever and staple tissue of various thicknesses. A thin layer of tissue may result in staples that only form loosely, perhaps requiring the need for bolstering material. A thick layer of tissue may result in formed staples that exert a strong compressive force on the captured tissue, perhaps resulting in necrosis, bleeding or poor staple formation/retention. Rather than limiting the range of tissue thicknesses that are appropriate for a given surgical stapling and severing instrument, it would be desirable to accommodate a wider range of tissue thickness with the same surgical stapling and severing instrument.

Consequently, a significant need exists for an improved surgical stapling and severing instrument that incorporates a staple applying assembly (end effector) that adjusts to the amount of tissue that is clamped.

In addition, the staple drivers that are commonly employed in existing staple applying assemblies are traditionally made as stiff as possible to assure proper "B" form staple height. Because of this stiff construction, these drivers do not provide any flexibility for adjusting the formed height of the staple to a particular thickness of tissue clamped within the assembly.

Thus, another significant need exists for staple drivers that are able to facilitate the adjustment of the formed height of the staples in response to variations in tissue thickness.

BRIEF SUMMARY

The invention overcomes the above-noted and other deficiencies of the prior art by providing a surgical instrument that incorporates a firing bar that translates through a staple applying assembly having a lower jaw and a pivotally attached upper jaw, engaging each to assist in maintaining the desired spacing between inner surfaces that compress tissue in between. Advantageously, the distance between the two jaws is allowed to flex apart slightly to allow for a larger thickness of compressed tissue, yet the firing bar prevents excessive flexure that would exceed the limits on the device to form staples through the compressed tissue. Thereby, enhanced clinical flexibility is achieved with the same surgical instrument being suitable for a larger range of surgical procedures or to accommodate variations in the patient population.

In one aspect of the invention, a surgical instrument has a lower jaw that includes an elongate staple channel having a longitudinal channel slot formed therein that receives a staple cartridge. Staples in the staple cartridge have a staple length sized for forming a closed staple between a range of tissue thicknesses. A firing bar has a vertical portion passing through a longitudinal anvil slot in an anvil pivotally attached to the elongate staple channel and passes through the longitudinal channel slot formed in the elongate staple channel. An upper lateral surface extending from the vertical portion exerts an inward compressive force on the anvil during firing translation and a lower lateral surface extending from the vertical portion exerts an inward compressive force on the elongate staple channel during firing translation. The firing bar advantageously accommodates the range of effective staple formation by including a resilient portion that varies in height between a staple forming undersurface of an anvil and an upper surface of the staple cartridge.

In another aspect of the invention, a surgical instrument has an anvil that is pivotally coupled to the elongate staple channel and includes an anvil channel that is internally formed. In particular, a vertical slot inwardly opens along a longitudinal axis of the anvil and has left and right rectangular prism-shaped recesses communicating with, bisected by, and transverse to the vertical slot, wherein said left and right rectangular prism-shaped recesses extend substantially along the longitudinal length of the vertical slot. A firing device that includes a distally presented cutting edge for severing tissue is longitudinally received between the elongate staple channel and the vertical slot of the anvil channel of the anvil. An upper member of the firing device has left and right lateral upper pins sized to slidingly engage upper and lower inner surfaces of the left and right rectangular-shaped recesses of the anvil channel. A lower member of the firing device engages the channel slot in the elongate staple cartridge. A middle member of the firing device actuates the staple cartridge by distally translating a wedge member of the staple cartridge. The firing device positively engages both the elongate staple channel and the anvil during longitudinal firing travel to provide spacing in between for staple formation. Engagement of the firing device during firing maintains vertical spacing between the elongate staple channel and the anvil resisting both pinching due to an inadequate clamped tissue and partial opening due to an excessive amount of clamped tissue. This affirmative spacing is advantageously varied within an effective range of the staple length of the staple cartridge by incorporating a resilient portion in the firing device to allow some flexure to accommodate an increased compression load due to a thicker layer of clamped tissue.

In yet another aspect of the invention, the surgical instrument advantageously operates through an elongate shaft with a closed end effector of upper and lower jaws suitably sized for insertion through a cannula of a trocar to an insufflated body cavity or body lumen.

In another aspect of the invention there is disclosed a surgical instrument that comprises an elongate channel that is configured to operably support a staple cartridge therein. An anvil is pivotably coupled to the elongate channel and is selectively pivotable between an open position and a closed position wherein a staple forming undersurface thereof is in confronting relationship to an upper surface of a staple cartridge supported within the elongate channel in response to a closing motion applied to the anvil and from a closed position to the open position in response to an opening motion applied to the anvil. A firing member is operably supported relative to the elongate channel and is selectively longitudinally translatable from an unfired position through the elongate channel in a staple firing motion in response to a firing force applied to the firing member and to retract to the unfired position in response to a retraction force applied to the firing member. In various embodiments, at least one of the elongate channel and the anvil has a resilient structure configured to flexibly interact with the firing member during the staple firing motion to allow a distance between the staple forming undersurface of the anvil and the upper surface of the staple cartridge to vary in relation to a thickness of tissue clamped between the staple forming undersurface of the anvil and the upper surface of the staple cartridge.

In another general aspect of the present invention there is disclosed a surgical instrument that comprises an elongate staple channel that has a first flexible portion and a second flexible portion that is spaced from the first flexible portion to define a longitudinal channel slot therebetween. A staple cartridge is operably supported within the elongate staple channel and an elongate shaft is operably coupled to the elongate staple channel. An anvil is pivotally attached to the elongate staple channel and is selectively pivotable between a closed position wherein a staple forming undersurface thereof is in confronting relationship to an upper surface of the staple cartridge and an open position wherein a distal end of the anvil is spaced from the upper surface of the staple cartridge. The anvil further has a longitudinal anvil slot therein. A control handle assembly is proximally operably coupled through the elongate shaft to selectively apply opening and closing motions to the anvil. A firing member is operably coupled to the control handle assembly through the elongate shaft for selective longitudinal reciprocating motion in the elongate staple channel such that one portion of the firing member extends through the longitudinal anvil slot and another portion of the firing member extends through the longitudinal channel slot between the first and second flexible portions.

In yet another general aspect of the present invention there is disclosed a surgical instrument that comprises an elongate staple channel that has a longitudinal channel slot. A staple cartridge is operably supported within the elongate staple channel. An elongate shaft is operably coupled to the elongate staple channel. An anvil is pivotally attached to the elongate staple channel and is selectively pivotable between a closed position wherein a staple forming undersurface thereof is in confronting relationship to an upper surface of the staple cartridge and an open position wherein a distal end of the anvil is spaced from the upper surface of the staple cartridge. The anvil further has a first resilient anvil portion and a second resilient anvil portion that is spaced from the first resilient anvil portion to define a portion of an elongate anvil slot therebetween. A control handle assembly is proximally operably coupled through the elongate shaft to selectively apply opening and closing motions to the anvil. A firing member is operably coupled to the control handle assembly through the elongate shaft for selective longitudinal reciprocating motion in the elongate staple channel such that one portion of the firing member extends through the anvil slot between the first and second resilient anvil portions and another portion of the firing member extends through the longitudinal channel slot.

Another general aspect of the present invention comprises a collapsible staple driver for use in a surgical staple cartridge. In various embodiments, the collapsible staple driver includes a base portion that is configured to be operably supported by the surgical staple cartridge and a staple supporting portion that is also configured to be operably supported within the surgical staple cartridge adjacent to said base portion. A resistive attachment structure is provided to coact with the base portion and said staple supporting portion to support the staple supporting portion in a first position relative to the base portion and is configured to permit the staple supporting portion to move toward the base portion in response to compression forces applied to the staple supporting portion and the base portion during a staple firing operation.

Still another general aspect of the present invention comprises a surgical stapling instrument that may include an elongate channel and a staple cartridge that is supported within the elongate channel. The staple cartridge may operably support a plurality of collapsible staple supporting drivers therein. An anvil may be pivotably coupled to the elongate channel and may be selectively pivotable between an open position and a closed position wherein a staple forming undersurface thereof is in confronting relationship to an upper surface of the staple cartridge. A drive member may be operably supported relative to the elongate channel and may be selectively longitudinally translatable from an unfired position through the elongate channel wherein the drive member drives the collapsible staple drivers toward the staple forming undersurface of the anvil when the anvil is in the closed position in response to a firing force applied to the drive member Yet another general aspect of the present invention is directed to a surgical stapling instrument that may include a staple cartridge and means for supporting the staple cartridge. An anvil may be pivotably supported relative to the means for supporting such that the anvil may be moved from an open position to a closed position wherein a staple forming undersurface thereof is in confronting relationship to an upper surface of the staple cartridge. A plurality of staple supporting means are provided within the staple cartridge for supporting a plurality of staples therein. Each staple supporting means may be collapsible as they are driven toward the staple forming undersurface of the anvil when the anvil is in the closed position. Each of the staple supporting means may support at least one staple thereon. The instrument may further comprise means for selectively driving the staple supporting means toward the anvil when in the closed position in response to a firing force applied to the means for selectively driving.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 1 is a left side view in elevation of a surgical stapling and severing instrument with an open end effector (staple applying assembly) with a shaft partially cut away to expose a firing member of a proximal firing rod and distal firing bar guided by a frame ground and encompassed by a closure sleeve.

FIG. 2 is a left side view of a closed end effector (staple applying assembly) with a retracted force adjusted height firing bar consistent with the present invention of the surgical stapling and severing instrument of FIG. 1 taken in longitudinal vertical cross section along lines 2-2.

FIG. 23 is another partial longitudinal cross-sectional view of the staple applying assembly of FIGS. 20-22 clamping another piece of tissue therein.

FIG. 24 is another partial longitudinal cross-sectional of the staple applying assembly of FIGS. 20-23 clamping another piece of tissue therein.

FIG. 28 is a top view of a portion of a biasing plate embodiment of the present invention.

FIG. 29 is a cross-sectional view of a portion of the biasing plate of FIG. 28 taken along line 29-29 in FIG. 28.

FIG. 34 is a longitudinal cross-sectional view of a staple applying assembly of other embodiments of the present invention wherein tissue of varying thickness is clamped therein.

FIG. 35 is an enlarged cross-sectional view of a portion of the staple applying assembly of FIG. 34.

FIG. 50 is an exploded assembly view of another collapsible staple driver embodiment of the present invention.

FIG. 51 is an exploded front view of the collapsible staple driver embodiment of FIG. 50.

FIG. 52 is another front view of the collapsible staple driver embodiment of FIGS. 50 and 51 after being compressed into a fully collapsed position.

DETAILED DESCRIPTION

Figure 3:
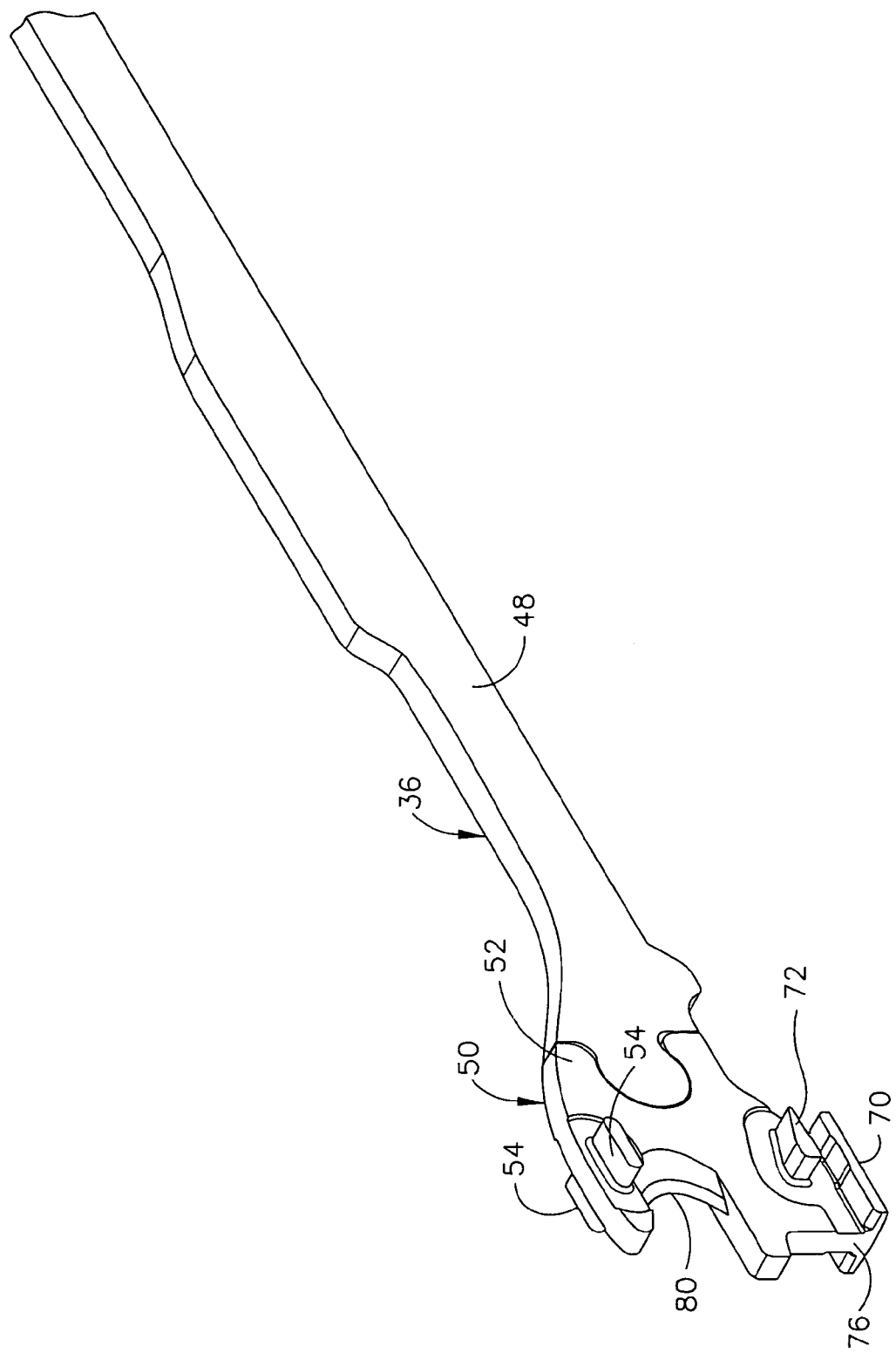
FIG. 3 is a left isometric view of the force adjusted (compliant) height firing bar of FIG. 2.

Turning to the Drawings, wherein like numerals denote like components throughout the several views, in FIG. 1, a surgical stapling and severing instrument 10 includes a handle portion 12 that is manipulated to position an implement portion 14 including a fastening end effector, depicted as a staple applying assembly 16, distally attached to an elongate shaft 18. The implement portion 14 is sized for insertion through a cannula of a trocar (not shown) for an endoscopic or laparoscopic surgical procedure with an upper jaw (anvil) 20 and a lower jaw 22 of the staple applying assembly 16 closed by depression of a closure trigger 24 toward a pistol grip 26 of the handle portion 12, which advances an outer closure sleeve 28 of the elongate shaft 18 to pivot shut the anvil 20.

Once inserted into an insufflated body cavity or lumen, the surgeon may rotate the implement portion 14 about its longitudinal axis by twisting a shaft rotation knob 30 that engages across a distal end of the handle 12 and a proximal end of the elongate shaft 18. Thus positioned, the closure trigger 24 may be released, opening the anvil 20 so that tissue may be grasped and positioned. Once satisfied with the tissue held in the staple applying assembly 16, the surgeon depresses the closure trigger 24 until locked against the pistol grip 26, clamping tissue inside of the staple applying assembly 16.

Then a firing trigger 32 is depressed, drawn toward the closure trigger 24 and pistol grip 26, thereby applying a firing force or motion thereto to distally advance a firing member from an unfired position. The firing member is depicted as including a proximal firing rod 34 attached to a distal firing bar 36, that is supported within a frame ground 38 that connects the handle portion 12 to the staple applying assembly 16. During the staple firing motion, the firing bar 36 engages an elongate staple channel 40 and actuates a staple cartridge 42 contained therein, both forming the lower jaw 22. The firing bar 36 also engages the closed anvil 20. After releasing the firing trigger 32 to apply a retraction force or motion to the firing bar 36, depression of a closure release button 44 unclamps the closure trigger 24 so that the closure sleeve 28 may be retracted to pivot and open the anvil 20 to release the severed and stapled tissue from the staple applying assembly 16.

It should be appreciated that spatial terms such as vertical, horizontal, right, left etc., are given herein with reference to the figures assuming that the longitudinal axis of the surgical instrument 10 is co-axial to the central axis of the elongate shaft 18, with the triggers 24, 32 extending downwardly at an acute angle from the bottom of the handle assembly 12. In actual practice, however, the surgical instrument 10 may be oriented at various angles and, as such, these spatial terms are used relative to the surgical instrument 10 itself. Further, "proximal" is used to denote a perspective of a clinician who is behind the handle assembly 12 who places the implement portion 14 distal, or away from him or herself.

In FIG. 2, the staple applying assembly 16 is closed upon compressed tissue 46. In FIGS. 2-3, the firing bar 36 has a proximal portion 48 that is attached to a distal E-beam 50 that translates within the staple applying assembly 16. As depicted with the firing bar 36 retracted, a vertical portion 52 of the E-beam 50 resides essentially aft of the staple cartridge 42, as after a new staple cartridge 42 has been inserted into the elongate staple channel 40. An upper pin 54 that extends laterally from an upper portion of the vertical portion 52 of the E-beam 50 initially resides within an anvil pocket 56 recessed near a proximal pivoting end of the anvil 20. As the E-beam 50 is distally advanced during the staple firing motion, the vertical portion 52 passes through a narrow longitudinal anvil slot 58 (FIGS. 1, 11) formed in a staple forming undersurface 60 of the anvil 20, a proximally open vertical slot 62 formed in cartridge 42 and an underlying longitudinal channel slot 64 formed in the elongate staple channel 40.

Figure 11:
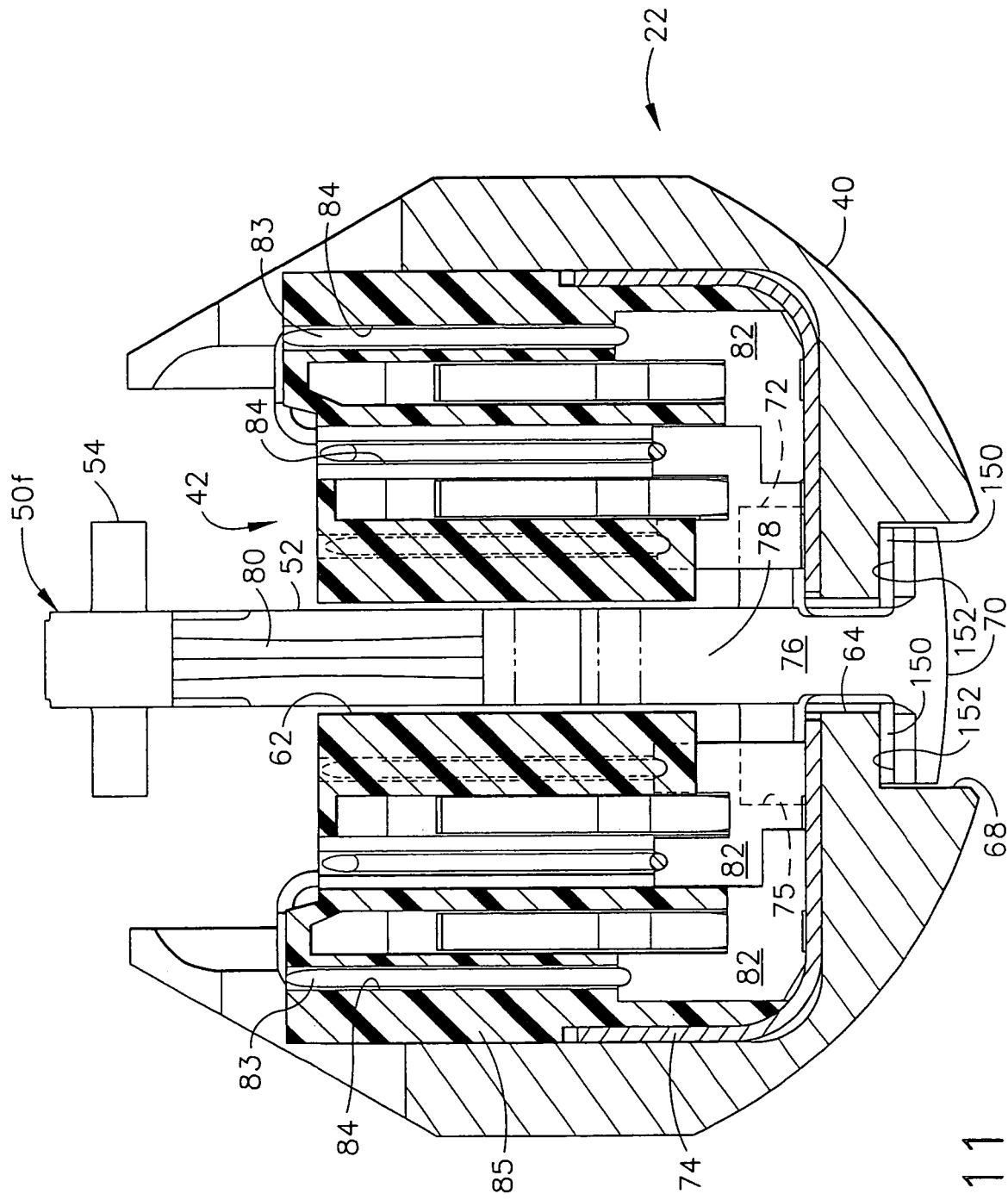
FIG. 11 is a front view in elevation taken in vertical and transverse cross section through the padded lower foot of the end effector (staple applying assembly) of the surgical stapling and severing instrument of FIG. 1.

In FIGS. 2, 11, the narrow longitudinal anvil slot 58 (FIG. 2) communicates upwardly to a laterally widened longitudinal anvil channel 66 sized to slidingly receive the upper pin 54. The longitudinal channel slot 64 communicates downwardly to a laterally widened longitudinal channel track 68 that receives a lower foot 70, which is sized to slide therein and is attached at a bottom of the vertical portion 52 of the E-beam 50. A laterally widened middle pin 72 extending from the vertical portion 52 of the E-beam 50 is positioned to slide along a top surface of a bottom tray 74 of the staple cartridge 42, which in turn rests upon the elongate staple channel 40. A longitudinal firing recess 75 formed in the staple cartridge 42 above the bottom tray 74 is sized to allow the middle pin 72 to translate through the staple cartridge 42.

A distal driving surface 76 of the vertical portion 52 of the E-beam 50 is positioned to translate through the proximally open vertical slot 62 of the staple cartridge 42 and distally drive a wedge sled 78 proximally positioned in the staple cartridge 42. The vertical portion 52 of the E-beam 50 includes a cutting surface 80 along a distal edge above the distal driving surface 76 and below the upper pin 54 that severs the clamped tissue 46 simultaneously with this stapling.

With particular reference to FIG. 11, it should be appreciated that the wedge sled 78 drives upwardly staple drivers 82 that in turn drive upwardly staples 83 out of staple apertures 84 formed in a staple body 85 of the staple cartridge 42 to form against the undersurface 60 of the anvil 20 which is in confronting relationship relative to an upper surface 43 of staple cartridge 42 (FIG. 2).

In FIGS. 2, 11, advantageously, the illustrative spacing, denoted by arrow 86 (FIG. 2), between the upper pin 54 is compliantly biased toward a compressed state wherein 0.015 inches of compressed tissue 46 is contained in the staple applying assembly 16. However, a larger amount of compressed tissue 46 up to about 0.025 inches is allowed by an inherent flexure of the E-beam 50. Excessive flexure, of perhaps up to 0.030 inches, is avoided should the length of staples be insufficient to form with the additional height. It should be appreciated that these dimensions are illustrative for a staple height of 0.036 inches. The same would be true for each category of staple, however.

Figure 4:
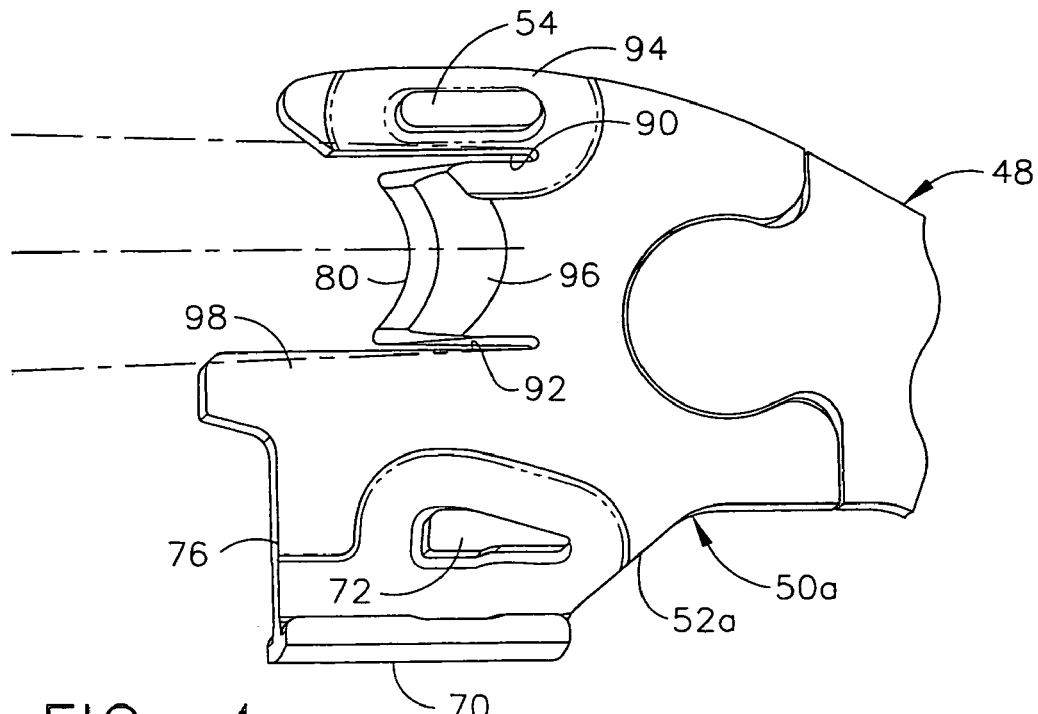
FIG. 4 is a left side view of a distal portion ("E-beam") of a first version of the force adjusted height firing bar of FIG. 2 having horizontal slits formed respectively between the top pin and cutting surface and between the middle pin and the cutting surface to enhance vertical flexure.

In FIG. 4. a first version of a compliant E-beam 50a includes top and bottom horizontal slits 90, 92 from a distal edge of the vertical portion 52a, perhaps formed by electro drilling machine (EDM). The vertical portion 52a thus contains a vertically compliant top distally projecting arm 94 containing the upper pin 54, a knife flange 96 containing the cutting surface 80, and a lower vertical portion 98 containing the distal driving surface 76, middle pin 72 and lower foot 70. The horizontal slits 90, 92 allow a compliant vertical spacing by allowing the top distally arm 94 to pivot upwardly to adjust to increased force from compressed tissue 46 (not shown).

Figure 5:
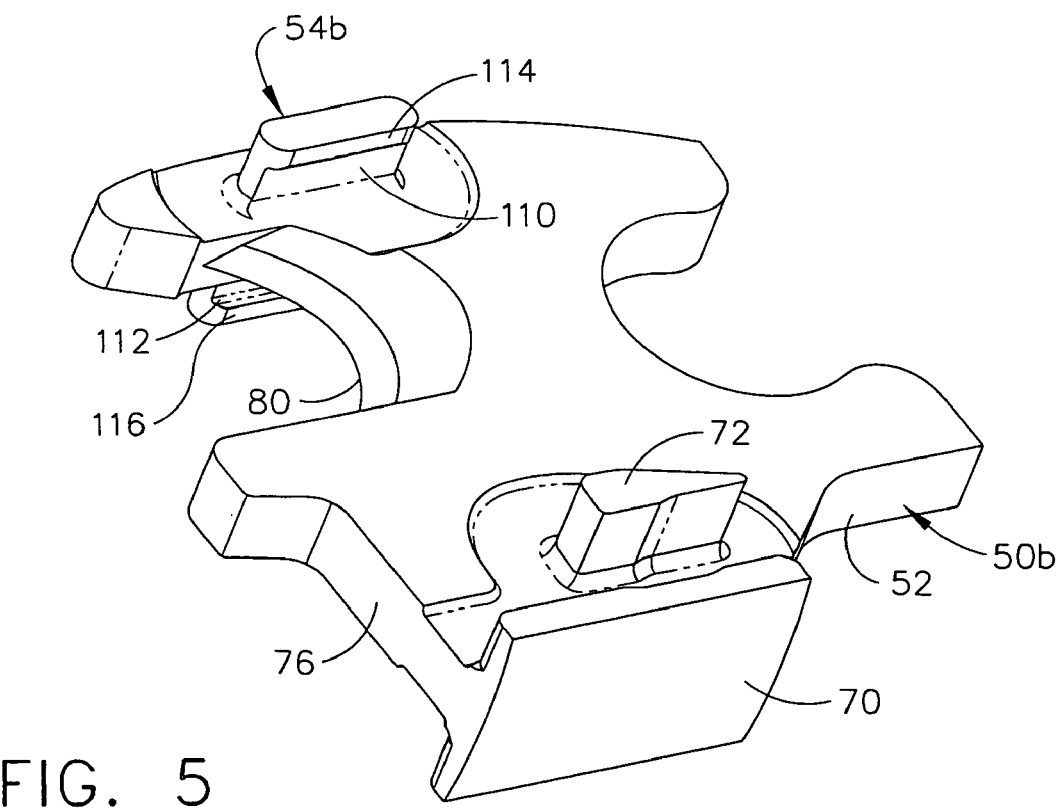
FIG. 5 is a lower left isometric view of a distal portion ("E-beam") of a second version of the force adjusted firing bar of FIG. 2 having a relieved lower area of an upper pin to enhance vertical flexure.
Figure 6:
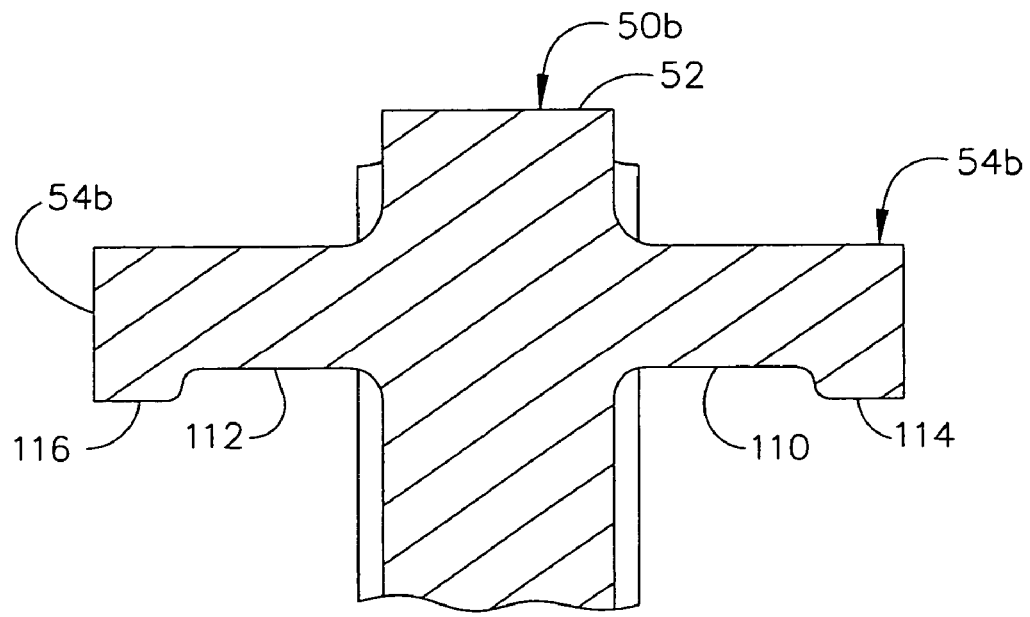
FIG. 6 is a front view in elevation of an upper portion of the E-beam of FIG. 5 taken in vertical and transverse cross section through the upper pin along lines 6-6.

In FIGS. 5-6, a second version of a compliant E-beam 50b includes left and right lower relieved areas 110, 112 formed into an upper pin 54b to each side of the vertical portion 52, leaving left and night lower bearing points 114, 116 respectively. The outboard position of the bearing points 114, 116 provides a long moment arm to exert the force to flex. It should be appreciated given the benefit of the present disclosure that the dimensions of the relieved areas 110, 112 and the choice of materials for the compliant E-beam 50b may be selected for a desired degree of flexure, given the staple size and other considerations.

Figure 7:
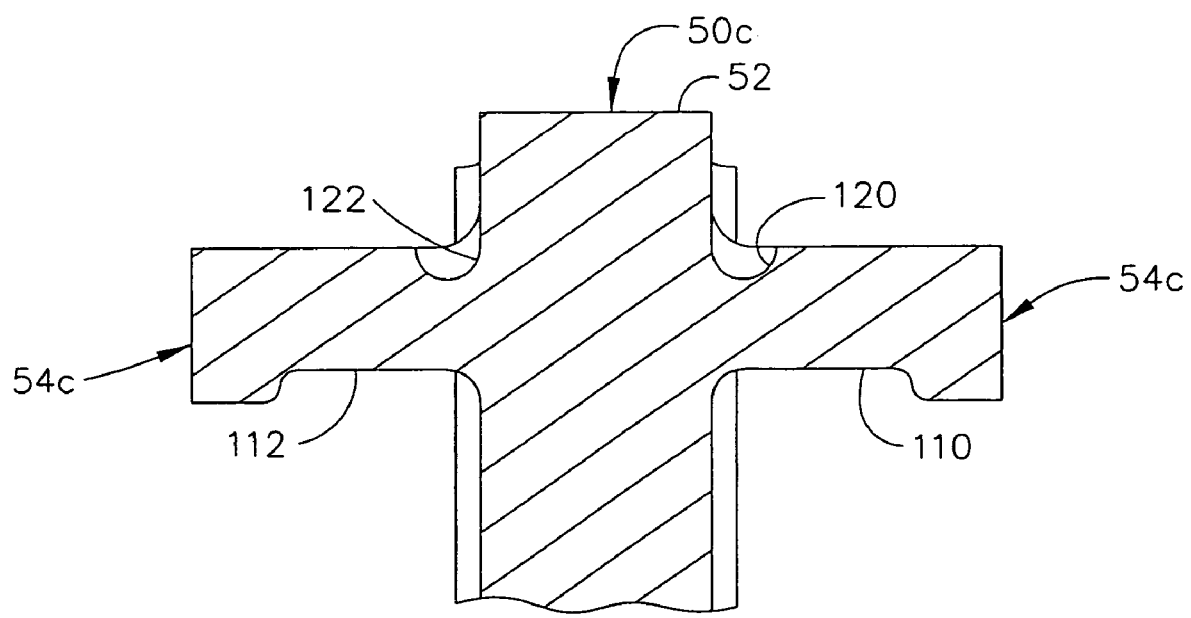
FIG. 7 is a front view of an upper portion of a third version of the E-beam of FIG. 5 taken in vertical and transverse cross section along lines 6-6 but further including relieved upper root attachments of the top pin for enhanced vertical flexure.

In FIG. 7, a third version of a compliant E-beam 50c is as described above in FIGS. 5-6 with further flexure provided by left and right upper narrow relieved areas 120, 122 formed into opposite top root surfaces of an upper pin 54c proximate to the vertical portion 52.

Figure 8:
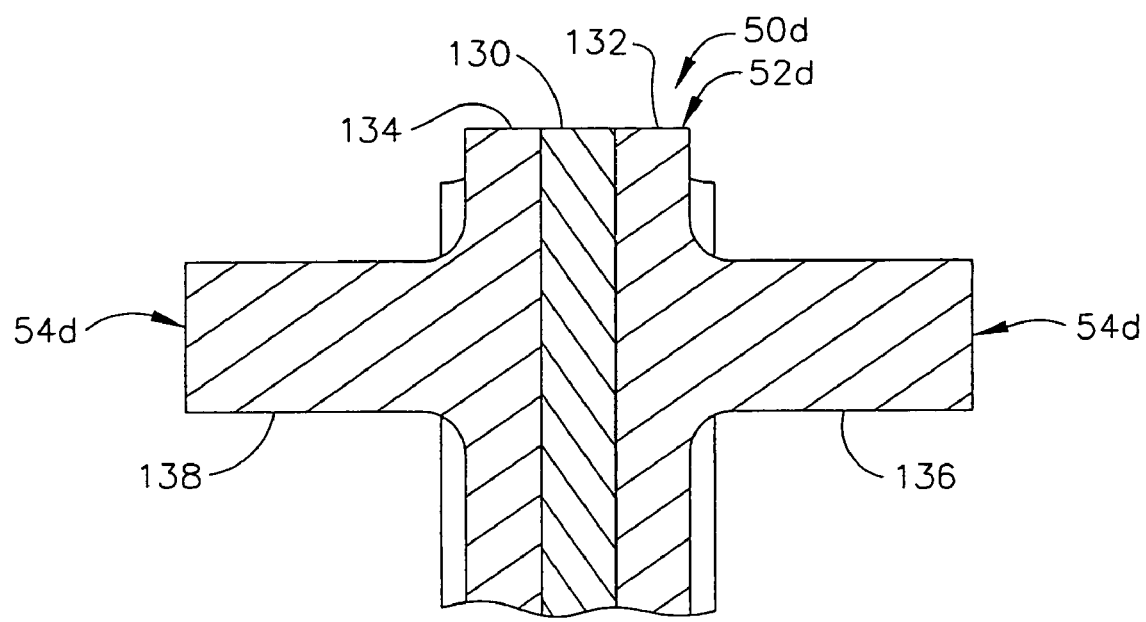
FIG. 8 is a front view of an upper portion of a fourth version of the E-beam of FIG. 5 taken in vertical and transverse cross section along lines 6-6 but including a resilient inner vertical laminate layer instead of a relieved undersurface of the top pin for enhanced vertical flexure.

In FIG. 8, a fourth version of a compliant E-beam 50d is as described for FIGS. 2-3 with an added feature of a composite/ laminate vertical portion 52d that includes a central resilient vertical layer 130 sandwiched between left and right vertical layers 132, 134 that support respectively left and right portions 136, 138 of an upper pin 54d. As the left and right portions 136, 138 are flexed either up or down, the resulting bowing of the left and right vertical layers 132, 134 are accommodated by a corresponding compression or expansion of the central resilient vertical layer 130.

Figure 9:
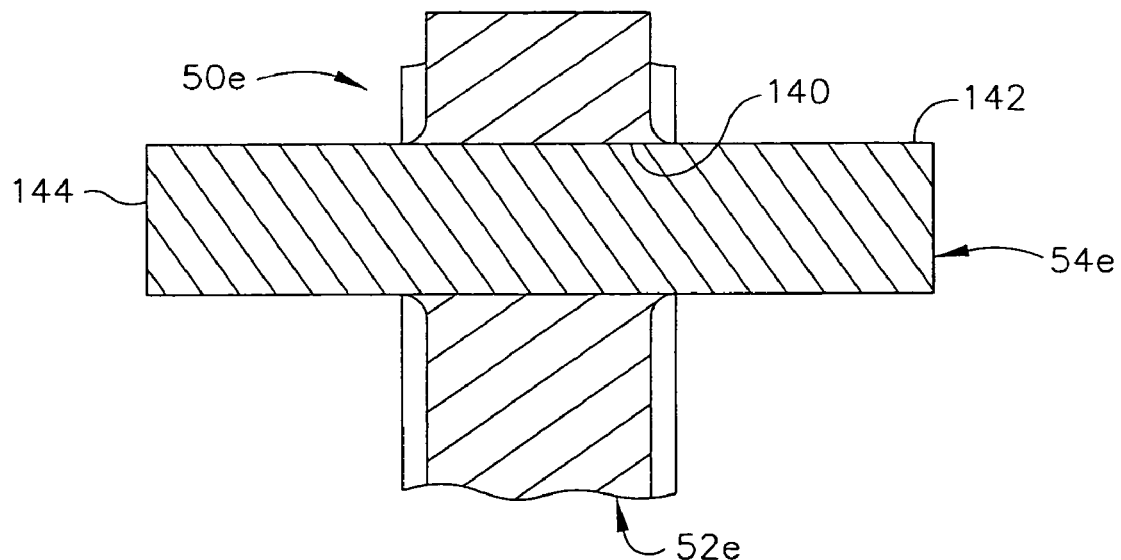
FIG. 9 is a front view of an upper portion of a fifth version of the E-beam of FIG. 5 taken in vertical and transverse cross section along lines 6-6 but including an upper pin formed of a resilient material instead of a relieved undersurface of the upper pin for enhanced vertical flexure.

In FIG. 9, a fifth version of a compliant E-beam 50e is as described for FIGS. 2-3 with an added feature of a discrete upper pin 54e formed of a more flexible material that is inserted through a horizontal aperture 140 through a vertical portion 52e. Thus, left and right outer ends 142, 144 of the discrete upper pin 54e flex in accordance with loading forces.

Figure 10:
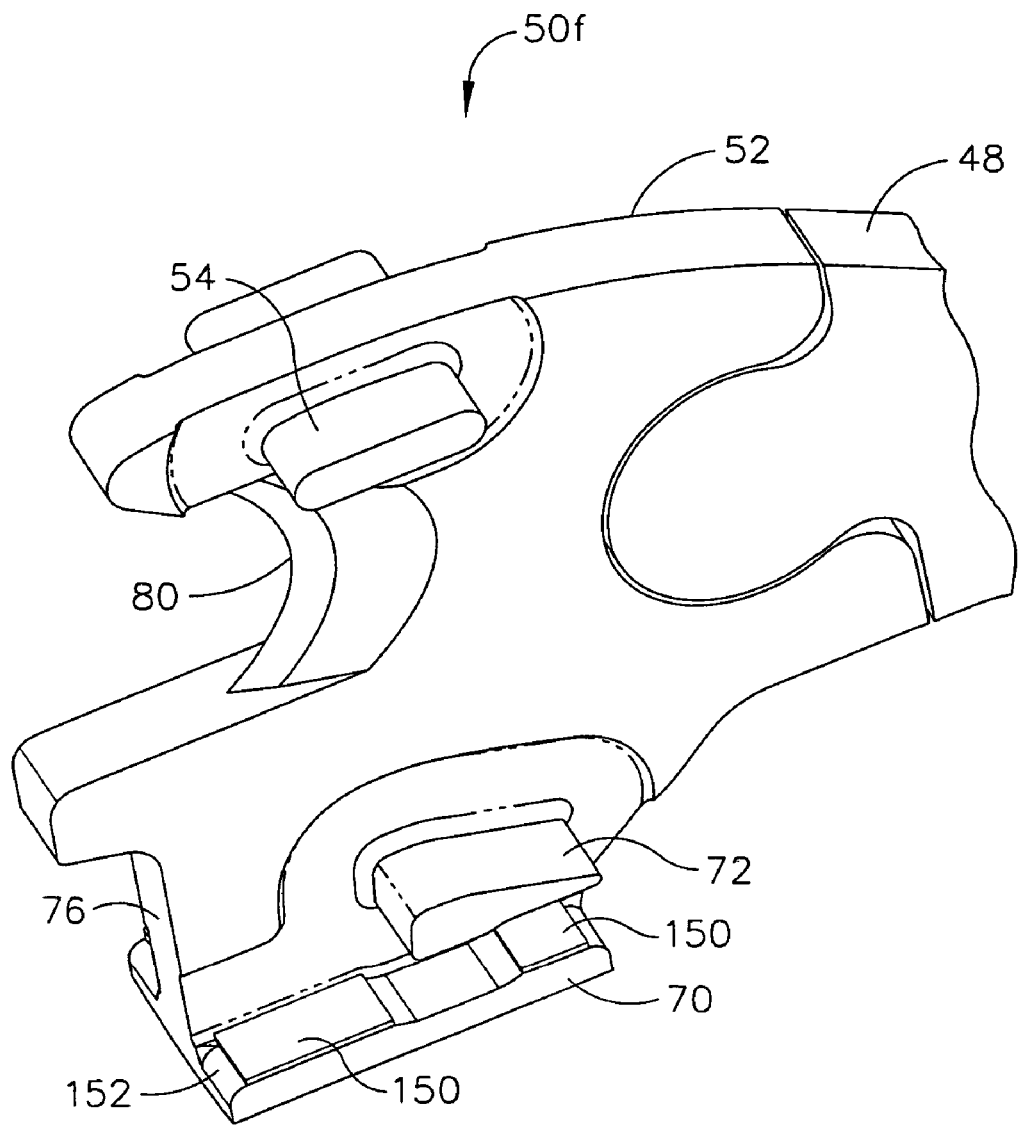
FIG. 10 is an upper left isometric view of a distal portion ("E-beam") of a sixth version of the force adjusted firing bar of FIG. 2 having resilient material upon a bottom foot to enhance vertical flexure.

Alternatively or in addition to incorporating flexure into an upper pin 54, in FIGS. 10-11, a sixth version of a compliant E-beam 50*f* as described for FIGS. 2-3 further includes resilient pads 150 that are attached to upper surfaces 152 of the bottom foot 70. The resilient pads 150 adjust the spacing of the upper pin 54 in accordance to the compression force experienced at the bottom foot 70.

Figure 12:
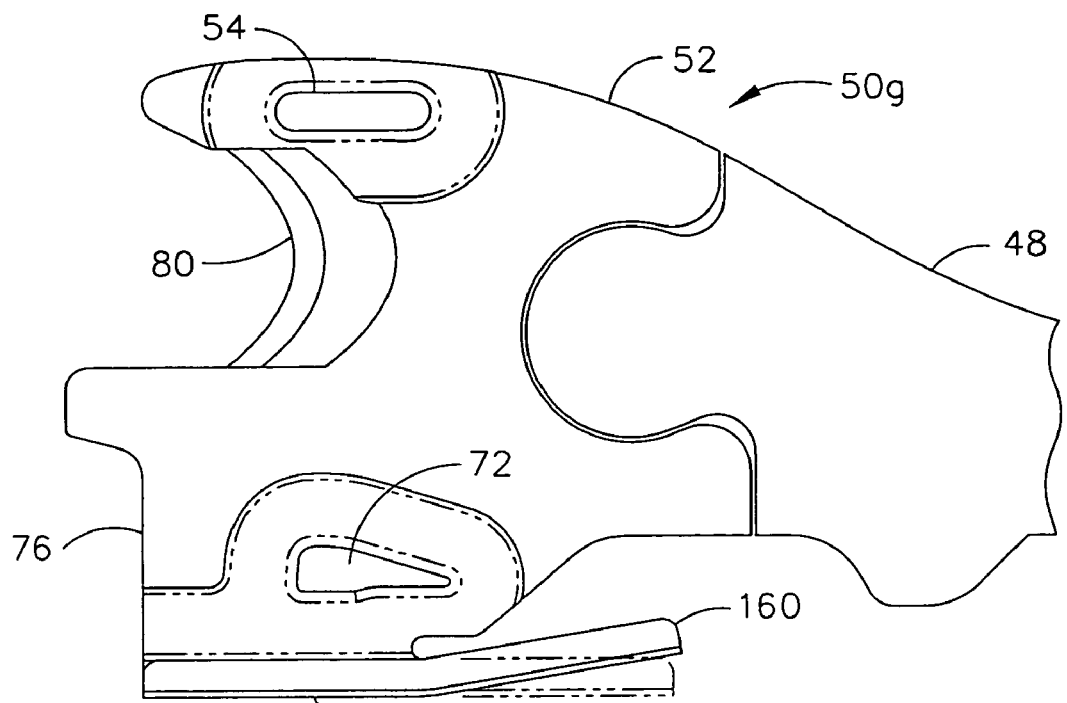
FIG. 12 is a left view in elevation of a distal portion ("E-beam") of a seventh version of the force adjusted firing bar of FIG. 2 having a proximally and upwardly extended spring arm attached to a lower foot to enhance vertical flexure.

In FIG. 12, a seventh version of a compliant E-beam 50*g* is as described above for FIGS. 2-3 with the added feature of a bottom foot (shoe) 70*g* having an upwardly aft extended spring finger 160 that resiliently urges the E-beam 50*g* downwardly to adjust vertical spacing in accordance with loading force.

Figure 13:
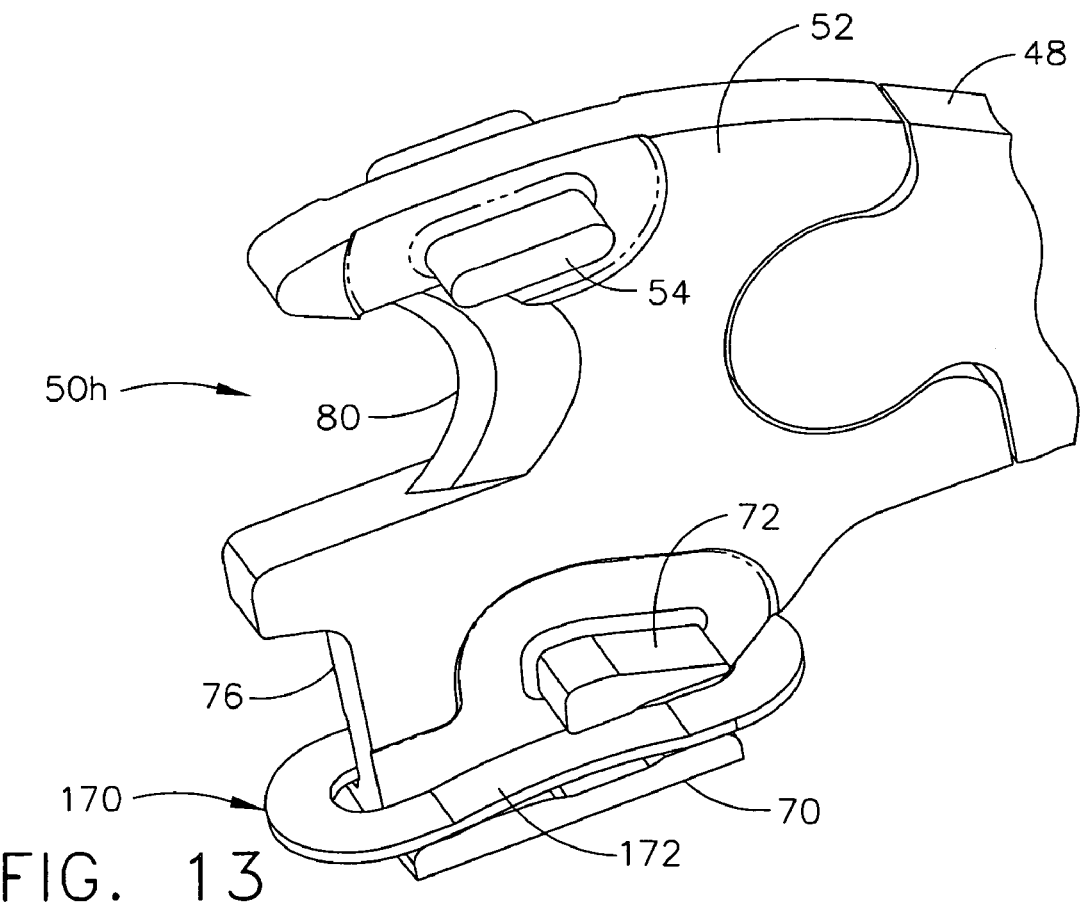
FIG. 13 is a left top isometric view of a distal portion ("E-beam") of an eighth version of the force adjusted firing bar of FIG. 2 having a spring washer encompassing a lower foot to enhance vertical flexure.

In FIG. 13, an eighth version of a compliant E-beam 50*h* is as described above in FIGS. 2-3 with the added feature of an oval spring washer 170 resting upon the bottom foot 70 encircling the vertical portion 52 and having an upwardly bowed central portion 172 that resiliently urges the E-beam 50*h* downwardly to adjust vertical spacing in accordance with loading force.

For another example, a compliant E-beam consistent with aspects of the present invention may include engagement to an anvil similar to the engagement in the illustrative versions of two structures that slide against opposite sides of the elongate staple channel. Similarly, a compliant E-beam may engage a lower jaw by having a laterally widened portion that slides internally within a channel formed in a lower jaw structure.

As yet an additional example, in the illustrative version, the staple cartridge 42 is replaceable so that the other portions of the staple applying assembly 16 may be reused. It should be appreciated given the benefit of the present disclosure that applications consistent with the present invention may include a larger disposable portion, such as a distal portion of an elongate shaft and the upper and lower jaws with a staple cartridge permanently engaged as part of the lower jaw.

As yet another example, the illustrative E-beam advantageously affirmatively spaces the upper and lower jaws from each other. Thus, the E-beam has inwardly engaging surfaces that pull the jaws together during firing in instances where a larger amount of compressed tissue tends to spread the jaws. Thereby the E-beam prevents malformation of staples due to exceeding their effective length. In addition, the E-beam has outwardly engaging surfaces that push the jaws apart during firing in stances where a small amount of tissue or other structure attributes of the instrument tend to pinch the jaws together that may result in staple malformation. Either or both functions may be enhanced by applications consistent with aspects of the invention wherein inherent flexure in the E-beam adjusts to force to allow a degree of closing of the jaws or of opening of the jaws.

Figure 14:
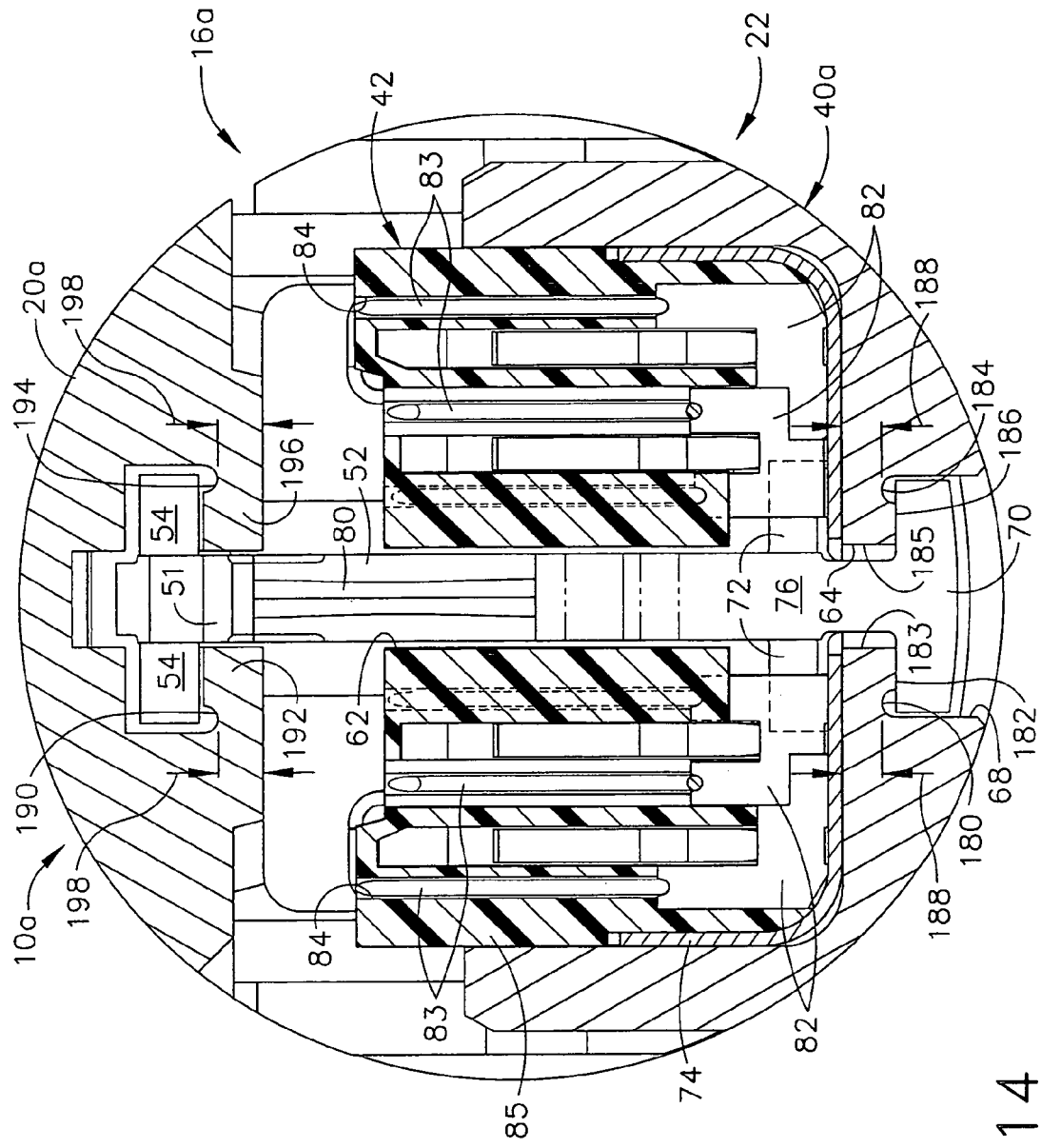
FIG. 14 is a cross-sectional end view of another staple applying assembly or end effector of the present invention in a clamped or closed position.
Figure 15:
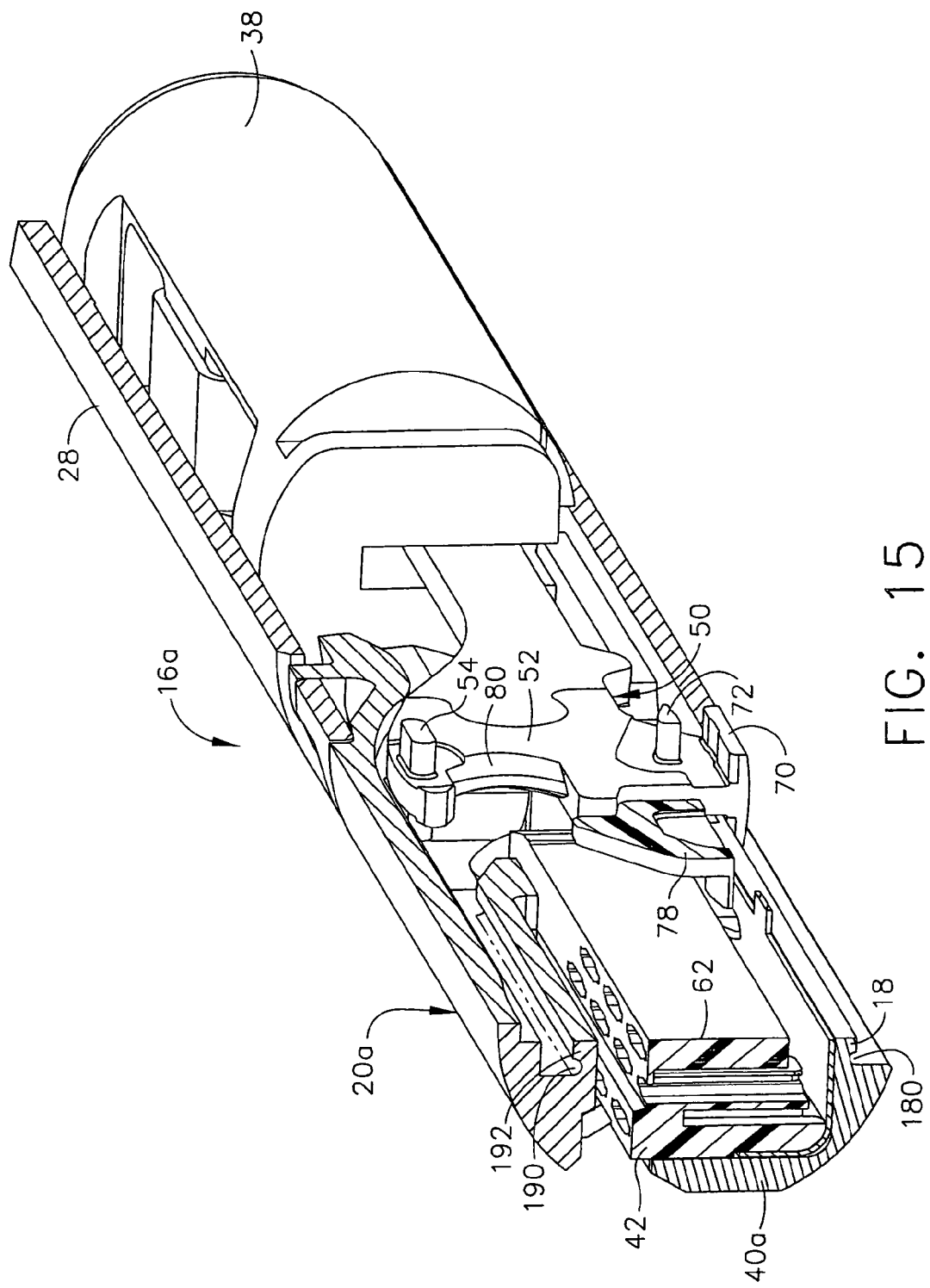
FIG. 15 is a partial perspective view of the staple applying assembly of FIG. 14 with some of the elements thereof shown in cross-section.

FIG. 14 is an end cross-sectional view of a surgical instrument 10*a* that has a staple applying assembly 16*a* of another embodiment of the present invention wherein like reference numerals are used to designate like elements and which employs an elongate channel 40*a* for supporting a staple cartridge 42 therein. In various embodiments, the channel 40*a* has resilient or flexible features configured to enable the staple applying assembly 40*a* to effectively accommodate different thicknesses of tissue. FIG. 15 is a partial perspective view of the staple applying assembly 16*a* with some components shown in cross-section for clarity. As can be seen in FIG. 14, in this embodiment, a first longitudinally extending relief area 180 and a second longitudinally extending relief area 184 are provided in the longitudinal channel 40*a*. The first longitudinally extending relief area 180 defines a first resilient or flexible channel ledge portion 182 and the second longitudinally extending relief area 184 defines a second resilient or flexible channel ledge portion 186. The elongate channel slot 64 through which the upper end 51 of the vertical portion 52 of the firing member in the form of E-beam 50 extends is formed between the free ends 183, 185 of the flexible ledges 182, 186, respectively. As can be further seen in FIG. 14, such arrangement permits the lower foot 70 of the E-beam 50 to bear upon the flexible ledge portions 182, 186 to accommodate differences in the thickness of the tissue clamped between the anvil 20 and the lower jaw 22 as the E-beam 50 transverses therethrough. It will be understood that the thickness 188 of the ledge portions 182, 186 may be selected to provided the desired amount of flexure to those portions of the elongate channel 40*a*. Also, the choice of materials for the elongate channel 40*a* may be selected for a desired degree of flexure, in view of the staple size and other considerations.

The elongate channel 40*a* as described above may be used in connection with a staple applying assembly that employs a conventional anvil 20. That is, the longitudinally extending anvil slot 58 may essentially have a "T" shape that is sized to accommodate the upper pins 54 and an upper end 51 of the vertical portion 52 of the E-beam 50. The embodiment depicted in FIGS. 14 and 15 employs and anvil 20*a* that has resilient or flexible features for further accommodating differences in tissue thicknesses clamped between the anvil 20*a* and the lower jaw 22. In particular, as can be seen in FIG. 14, a third longitudinally extending relief area 190 and a fourth longitudinally extending relief area 194 may be provided in the anvil 20*a* as shown. The third longitudinally extending relief area 190 defines a first anvil ledge portion 192 and the fourth longitudinally extending relief area 194 defines a second anvil ledge portion 196 upon which the upper pins 54 of the E-beam 50 may bear. Such arrangement provides a degree of flexure to the anvil 20*a* to accommodate differences in tissue thickness clamped between the anvil 20*a* and the lower jaw 22. It will be understood that the thickness 198 of the ledge portions 192, 196 may be selected to provided the desired amount of flexure to those portions of the anvil 20*a*. Also, the choice of materials for the anvil 20*a* may be selected for a desired degree of flexure, in view of the staple size and other considerations. Anvil 20*a* may be used in connection with the above-described channel arrangement as shown in FIGS. 14 and 15 or it may be employed with conventional channel arrangements without departing from the spirit and scope of the present invention.

The person of ordinary skill in the art will also appreciate that the anvil 20*a* and/or the channel 40*a* may be successfully employed with a conventional E-beam arrangement or any of the E-beam arrangements depicted herein. The E-beams disclosed herein may be reciprocatingly driven by control arrangements housed within the handle assembly. Examples of such control arrangements are disclosed in U.S. Pat. No. 6,978,921, issued Dec. 27, 2005, which has been herein incorporated by reference. Other known firing member configurations and control arrangements for applying firing and retraction forces or motions thereto could conceivably be employed without departing from the spirit and scope of the present invention.

Figure 16:
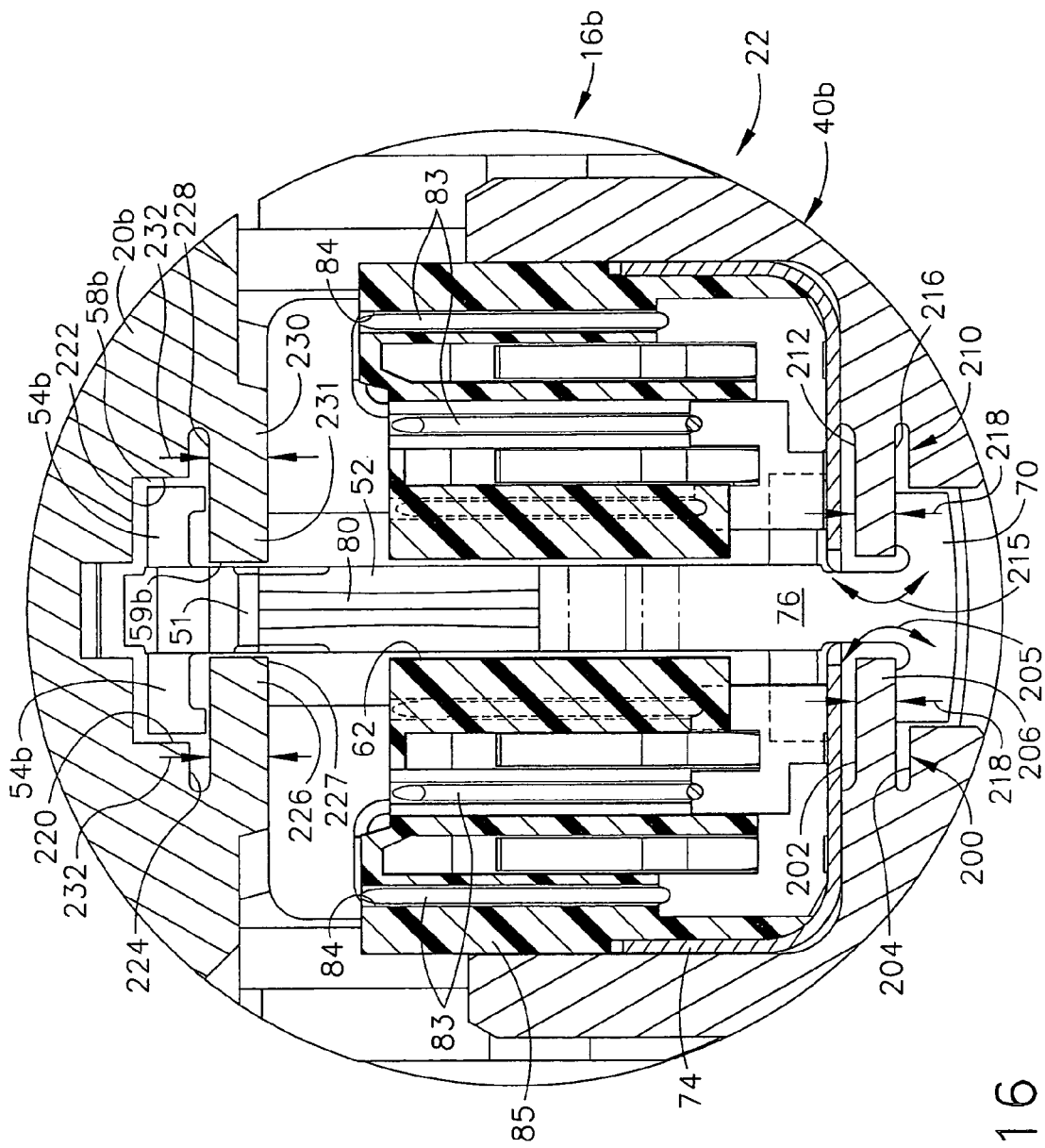
FIG. 16 is a cross-sectional end view of another staple applying assembly or end effector of the present invention in a clamped or closed position.
Figure 17:
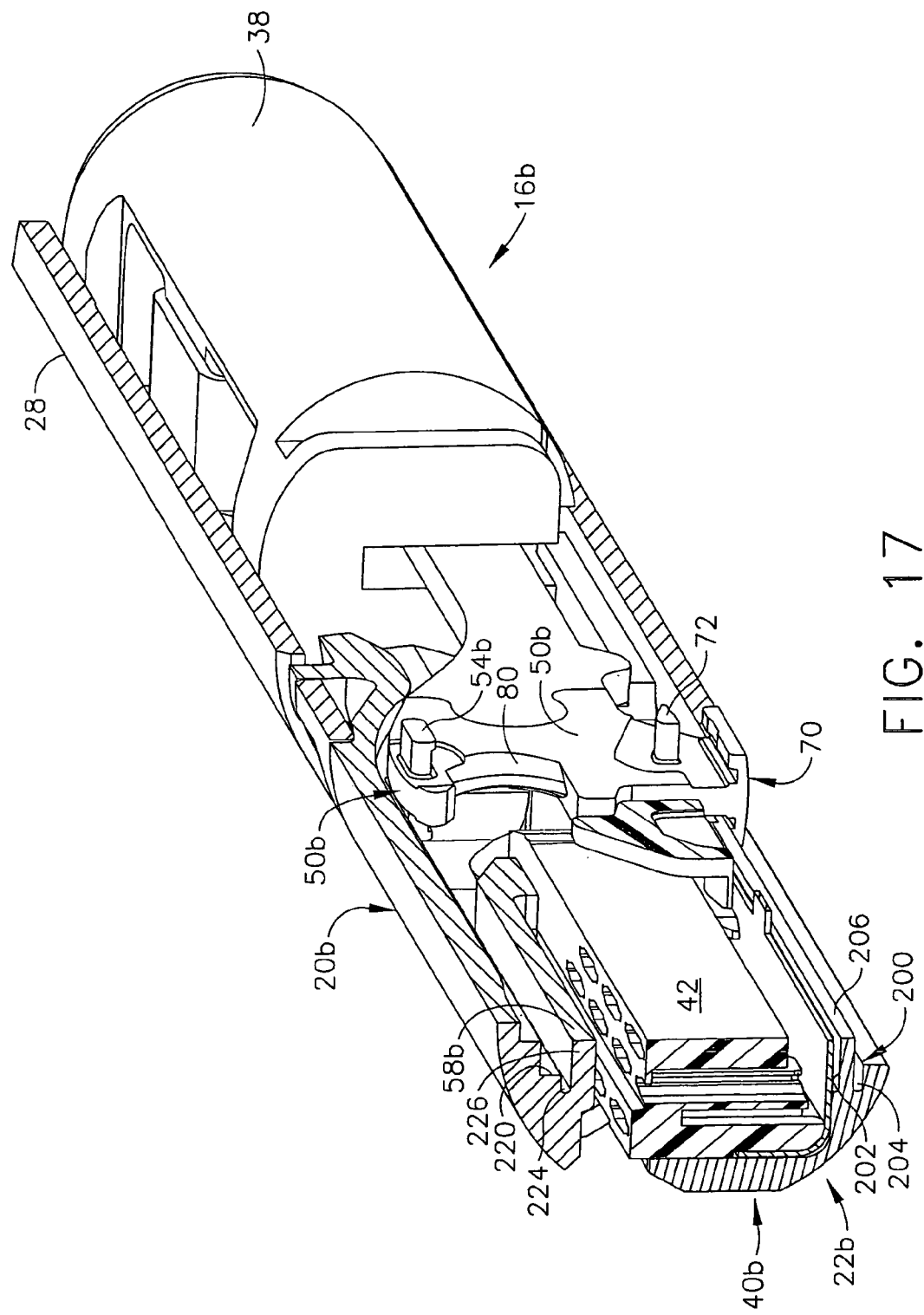
FIG. 17 is a partial perspective view of the staple applying assembly of FIG. 16 with some of the elements thereof shown in cross-section.

FIGS. 16 and 17 illustrate a staple applying assembly 16*b* that employs another version of a channel 40*b* and an anvil 20*b* that each have resilient or flexible portions to accommodate differences in tissue thicknesses clamped between the anvil 20*b* and the lower jaw 22*b*. As can be seen in those Figures, a first pair 200 of upper and lower longitudinally extending relieved or undercut areas 202, 204 are provided in the channel 40*b* to define a first cantilever-type support ledge 206 and a second pair 210 of relieved or undercut areas 212, 214 are provided in the channel 40b to define a second cantilever-type support ledge 216. The first pair relieved areas 202, 204 provide a degree of flexure to the first support ledge 206 to enable it to flex as illustrated by arrow 205. Likewise, the second pair 210 of relieved areas 212, 214 provide a degree of flexure to the second support ledge 216 to enable it to flex as illustrated by arrow 215. As with the above described embodiments, the thickness 208 of the support ledges 206 and 216 may be selected to provided the desired amount of flexure to those portions of the elongate channel 40b to accommodate different thicknesses of tissue. Also, the choice of materials for the elongate channel 40b may be selected for a desired degree of flexure, in view of the staple size and other considerations.

FIGS. 16 and 17 further illustrate an anvil 20b that has a T-shaped slot 58b that defines a first lateral wall portion 220 and a second lateral wall portion 222. In various embodiments, a first longitudinally extending undercut area 224 is provided in the first lateral wall portion 220 to define a resilient or flexible first ledge 226. Similarly, in various embodiments, a second longitudinally extending undercut area 228 is provided in the second lateral wall portion 222 to define a resilient or flexible second ledge 230. As can be seen in FIG. 16, the ends 227, 231 of the first and second ledges 226, 230, respectively serve to define a portion 59b of anvil sot 58b through which an upper end portion 51 of E-beam 50b extends. Such arrangement permits the upper pins 54b of the E-beam 50b may bear upon the first resilient ledge 226 and the second resilient ledge 230 to provide a degree of flexure to the anvil 20ab to accommodate differences in tissue thickness clamped between the anvil 20b and the lower jaw 22b. It will be understood that the thickness 232 of the ledges 226, 230 may be selected to provided the anvil 20b with a desired amount of flexure to accommodate different tissue thicknesses. Also, the choice of materials for the anvil 20b may be selected for a desired degree of flexure, in view of the staple size and other considerations. Anvil 20b may be used in connection with the above-described channel 40b shown in FIGS. 16 and 17 or it may be employed with a conventional channel arrangement. The skilled artisan will also appreciate that the anvil 20a and/or the channel 40bg may be successfully employed with a conventional E-beam arrangement or any of the E-beams described herein.

Figure 18:
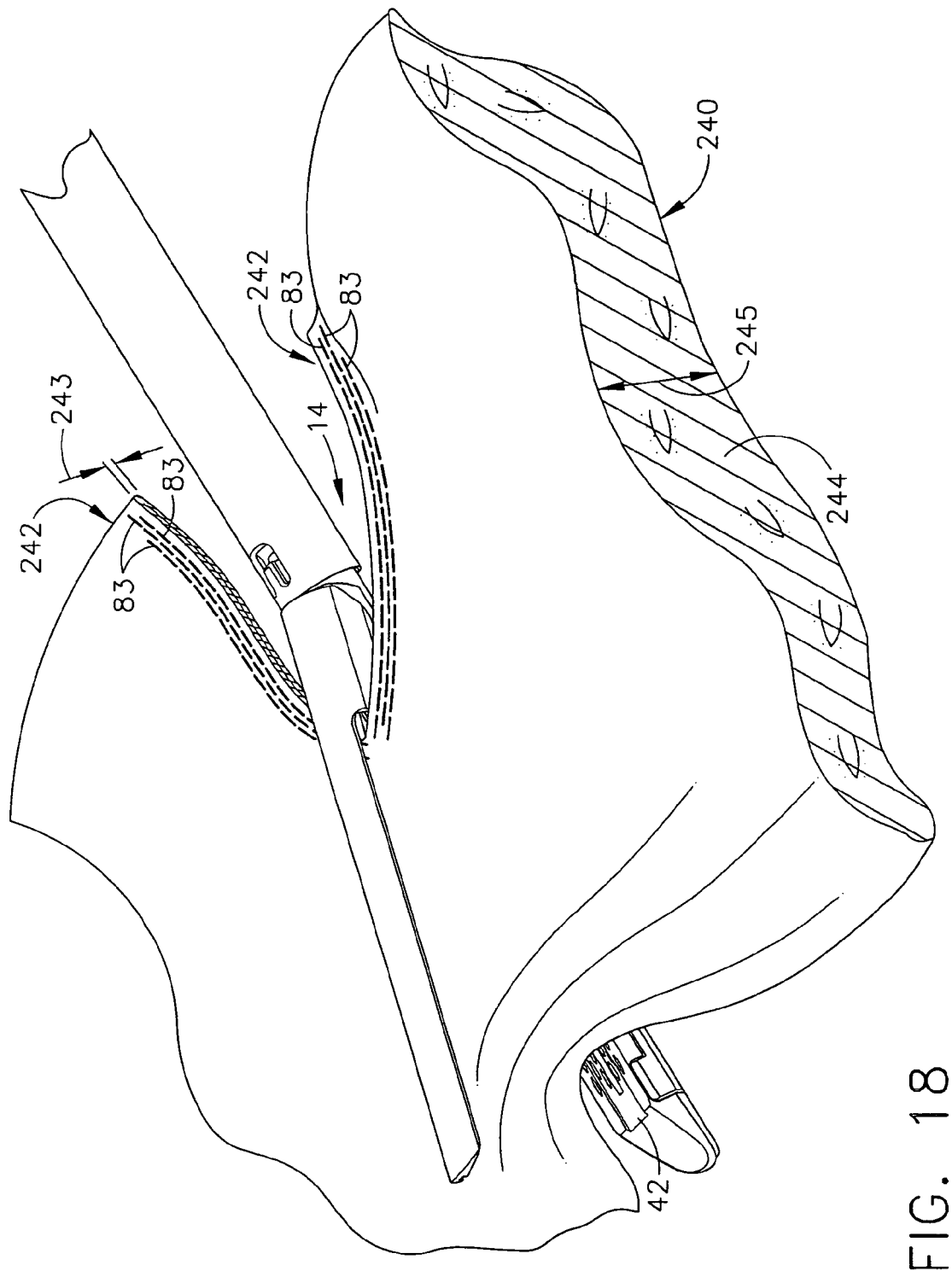
FIG. 18 is a partial perspective of a staple applying assembly of the present invention clamping a piece of tissue that has been partially cut and stapled.

FIG. 18 illustrates the cutting and stapling of tissue 240 with any one of the various surgical cutting and stapling instrument embodiments of the present invention. A portion 242 of the tissue 240 illustrated in FIG. 18 has already been cut and stapled. After the clinician has cut and stapled the first portion 242, the instrument would be withdrawn to enable new staple cartridge 42 to be installed. FIG. 18 illustrates the position of the implement portion 14 prior to commencing the second cutting and stapling process. As can be seen in that Figure, the portion 242 of the tissue 240 that has been stapled has a thickness 243 that is less than the thickness 245 of other portions 244 of the tissue 240.

Figure 19:
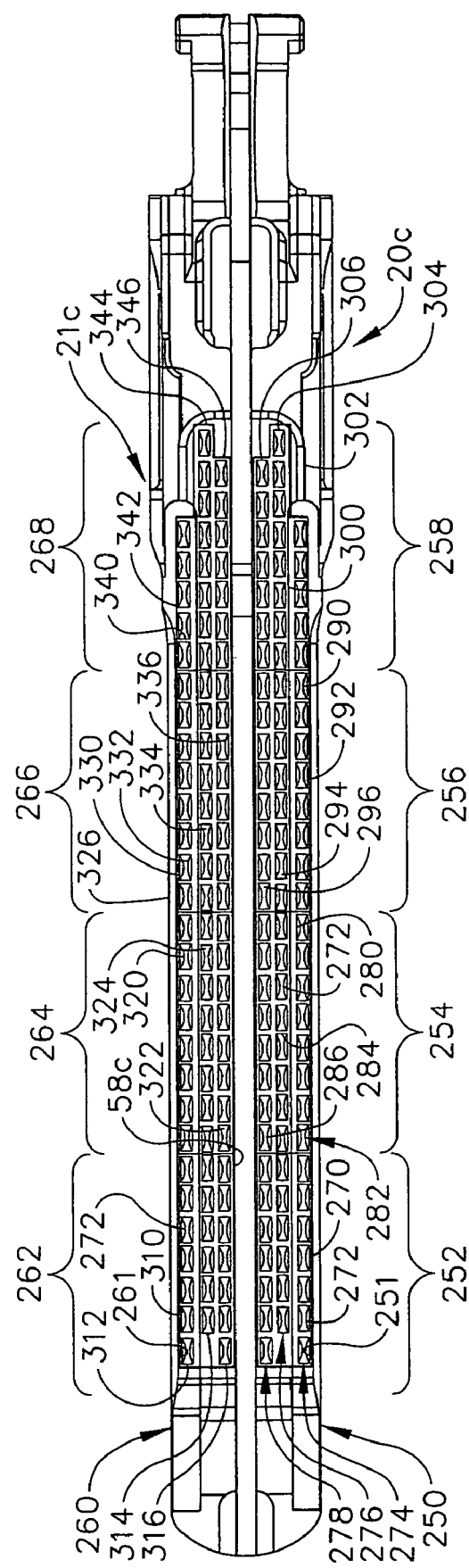
FIG. 19 is a bottom view of an anvil embodiment of the present invention.
Figure 20:
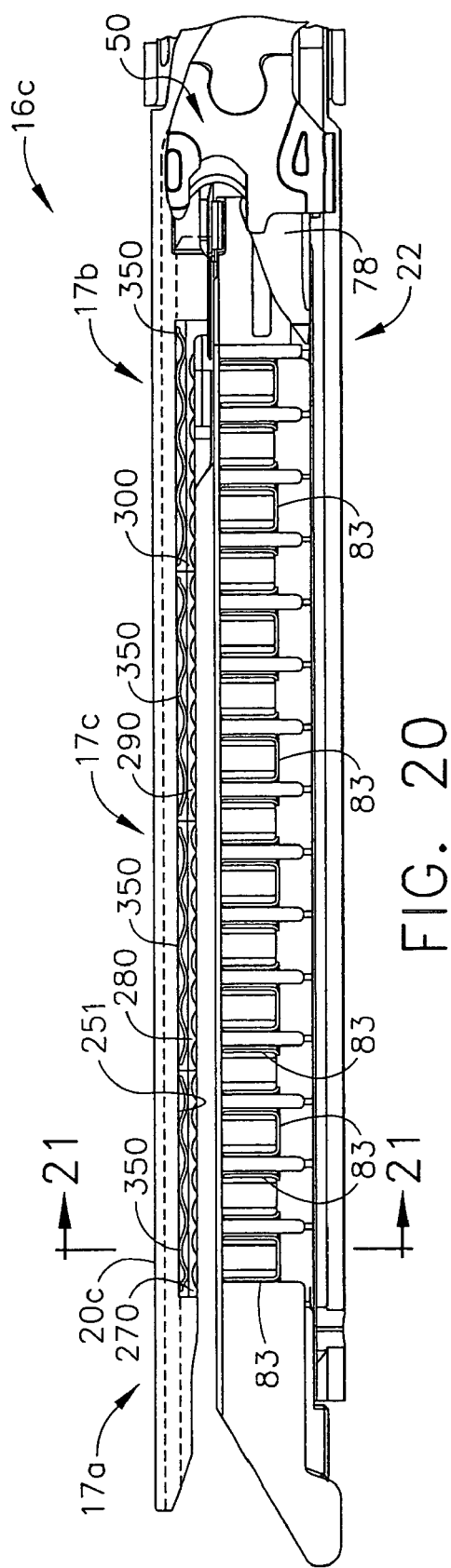
FIG. 20 is a longitudinal cross-sectional view of a staple applying assembly employing the anvil embodiment depicted in FIG. 19.

FIG. 19 is a view of the underside of an anvil 20c that may be employed with a staple applying assembly 16c of various embodiments of the present invention. The anvil 20c includes and anvil body 21c that supports movable staple forming pockets that define different staple zones. In the embodiment depicted in FIG. 19, four left staple zones 252, 254, 256, 258 are provided on a left side 250 of the anvil slot 58c and four right staple zones 262, 264, 266, 268 are provided on a right side 260 of the anvil slot 58c within the anvil body 21c. The first left staple zone 252 is defined by a first left staple forming insert member 270 that has a series of staple forming pockets 272 therein. In this embodiment, three rows 274, 276, 278 of staple forming pockets 272 are provided in the insert 270. As can be seen in FIG. 19, the central row 276 of pockets 272 are slightly longitudinally offset from the outer two rows 274, 278 of pockets 272 and correspond to the arrangement of the corresponding staple apertures 84 in corresponding staple cartridges 42. Those of ordinary skill in the art will appreciate that such arrangement serves to result in the application of the staples 83 in a staggered manner as illustrated in FIG. 18.

Similarly, the second left staple zone 254 may be defined by a second left staple forming insert 280 that may have three rows 282, 284, 286 of staple forming pockets 272 therein. The third left staple zone 256 may be defined by a third left staple forming insert 290 that may have three rows 292, 294, 296 of staple forming pockets 272 therein. The fourth left staple zone 258 may be defined by a fourth left staple forming insert 300 that may have three rows 302, 304, 306 of staple forming pockets 272 therein. The first, second, third and fourth left staple forming inserts 270, 280, 290, 300 are longitudinally aligned in a left side cavity 251 provided in the anvil 20c on the left side 250 of the anvil slot 58.

The first right staple zone 262 may be defined by a first right staple forming insert member 310 that has a series of staple forming pockets 272 therein. In this embodiment, three rows 312, 314, 316 of staple forming pockets 272 are provided in the insert 310. As can be seen in FIG. 19, the central row 314 of staple forming pockets 272 are slightly longitudinally offset from the outer two rows 312, 316 and correspond to the arrangement of the corresponding staple apertures 84 in corresponding staple cartridges 42. Such arrangement serves to result in the application of the staples 83 in a staggered manner on the right side of the tissue cut line. The second right staple zone 264 may be defined by a second right insert 320 that may have three rows 322, 324, 326 of staple forming pockets 272 therein. The third right staple zone 266 may be defined by a third right staple forming insert 330 that may have three rows 332, 334, 336 of staple forming pockets 272 therein. The fourth right staple zone 268 may be defined by a fourth right staple forming insert 340 that may have three rows 342, 344, 346 of staple forming pockets 272 therein. The first, second, third, and fourth right staple forming inserts 310, 320, 33, 340 are longitudinally aligned in a right side cavity 261 provided in the anvil 20c on the right side 260 of the anvil slot 58. In various embodiments, the staple forming inserts may be fabricated from stainless steel or other suitable materials that are harder than the material from which the staples are fabricated. For example, the inserts may be successfully fabricated from other materials such as cobault chromium, aluminum, 17-4 stainless steel, 300 series stainless steel, 400 series stainless steel, other precipitant hardened stainless steels, etc.

Figure 22:
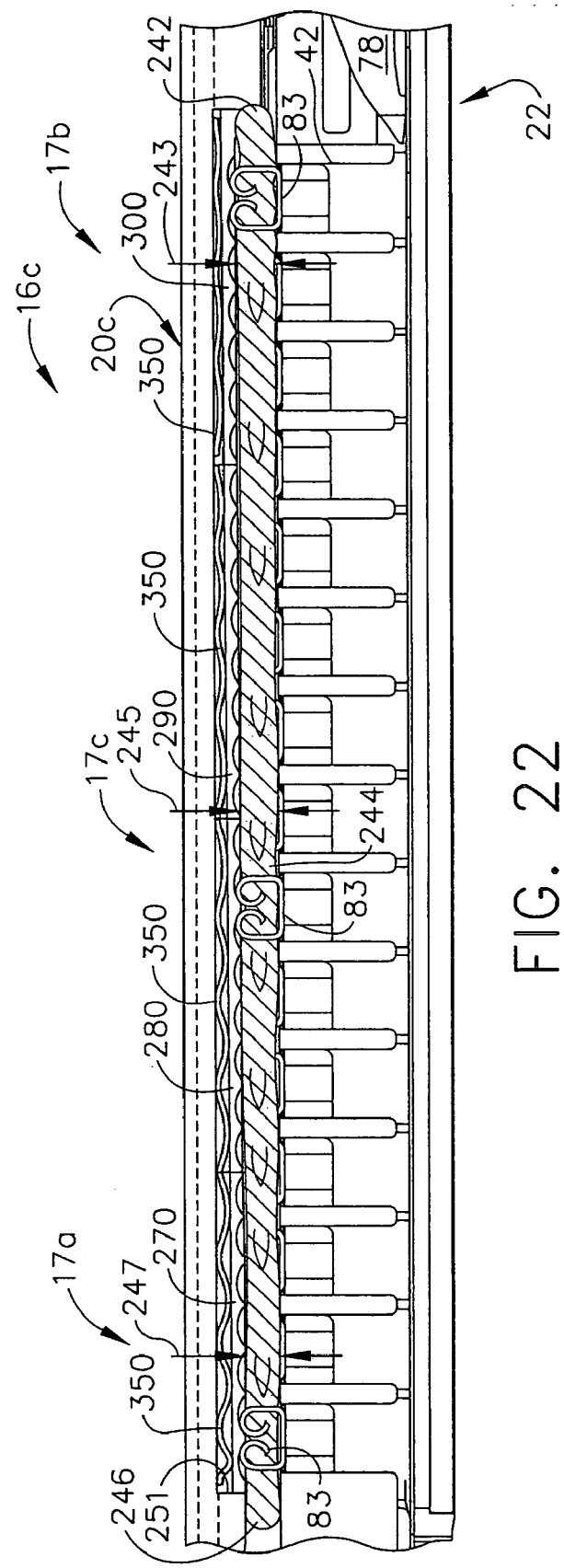
FIG. 22 is another longitudinal cross-sectional view of the staple applying assembly of FIGS. 20 and 21 clamping a piece of tissue therein, wherein the tissue has varying cross-sectional thicknesses.
Figure 21:
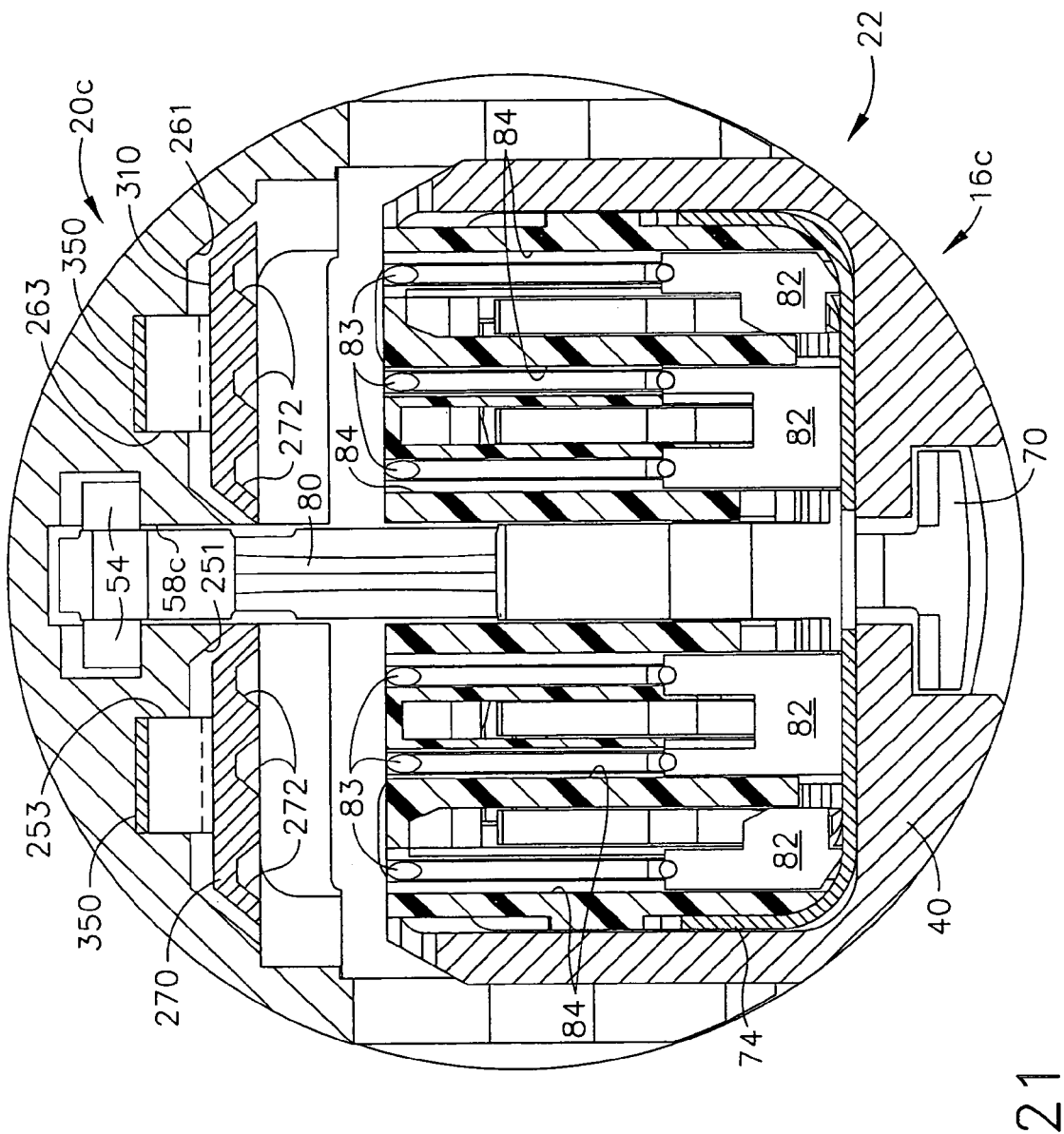
FIG. 21 is a cross-sectional end view of the staple applying assembly of FIG. 20 taken along line 21-21 in FIG. 20, with some elements shown in solid form for clarity.

At least one biasing member or compliant member in the form of a wave spring 350 or other suitable biasing or compliant medium or member corresponding to each of the staple forming inserts 270, 280, 290, 300, 310, 320, 330, 340 is provided between the respective left staple forming inserts 270, 280, 290, 300 and the bottom of the left side cavity 251 as shown in FIGS. 20-23. Wave springs 350 or other suitable biasing or compliant medium or member is also provided between each of the right staple forming inserts 310, 320, 330, 340 and the bottom surface of the right side cavity 261. The wave springs 350 on the left side of the anvil slot 58c may be received in a corresponding spring cavity 253 and the wave springs 350 on the right side of the anvil cavity 58c may be received in a corresponding spring cavity 263. To biasingly retain each insert 270, 280, 290, 300, 310, 320, 330, 340 in the anvil 20c, each insert 270, 280, 290, 300, 310, 320, 330, 340 may be attached to its corresponding spring 350 or biasing member by, for example, adhesive or other fastener arrangements. In addition, each spring 350 may be attached to the anvil 20c by, for example, adhesive or other mechanical fastener arrangements to retain a portion of the wave spring 350 within its respective spring cavity 253 or 263. Such spring/biasing member arrangements serve to bias the inserts 270, 280, 290, 300, 310, 320, 330, 340 toward the tissue 240 and staples and essentially act as resilient "shock absorbers" to accommodate differences in tissue thicknesses. This advantage is illustrated in FIGS. 22-24.

In particular, as can be seen in FIG. 22, the portion 242 of the tissue 240 clamped in the proximal end 17b of the staple applying assembly 16c has a first thickness (arrow 243 that is thicker than the thickness (arrow 245) of the portion 244 of tissue 240 clamped in the central portion 17c of the staple applying assembly 16c. The thickness 245 of tissue portion 244 is greater than the thickness (arrow 247) of the portion 246 of tissue 240 that is clamped in the distal end 17a of the staple applying assembly 16c. Thus, the staples 83 formed in the distal portion 17a of the staple applying assembly 16c are more tightly formed that the staples 83 formed in the central portion 17c of the staple applying assembly 16c which are more tightly formed than those staples 83 formed in the proximal end 17b of the staple applying assembly 16c due to the differences in tissue thicknesses. FIG. 23 further illustrates the variations in staple formation heights based upon the variations in the thicknesses of the tissue clamped within the staple applying assembly 16c. FIG. 24 illustrates a condition wherein the tissue 240 clamped in the central portion 17c of the staple applying assembly 16c is thicker than the portions of tissue clamped in the distal and proximal ends of the staple applying assembly 16c. Thus, the formation heights of the staples in the central portion 17c will be higher than the staple formation heights of the staples associated with the proximal end 17b and distal end 17a of the staple applying assembly 16c.

Figure 25:
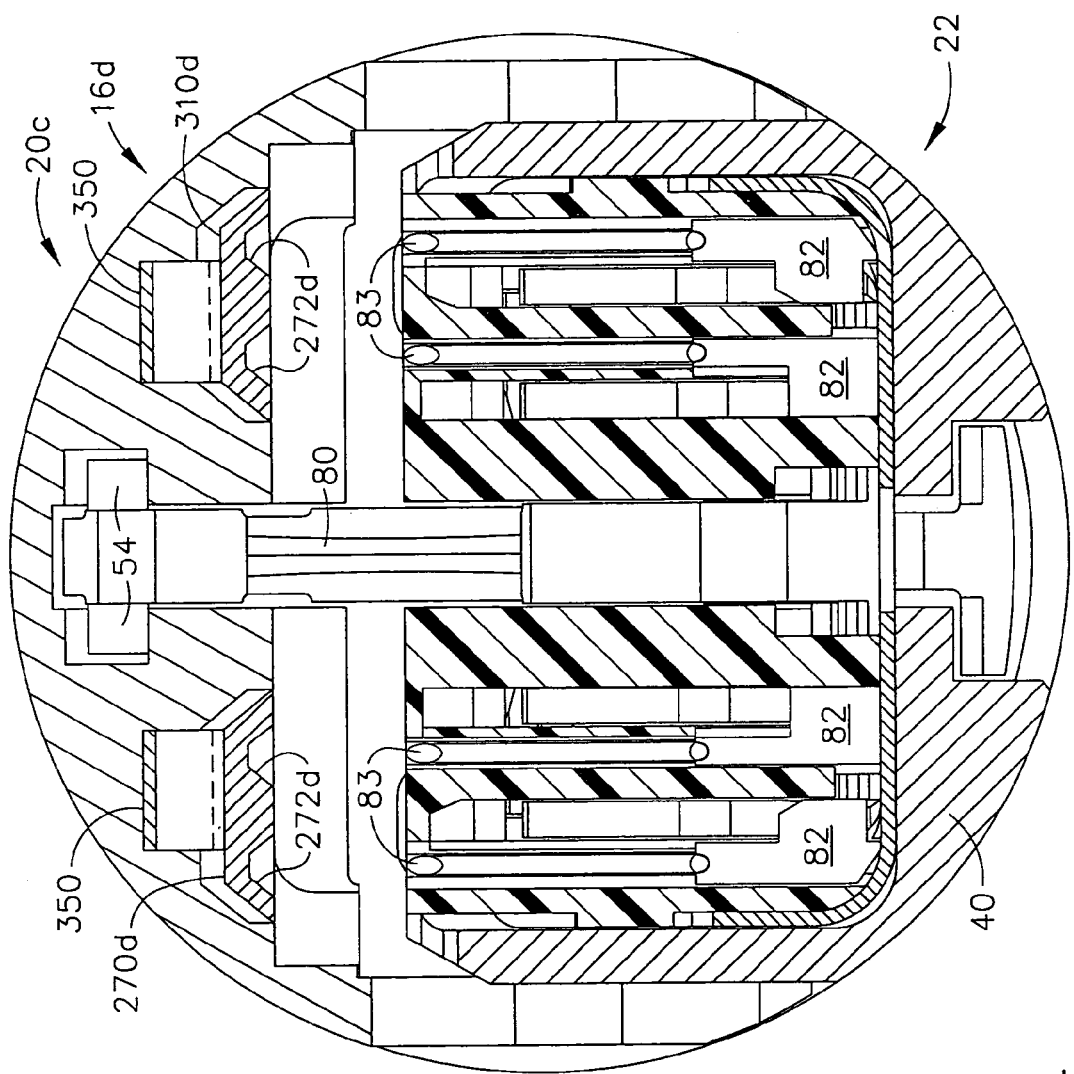
FIG. 25 is an end cross-sectional view of another staple applying assembly of the present invention in a clamped position.

Those of ordinary skill in the art will understand that the unique and novel features of the embodiments depicted in FIGS. 19-24 may also be employed in connection with a staple applying assembly that is essentially identical in construction and operation to staple applying assembly 16c described above, except that the staple forming inserts 270, 280, 290, 300, 310, 320, 330, 340 may have just one row of staple formation pockets 272 therein or two rows of staple formation pockets 272 therein. For example, FIG. 25 illustrates an embodiment that only applies two rows of staples on each side of the tissue cut line. Shown in that Figure are staple forming inserts 270d and 310d that only have two rows of staple forming pockets 272d each.

Figure 26:
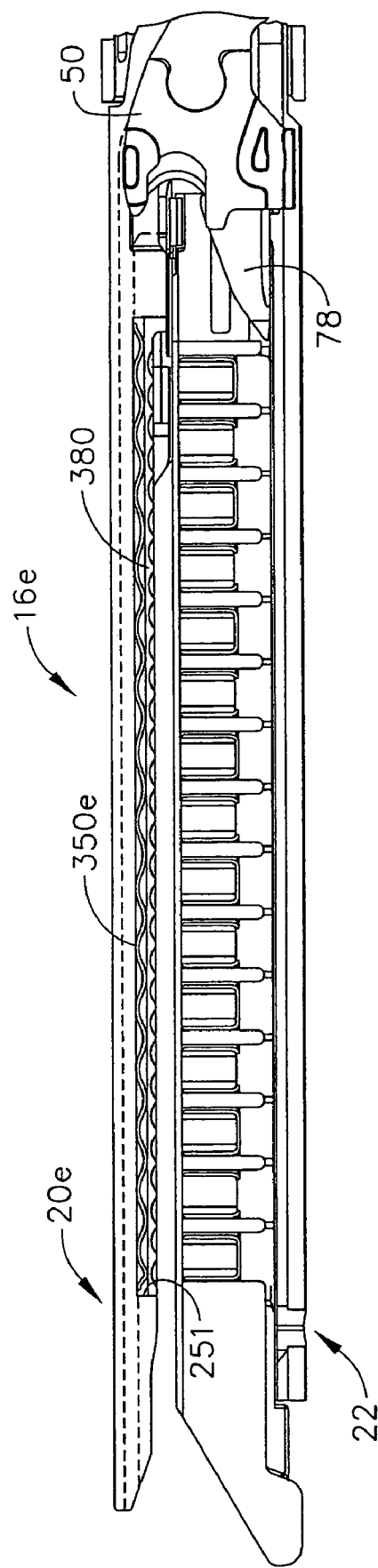
FIG. 26 is longitudinal cross-sectional view of another staple applying assembly of the present invention.

The skilled artisan will further understand that the number of staple forming inserts employed on each side of the anvil slot 58 may vary. For example a single longitudinally extending insert may be used on each side of the anvil slot 58. FIG. 26 illustrates another staple applying assembly 16e of the present invention that only employs one staple forming insert on each side of the anvil slot. FIG. 26 depicts a cross-sectional view of the left side of an anvil 20e that supports a single left staple forming insert 380 that is attached to a single wave spring 350e. Other biasing members or multiple wave springs or biasing members may also be employed. The biasing member or members 350e are supported in the left side cavity 251e and attached to the anvil 20e in one of the various manners described above. A similar rights side insert (not shown) would be employed on the right side of the anvil slot 58. Furthermore, although FIGS. 19-24 depict use of four staple forming inserts on each side of the anvil slot greater numbers of staple forming inserts may be employed.

Figure 27:
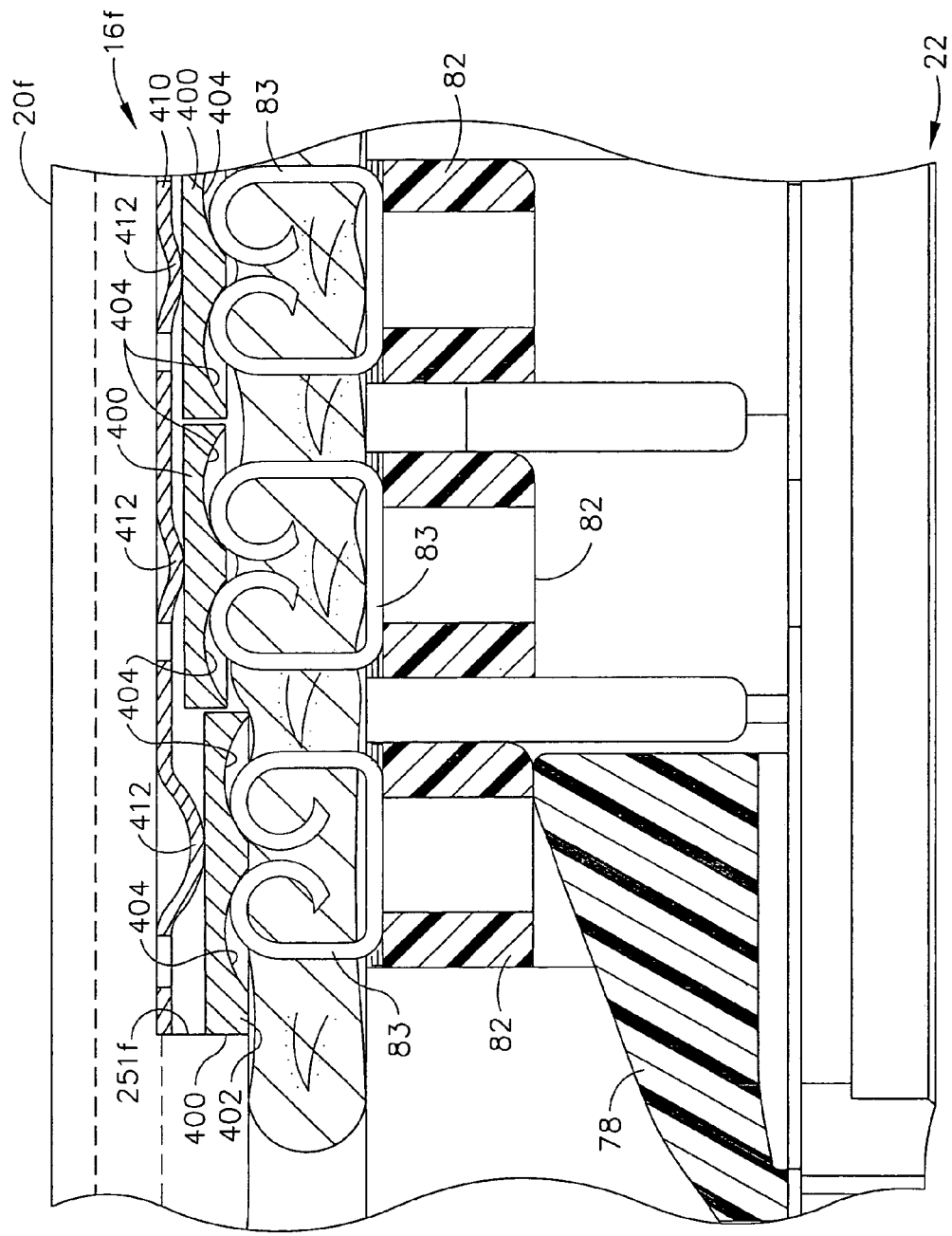
FIG. 27 is a cross-sectional view of a portion of another staple applying assembly of the present invention with a piece of tissue clamped and stapled therein.

FIGS. 27-29 illustrate another staple applying assembly 16f of the present invention wherein a separate movable staple forming insert is provided for each staple 83. In particular, as can be seen in FIG. 27, a single staple forming insert 400 is provided for each staple 83. Each staple forming insert 400 may have staple forming pockets 404 formed on its underside 402 thereof for forming the ends of the corresponding staple 83. As with various embodiment described above, each insert 400 has a biasing member 412 associated therewith. In the example depicted in FIGS. 27-29, the biasing members 412 comprise stamped portions of a biasing plate 410. The biasing plate 410 may comprise a piece of metal or other suitable material wherein each biasing member 412 is stamped or otherwise cut and formed to correspond with a staple forming insert 400. The biasing plate 410 may comprise a single plate that is supported within a cavity 251f in the anvil 20f or multiple plates 410 may be employed on each side of the anvil slot. It will be understood that a similar arrangement may be employed on the right side of the anvil sot. Each staple forming insert 400 may be attached to its corresponding biasing member 412 by adhesive or other suitable fastener arrangement. Thus, it will be appreciated that a variety of different numbers and arrangements of movable staple forming inserts may be employed without departing from the spirit and scope of the present invention. In particular, at least one movable staple forming insert may be employed on each side of the anvil slot.

Figure 30:
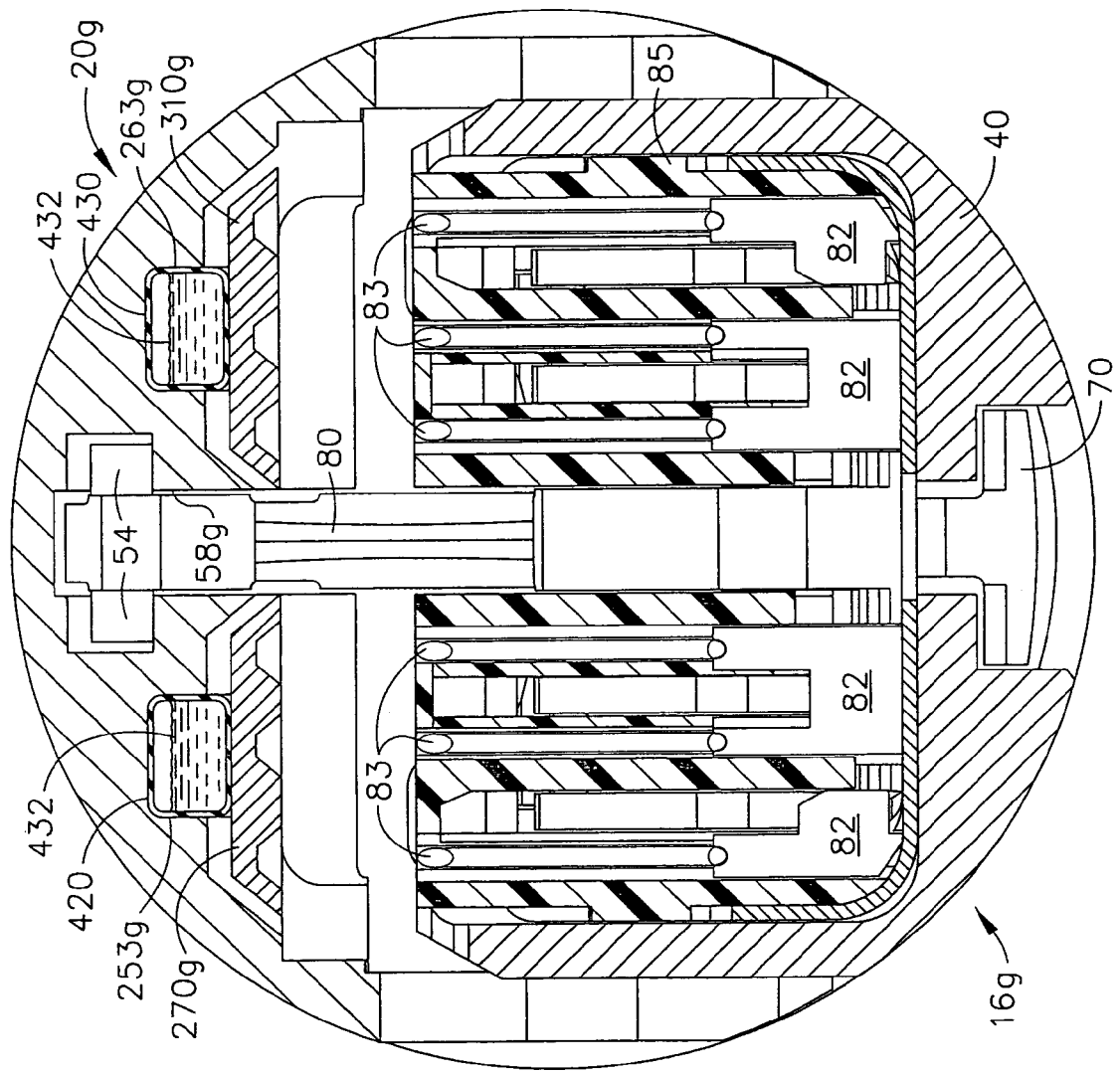
FIG. 30 is an end cross-sectional view of another staple applying assembly of the present invention with some elements shown in solid form for clarity.
Figure 31:
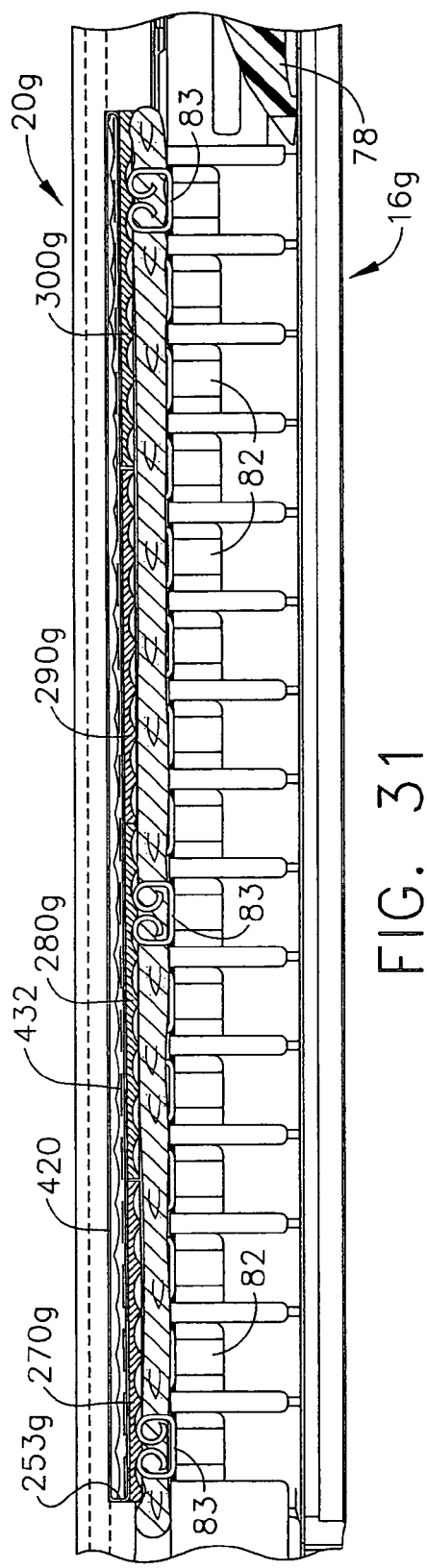
FIG. 31 is a longitudinal cross-sectional view of the staple applying assembly of FIGS. 27 and 30 with tissue clamped and stapled therein.
Figure 32:
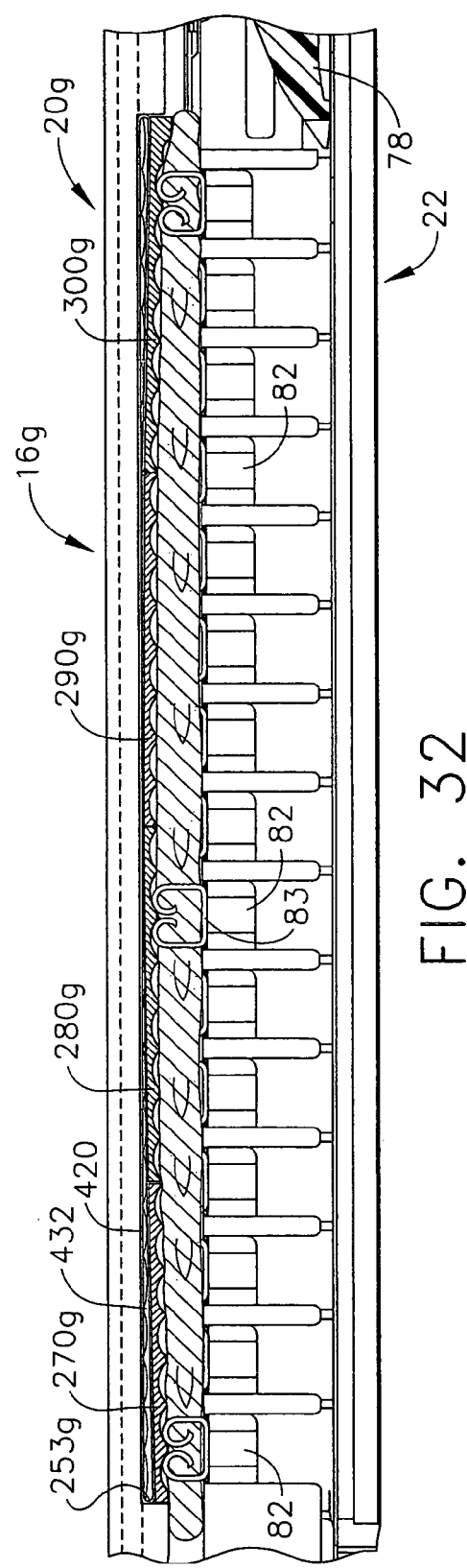
FIG. 32 is another longitudinal cross-sectional view of the staple applying assembly of FIG. 31 with another portion of tissue clamped and stapled therein.

FIGS. 30-32 illustrate another staple applying assembly 16g of other embodiments of the present invention wherein the biasing or compliant medium between the staple forming inserts and the anvil comprises at least one fluid bladder. More specifically, as can be seen in FIG. 30, a left bladder 420 is positioned within a left side cavity 253g on the left side of the anvil slot 58g in the anvil 20g. Likewise, a right side bladder 430 is positioned with a right side cavity 263 in the anvil 20g. The series of left side staple forming inserts 270g, 280g, 290g, 300g may be attached to the left side bladder 430 by a suitable adhesive or other fastener arrangement. Likewise the right side staple forming inserts (not shown) may be attached to the right side bladder 430 by adhesive or other suitable fastener arrangements. In one embodiment, each bladder 420, 430 is sealed and partially filled with a liquid 432 such as, for example, glycerin oil or saline solution. Those of ordinary skill in the art will appreciate that such arrangement will permit the staple forming inserts to move to better accommodate variations in the thickness of the tissue clamped within the staple applying assembly 16g. For example, for tissues that have a relatively constant thickness, the liquid 432 will be relatively evenly distributed within each of the bladders 420, 430 to provide a relatively even support arrangement for the staple forming inserts. See FIG. 31. However, when a thicker portion of tissue is encountered, those staple forming inserts corresponding to the thicker tissue will be compressed into their respective anvil cavity thereby forcing the liquid in that part of the bladder to the portions of the bladder corresponding to the thinner tissue portions. See FIG. 32.

Figure 33:
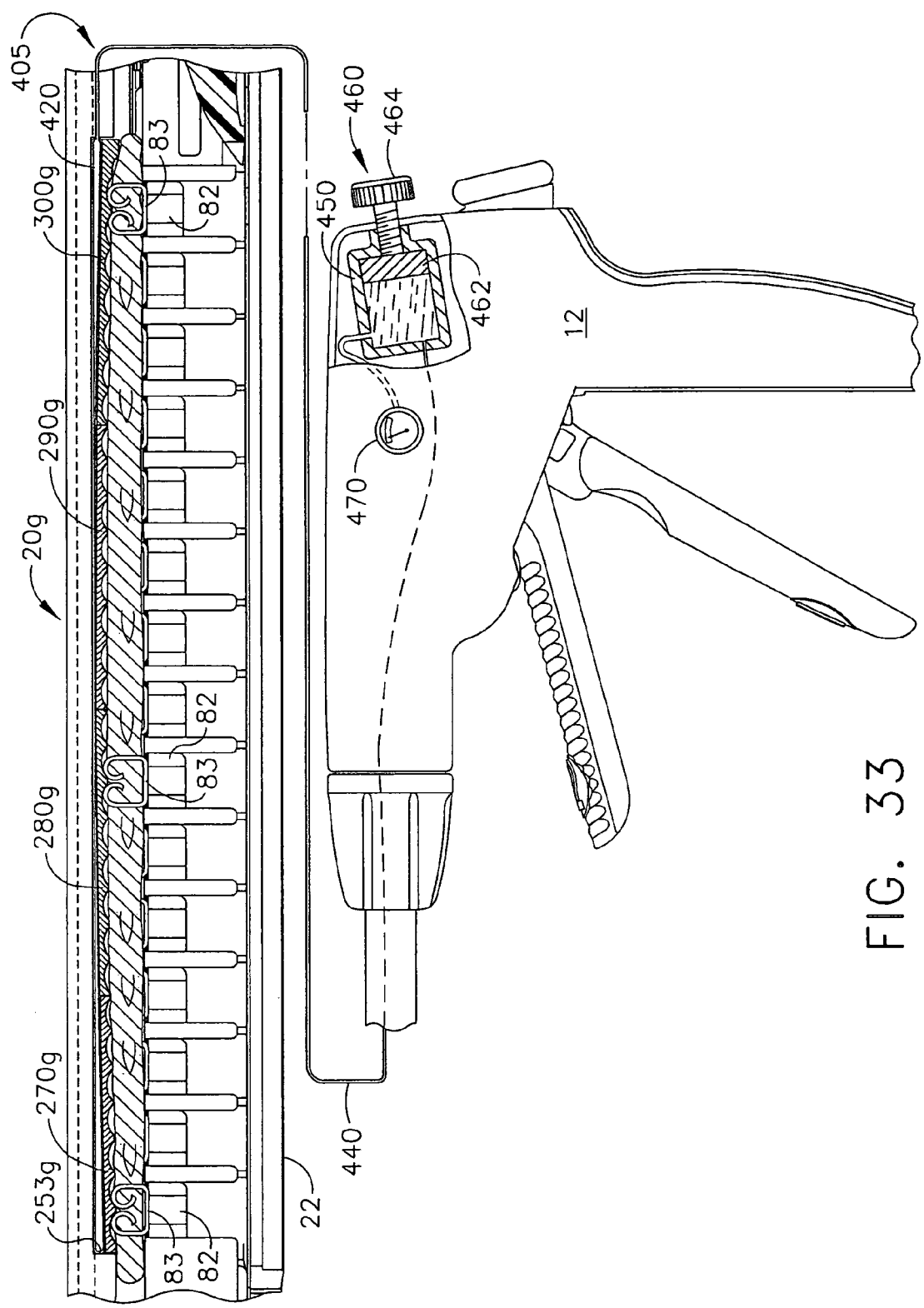
FIG. 33 is another longitudinal cross-sectional view of the staple applying assembly of FIGS. 30-32 fluidically coupled to a fluid reservoir supported by a handle assembly of various embodiments of the present invention.

In some applications, it may be desirable for the clinician to be able to control the amount of pressure within the bladders 420, 430. For example, less pressure may be desirable when cutting and stapling more delicate tissues such as lung tissue and the like. More pressure may be desirable when cutting and stapling thicker tissues such as, for example, stomach tissue, intestine tissue, kidney tissue, etc. To provide the clinician with this additional flexibility, the bladders 420, 430 may each be fluidically coupled by a supply line 440 or conduit to a fluid reservoir 450 supported by the handle portion 12 of the instrument. In the embodiment illustrated in FIG. 33, the clinician can increase or decrease the amount of fluid within the bladders 420, 430 and resulting pressure therein by means of an adjustment mechanism 460 mounted to the fluid reservoir 450. In various embodiments, the adjustment mechanism 460 may comprise a piston 462 that is attached to an adjustment screw 464. By adjusting the adjustment screw 464 inward, the piston 462 forces fluid out of the reservoir 450 to the bladders 420, 430. Conversely, by reversing the adjustment screw 464, the piston 462 permits more fluid 432 to return or remain within the reservoir 450. To assist the clinician in determining the amount of pressure within that hydraulic system, generally designated as 405, a pressure gauge 470 may be employed as shown. Thus, for those tissues requiring a higher amount of pressure, the clinician can preset the pressure in the bladders 420, 430 to a pressure that is conducive to successfully clamp and staple that particular type of tissue. While a piston/screw arrangement has been described for controlling the pressure in the hydraulic system, the skilled artisan will understand that other control mechanisms could successfully be employed without departing from the spirit and scope of the present invention.

Figure 30A:
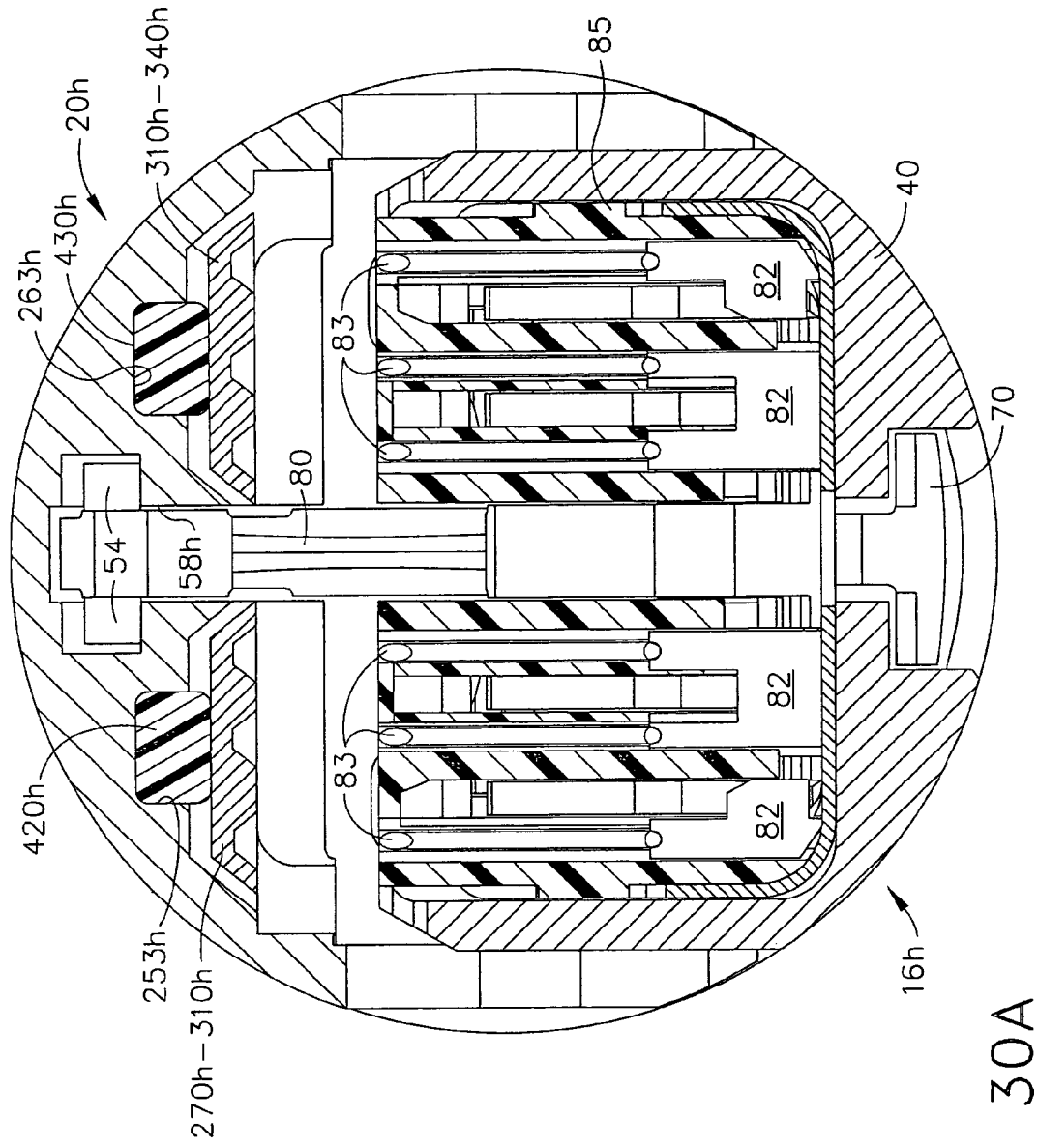
FIG. 30A is an end cross-sectional view of another staple applying assembly of the present invention with some elements shown in solid form for clarity.

FIG. 30A illustrates another staple applying assembly 16h of other embodiments of the present invention wherein the biasing or compliant medium between the staple forming inserts and the anvil comprises at least one compressible polymer member. More specifically, as can be seen in FIG. 30A, a left compressible polymer member 420h is positioned within a left side cavity 253h on the left side of the anvil slot 58h in the anvil 20h. Likewise, a right side compressible polymer member 430h is positioned with a right side cavity 263h in the anvil 20h. The series of left side staple forming inserts 270h-300h may be attached to the left compressible polymer member 420h by a suitable adhesive or other fastener arrangement. Likewise the right side staple forming inserts 310h-340h may be attached to the right side compressible polymer member 430h by adhesive or other suitable fastener arrangements.

FIGS. 34-37 depict a unique and novel collapsible or compressible staple driver arrangement that enables the various staple drivers to accommodate different tissue thicknesses by collapsing or compressing in response to compression forces that the driver encounters during the firing process. As used herein, the term "firing process" refers to the process of driving the staple drivers towards the staple forming undersurface of the anvil. As was mentioned above, prior staple drivers were fabricated from stiff/rigid material designed to resist deflection and deformation when encountering compression forces during the firing process. A variety of such driver configurations are known. For example, some staple drivers are configured to support a single staple and others are designed to support multiple staples. A discussion of single and double staple drivers and how they may be operably supported and fired within a staple cartridge is found in U.S. patent application Ser. No. 11/216,562, filed Sep. 9, 2005, entitled Staple Cartridges For Forming Staples Having Differing Formed Staple Heights to Frederick E. Shelton, IV, the disclosure of which is herein incorporated by reference.

FIG. 34 depicts a staple applying assembly 16h that includes an elongate channel 40h that has an anvil 20h pivotally coupled thereto in a known manner. The elongate channel 40h is configured to operably support a staple cartridge 42h therein. The anvil 20h has a staple forming undersurface 60h thereon that is adapted to confront the upper surface 43h of the staple cartridge 42h when the anvil 20h is pivoted to the closed position shown in FIG. 34. The staples 83 are each supported on a corresponding staple driver 500, the construction of which will be discussed in further detail below.

Each staple driver 500 may be movably supported within a corresponding staple channel 87h provided in the cartridge body 85h as shown in FIGS. 34 and 35. Also operably supported within the cartridge body 85h is a driving member or wedge sled 78 that is oriented for engagement by the E-beam firing member 50 during the firing process. See FIG. 34. As the E-beam firing member 50 and wedge sled 78 are driven distally through the elongate channel 40h and staple cartridge 42 in a known manner, the wedge sled 78 drives the staple drivers 500 upwardly within the cartridge body 85h. As the staple drivers 500 are driven upwardly toward the staple forming undersurface 60h of the anvil 20h, they carry with them their respective staple 83 or staples which are driven into forming engagement with the corresponding staple forming pockets 61h in the staple forming undersurface 60h of the anvil 20h. As the ends 88 of the staple 83 contact the forming pockets 61h, they are bent over thus providing the staple 83 with a shape that somewhat resembles a "B". While the various embodiments of the present invention have been described herein in connection with E-beam firing members, it is conceivable that these various embodiments may also be successfully employed with a variety of different firing member and driving member arrangements without departing from the spirit and scope of the present invention.

Figure 36:
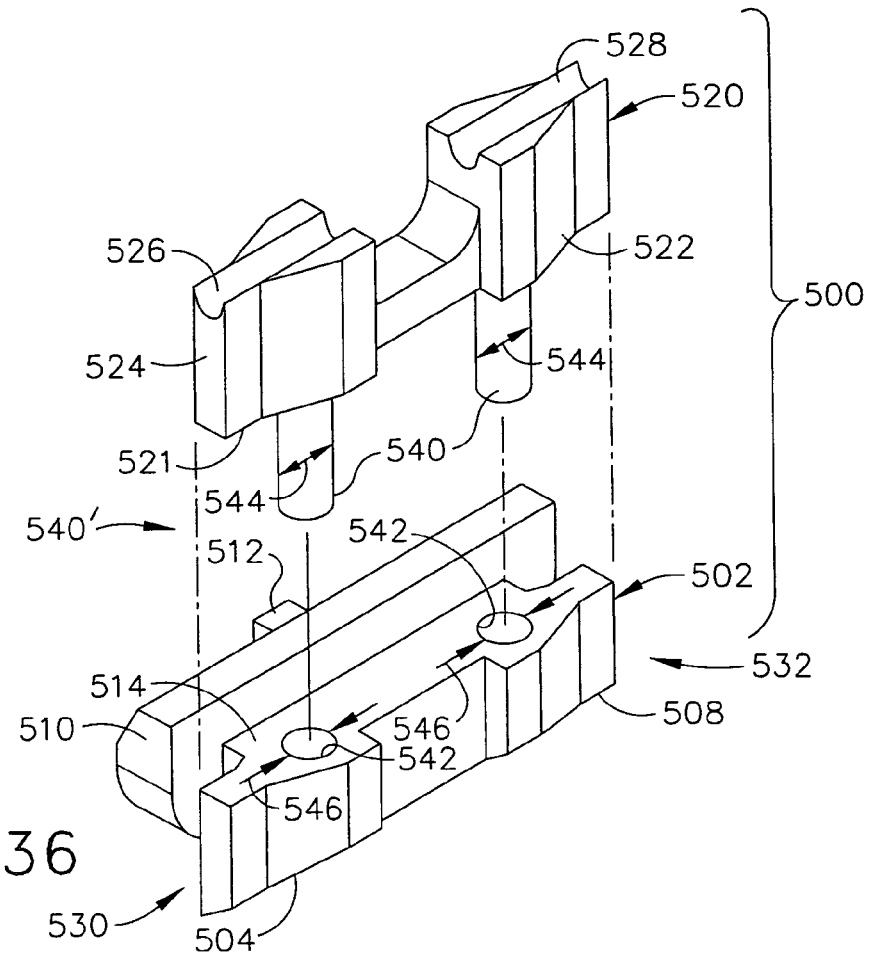
FIG. 36 is an exploded perspective view of a collapsible staple driver embodiment of the present invention.
Figure 37:
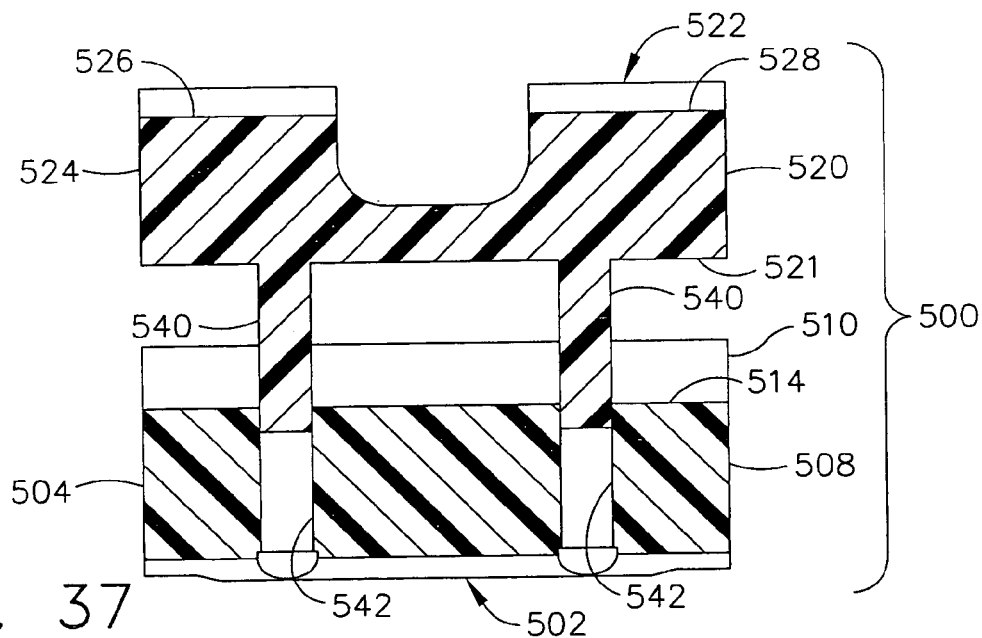
FIG. 37 is a cross-sectional view of the collapsible staple driver embodiment of FIG. 36 in a first (uncollapsed) position.

One collapsible staple driver embodiment of the present invention is depicted in FIGS. 36 and 37. As can be seen in those Figures, the collapsible or compressible staple driver 500 includes a base portion 502 and a staple supporting portion 520 that is movable from a first uncollapsed position relative to the base portion 502 in response to compression forces generated during the firing process. In various embodiments, the base portion 502 may have a forward support column segment 504 and a rearward support column segment 508 that is spaced from the forward support column segment 504 and is substantially integrally formed therewith. The base portion 502 may also have an upstanding side portion 510 that has a rib 512 protruding from a backside therefrom. The upstanding side portion 510 serves to define a receiving ledge 514 in the base portion 502 for receiving the staple supporting portion 520 thereon. Those of ordinary skill in the art will understand that when the staple supporting portion 520 is received on the ledge 514, the staple driver 500 is unable to collapse or compress any further.

The staple supporting portion 520 of the staple driver 500 may similarly include a forward support column segment 522 and rearward support column segment 524 that is spaced from the forward support column segment 522. When the staple supporting portion 520 is received on the base portion 502, the forward support column segments 504, 522 serve to form a forward column portion 530 and the reward column segments 508, 524 form a rearward column portion 532. A forward staple receiving groove 526 is formed in the forward support column segment 522 and a rearward staple receiving groove 528 is formed in the rearward support column segment 524. The forward staple receiving groove 526 and the rearward staple receiving groove 528 serve to support a staple 83 therein as illustrated in FIG. 35. The rib 512 and the forward column 530 and rearward column 532 may cooperate with corresponding channels (not shown) in the staple cartridge body 85 to provide lateral support to the staple driver 500 while permitting the driver to be driven upward within the cartridge body 85 during the firing process.

In various embodiments, a resistive attachment structure, generally designated as 540' is provided to support the staple supporting portion 520 in a first uncompressed or uncollapsed orientation relative to the base portion (FIG. 37) prior to encountering any compressive forces during the firing operation and to permit the staple supporting portion 520 and the base portion to move towards each other(collapse or compress) in response to the magnitude of the compression forces applied to the staple supporting portion 520 and base portion 520 during the staple firing operation. As can be seen in FIGS. 36 and 37, the resistive attachment structure 540' in various embodiments may comprise a pair of attachment rods 540 that protrude from the bottom 521 of the staple supporting portion 520 and correspond to holes or apertures 542 in the base portion 502. The rods 540 are sized and shaped relative to the holes 542 to establish an interference fit or "light press fit" (i.e., an interference of approximately 0.001 inches) therebetween such that when the staple supporting portion 520 and base driver portion 502 are compressed together during the staple firing operation as will be discussed in further detail below, the staple supporting portion 520 and the base portion 502 can compress toward each other to reduce the overall height of the staple driver 500 in relation to the amount of compression force encountered during the firing process. In various embodiments, for example, the staple supporting portion 520 and base portion 520 may be fabricated from the same material such as, for example, ULTEM®. In other embodiments, the base portion 502 and the staple supporting portion 520 may be fabricated from different materials. For example, staple supporting portion 520 may be fabricated from ULTEM® and the base portion 502 may be fabricated from glass or mineral filled ULTEM®. However, other materials could also be employed. For example, the base portion 502 could be fabricated from Nylon 6/6 or Nylon 6/12.

In various embodiments, a frictional or an interference fit of approximately 0.001 inch may be established between the attachment rods 540 and their corresponding holes 542. However, other degrees of interference fit may be employed to attain the desired amount and rate of driver compression in proportion to the magnitude of compression forces encountered when stapling a particular type/thickness of tissue. For example, in one embodiment, the degree of interference fit between the attachment rods 540 and their respective holes 542 may be approximately 0.002 to 0.005 inches for stapling tissues wherein it is anticipated that compression forces on the order of approximately 2-5 pounds may be generated during the firing operation.

FIG. 35 illustrates various ranges of travel and compression that the staple drivers 500 may experience when encountering tissues of varying thicknesses. More specifically, FIG. 35 illustrates a portion of tissue 560 clamped between the upper surface 43h of the staple cartridge 42h and the staple forming undersurface 60h of the anvil 20h. As illustrated in FIG. 35, the tissue 560 has three thicknesses. The thickest portion of tissue is designated as 562 and comprises the portion of tissue that is on the right side of the Figure. The next thickness portion of tissue is designated as 564 and the thinnest portion of tissue 560 is designated as 566 and is on the left side of the Figure. For the purposes of this explanation, the staple driver associated with tissue portion 562 is designated as staple driver 500a. The staple driver associated with tissue portion 564 is designated as staple driver 500b and the staple driver associated with tissue portion 566 is designated as 500c. It will be understood that staple drivers 500a, 500b, 500c, may be identical in construction to staple driver 500 as described above.

Turning to staple driver 500a first, as the staple driver 500a is driven upwardly towards the staple forming undersurface 60h of the anvil 20h by the wedge sled (not shown in FIG. 35), it encounters the thick tissue portion 562 which resists the upward movement of the staple driver 500a. Such resistive force (represented by arrow 570) opposes the drive force (represented by arrow 572) generated by the wedge sled and serves to overcome the amount of interference established between the attachment rods 540 and their respective holes 542 and forces the rods 540 deeper into their respective holes 542 to thereby permit the staple supporting portion 520a of the staple driver 500a and base portion 502a to move toward each other. This movement of the staple supporting portion 520a and base portion 502a towards each other under a compressive force generated during the staple firing operation is referred to herein as "collapsing" or "compressing". When in the completely compressed position wherein the staple supporting portion 520a is received on the ledge 514a of the base portion 502a, the staple supporting ledges 526a, 528a on the staple supporting portion 520a may preferably support the bottom cross member 89 of the staple 83 above the upper surface 43h of the staple cartridge 42h to avoid catching the staple 83 on the staple cartridge 42h when the staple applying assembly 16h is withdrawn. The compressed height of the staple driver 500a is designated by arrow 574 in FIG. 35.

Turning next to staple driver 500b which corresponds to tissue portion 564, because the tissue portion 564 is not as thick as tissue portion 562, the resistive force 570b encountered by the staple driver 500b during the firing operation is not as great as resistive force 570. Therefore, the attachment pins 540b of staple driver 500b are not advanced into their respective holes 542b as far as the pins 540 of staple driver 500a were advanced into their respective holes 542. Thus, the compressed height 576 of staple driver 500b is greater than the compressed height 574 of staple driver 500a. As can also be seen in FIG. 35, the bottom portion 89 of the staple 83 supported in staple driver 500b is supported above the upper surface 43h of the staple cartridge 42h.

Staple driver 500c is associated with the thinnest tissue portion 566. Thus, the resistive force 570c encountered by the staple driver 500c during the staple firing operation is less than the resistive force 570b that was encountered by staple driver 500b. Thus, the pins 540c of staple driver 500c are not advanced into their respective holes 542c as far as the pins 540b of staple driver 500b were advanced into their respective holes 542b. Thus, the compressed height 578 of staple driver 500c is greater than the compressed height 576 of staple driver 500b.

As can be further seen in FIG. 35, because the compressed height 578 of staple driver 500c is greater than the compressed height 576 of staple driver 500b, the staple 83c supported by staple driver 500c was compressed to a greater extent than the staple 83b that was supported by staple driver 500b. Thus, the formed height of staple 83c is less than the formed height of staple 83b which is less than the formed height of staple 83a as illustrated in FIG. 35.

Those of ordinary skill in the art will appreciate that the number, shape, composition and size of the attachment rods and their respective holes can vary from embodiment to embodiment without departing from the spirit and scope of the present invention. Such interrelationship between the attachment rods and their respective holes serves to establish an amount of frictional interference therebetween which can be overcome in relation to various compression forces encountered when clamping/stapling different thicknesses of tissue. In an alternative version, the attachment to rods 540 may be formed on the base portion 502 and the holes provided in the staple supporting portion 520.

Figure 38:
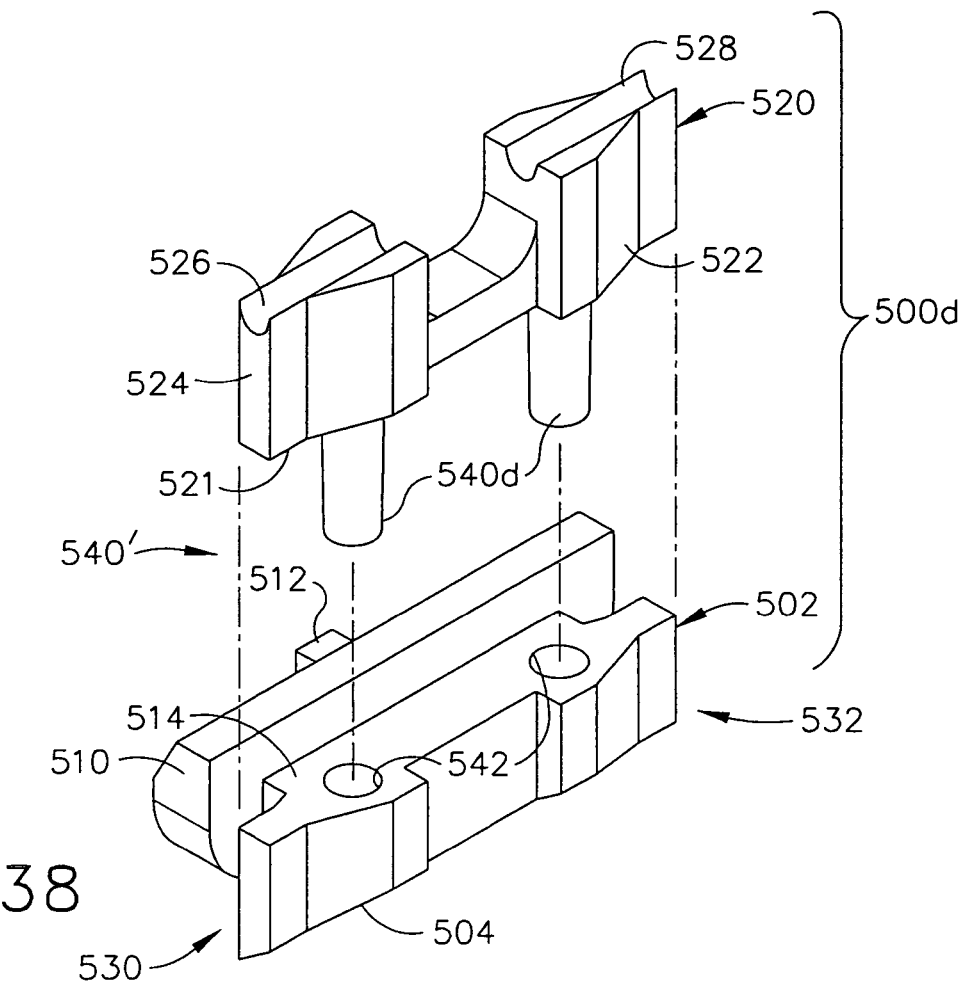
FIG. 38 is an exploded perspective view of another collapsible staple driver embodiment of the present invention.
Figure 39:
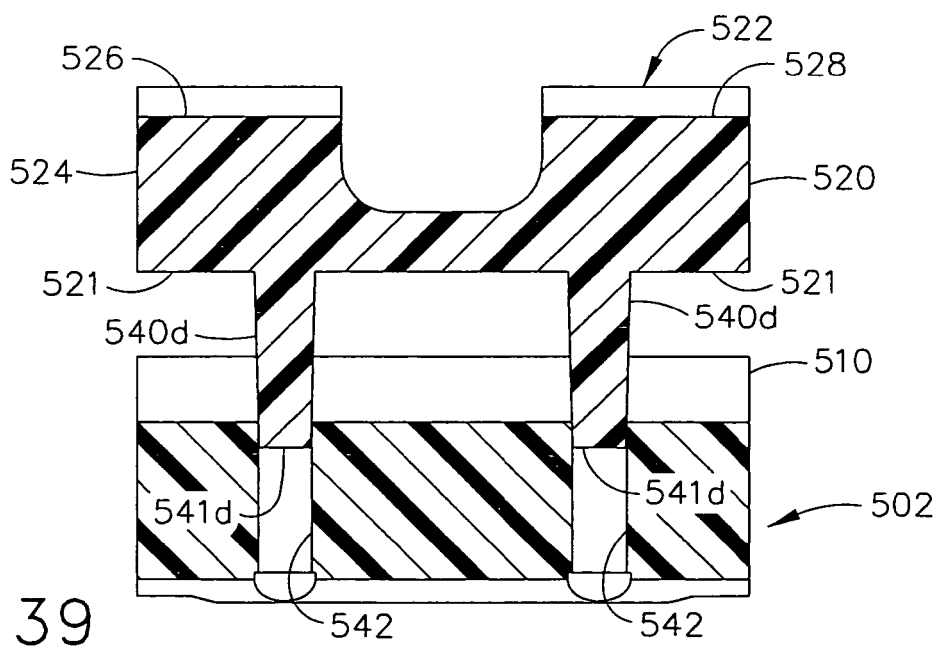
FIG. 39 is a cross-sectional view of the collapsible staple driver embodiment of FIG. 38 in a first (uncollapsed) position.
Figure 40:
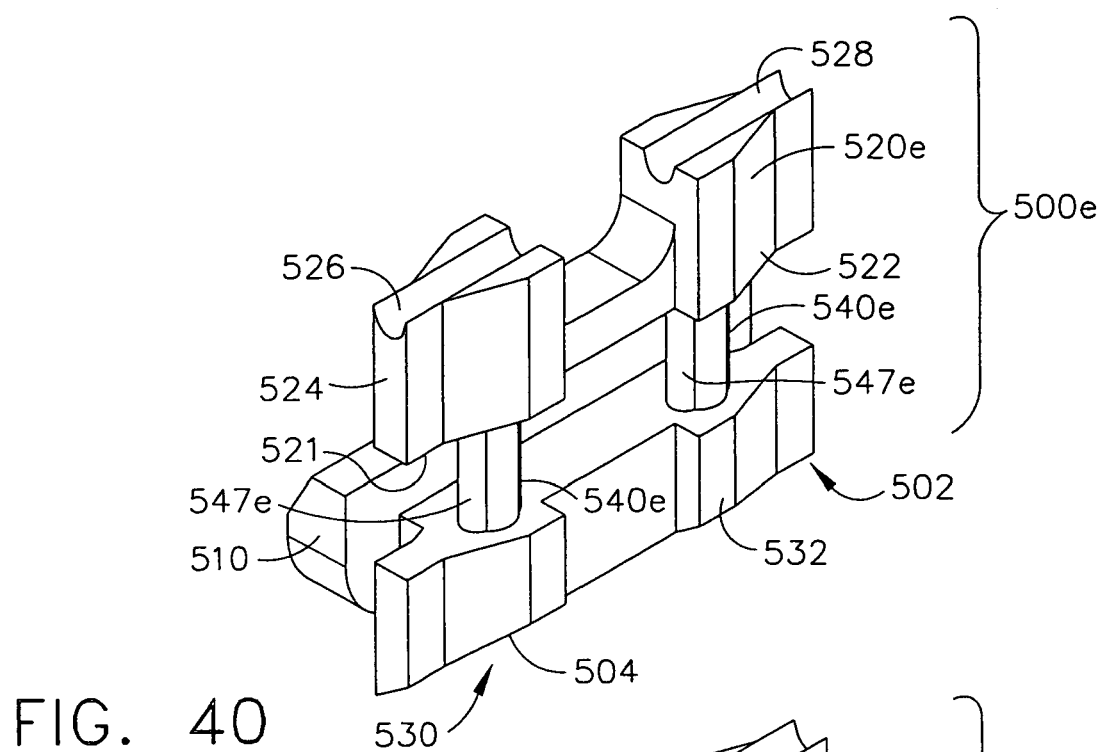
FIG. 40 is a perspective view of another collapsible staple driver embodiment of the present invention in a first (uncollapsed) position.
Figure 41:
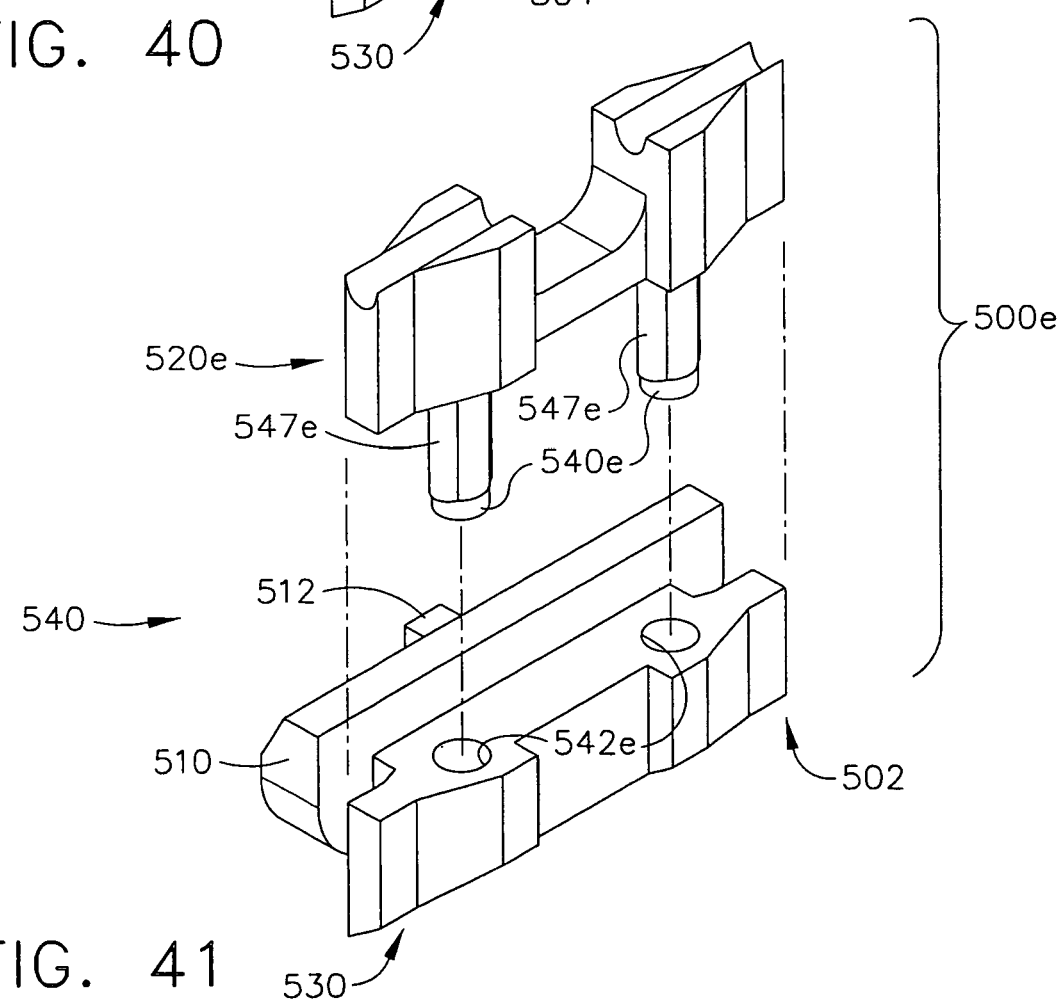
FIG. 41 is an exploded perspective view of the collapsible staple driver embodiment of FIG. 40.
Figure 42:
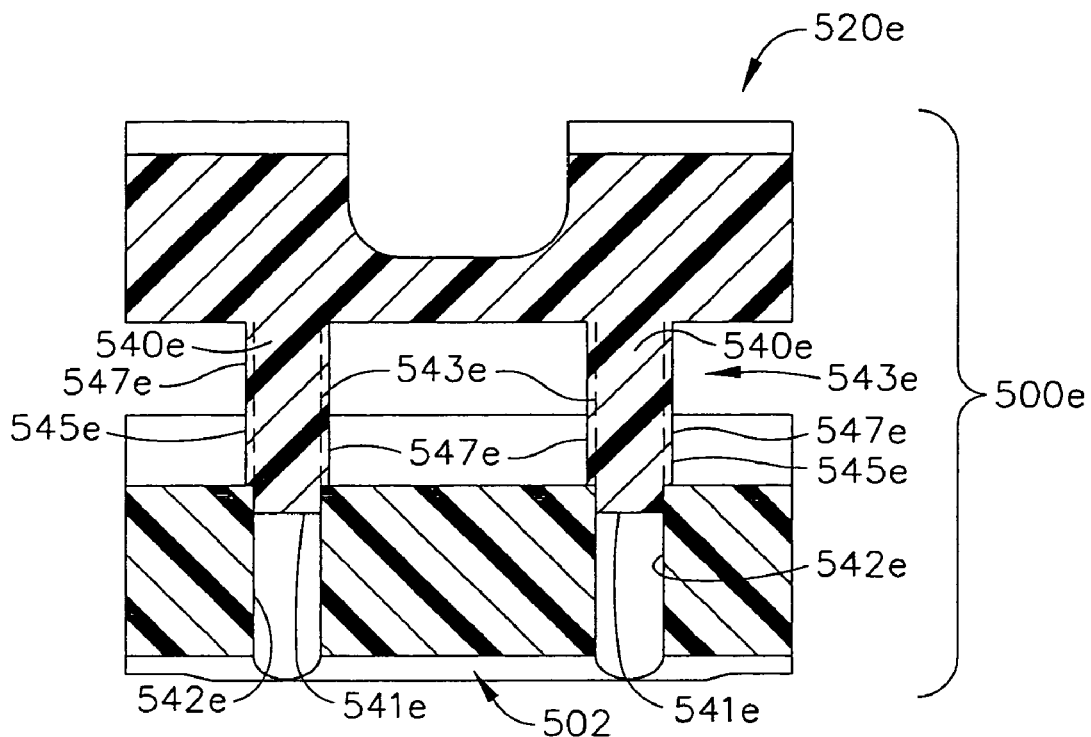
FIG. 42 is a cross-sectional view of the collapsible staple driver embodiment of FIGS. 40 and 41 in a first (uncollapsed) position.
Figure 43:
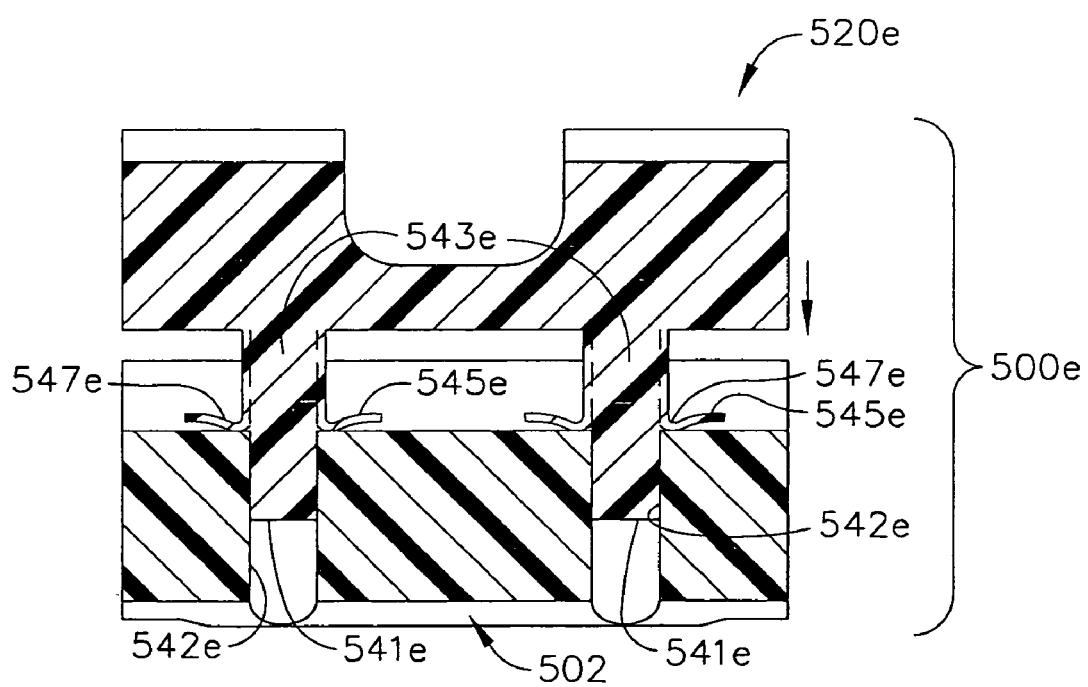
FIG. 43 is another cross-sectional view of the collapsible staple driver embodiment of FIGS. 40-42 after compression forces have been applied thereto.

FIGS. 38 and 39 illustrate another staple driver 500d embodiment of the present invention that may be substantially identical in construction and operation to the staple drivers 500 described above, except that the attachment rods 540d are somewhat tapered or frusto-conically shaped. In various embodiments, for example, the ends 541d of the attachment rods 540d may be sized relative to holes 542 such that a light press fit is established therebetween when in the first uncollapsed state depicted in FIG. 39. The degree of taper of the attachment rods 540d may be tailored to attain the desired amount of staple driver compression in relation to the magnitude of compression forces encountered during the staple firing process. Thus, in these embodiments, the magnitude of the interference fit between the attachment rods 540d and the holes 542 increases as the staple driver 500d encounters greater compression forces which drive the attachment rods 540d deeper into their respective holes 542d. In alternative embodiments, the attachment rods 540 may have a round shape and the holes 542 may be tapered to attain the desired amount and rate of staple driver compression in proportion to the amount of anticipated compression forces applied thereto during the firing operation. In an alternative version, the attachment rods 540d may be formed on the base portion 502 and the holes 542 be formed in the staple supporting portion 520.

FIGS. 40-43 illustrate another staple driver 500e embodiment of the present invention that may be substantially identical in construction and operation to the staple drivers 500 described above, except that the attachment rods 540e are configured or shaped to include an additional amount of material oriented to be sheared off of the remaining portion of the rods as the staple driver 500e encounters compression forces during the firing operation. More specifically and with reference to FIG. 42, the attachment rods 540e have a tip portion 541e that is received within the corresponding hole 542e. The tip portion 541e may be sized relative to the hole 542e such that a sliding fit is achieved therebetween or, in other embodiments, a small interference fit may be established between those components when in the first uncollapsed position. The remaining portion 543e of each attachment rod 540e may be provided or formed with an additional amount of material 545e that is designed to be sheared therefrom as the staple driver 500e encounters the anticipated compression forces during the firing operation. See FIG. 43. The additional material 545e may extend completely around the circumference of the portion 543e of each attachment rod 540e or the material 543e may comprise one or more segments oriented around the circumference of the attachment rod 540e. For example, in the embodiment depicted in FIGS. 40-43, two segments 547e of material 543e are diametrically opposed on each attachment rod 540e as shown. In various embodiments, the diametric distance between the segments may be somewhat larger than the diameter of the holes 542e to cause the segments 547e to be sheared or removed from at least a portion of the rods 540e as the staple driver 500e encounters the anticipated compression forces during the firing operation.

The portions of additional material 543e may comprise an integral portion of the attachment rod 540e or the additional material 543e may comprise a second material applied to the attachment rod 540e and designed to shear off therefrom when the staple driver 500e encounters the anticipated compression forces. In various embodiments, the base portion 502 may be fabricated from a material that is more rigid that the material from which attachment rods 540e and/or the additional material 543e are fabricated such that the base portion 502 facilitates the shearing off of additional material 543e as the staple support portion 520e and base portion 502e are compressed together during the staple firing operation. In an alternative version, the attachment rods 540e may be formed on the base portion 502 and the holes 542e be provided in the staple supporting portion 520e.

Figure 44:
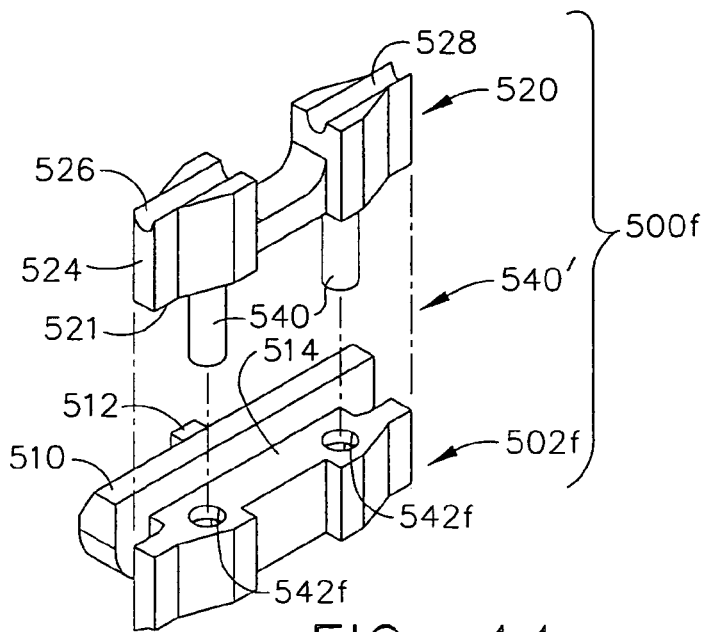
FIG. 44 is an exploded perspective view of another collapsible staple driver embodiment of the present invention.
Figure 45:
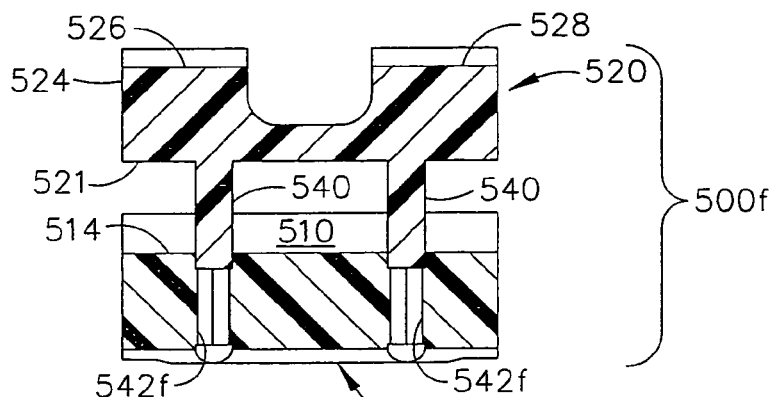
FIG. 45 is a cross-sectional view of the collapsible staple driver embodiment of FIG. 44 in a first (uncollapsed) position.
Figure 46:
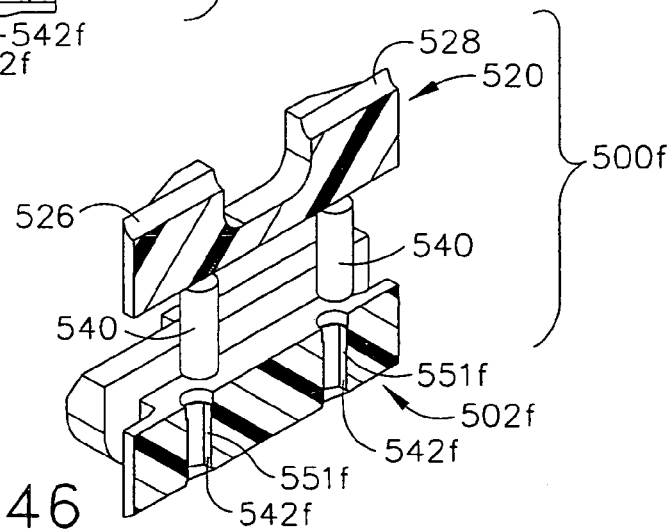
FIG. 46 is an exploded perspective view of the collapsible staple driver embodiment of FIGS. 44 and 45 with some of the elements thereof shown in cross-section.

FIGS. 44-46 illustrate another staple driver 500f of the present invention that may be substantially identical in construction and operation to the staple drivers 500 described above, except that the holes 542f in the base portion 502f may be hexagonally shaped or may have one or more surfaces therein designed to establish an interference fit with the attached rods 540 or to otherwise resist further entry of the attachment rods 540 into the holes 542f. For example, the holes 542f shown have a pair of flat surfaces 551f formed therein that serve to establish an interference fit or a degree of frictional resistance between the attachment rods 540f and the holes 542f which can be overcome by the various compression forces encountered when clamping/stapling different thicknesses of tissue. In the embodiment depicted in FIGS. 44-46, the attachment rods 540 have a substantially circular cross-sectional shape and the holes 542f have flat surfaces 551 formed therein. In alternative embodiments, however, the holes 542 may be round and the flat surfaces may be formed on the attachment rods 540. In an alternative version, the attachment rods 540 may be provided on the base portion 502f and the holes 542f be provided in the staple supporting portion 520.

Figure 47:
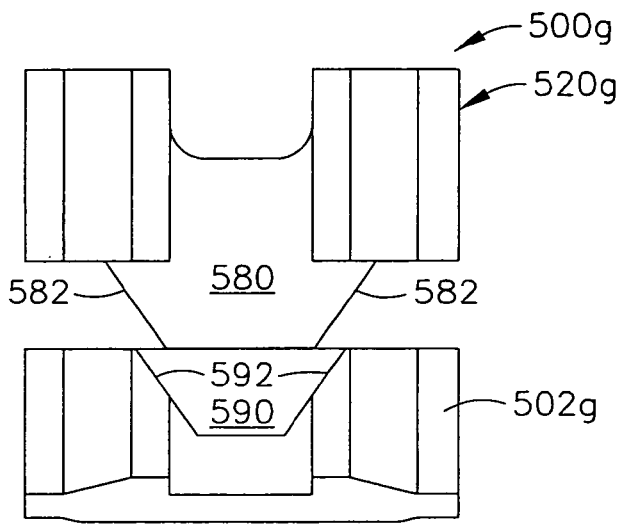
FIG. 47 is an exploded front view of another collapsible staple driver embodiment of the present invention.
Figure 48:
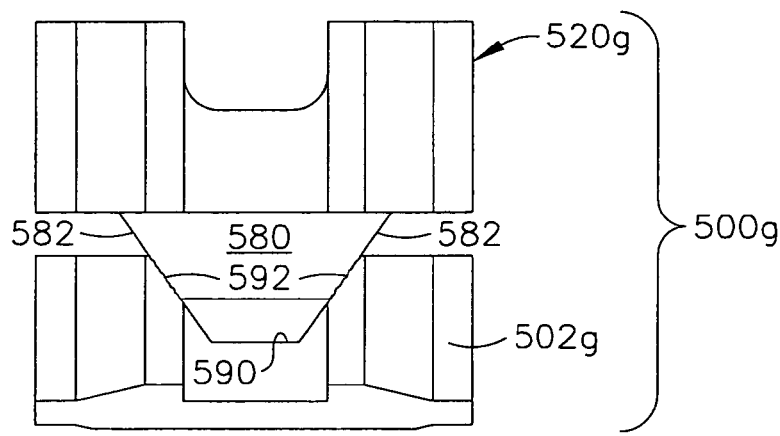
FIG. 48 is another front view of the collapsible staple driver of FIG. 47 in a first (uncollapsed) position.
Figure 49:
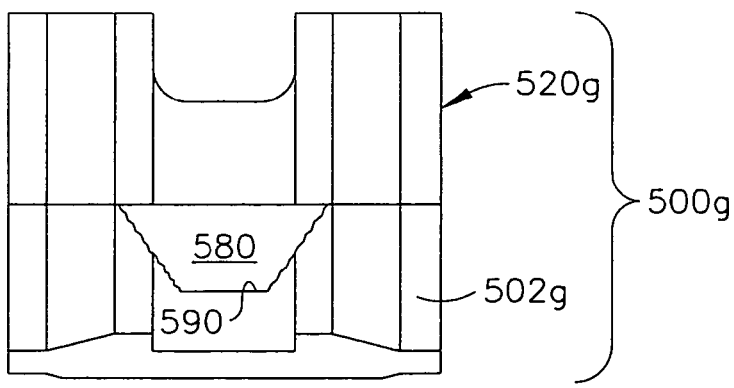
FIG. 49 is another front view of the staple driver of FIGS. 47 and 48 after is has been compressed to a fully collapsed position.

FIGS. 47-49 illustrate another staple driver 500g of the present invention that comprises a base portion 502g and a staple supporting portion 520g. The staple supporting portion 520g has staple supporting grooves (not shown) formed therein and a downwardly protruding tang 580 protruding from its undersurface 521g. The tang 580 has two tapered surfaces 582 and is shaped to be received in a corresponding cavity 590 formed in the base portion 502g. The cavity 590 is formed with tapered sides 572 and is sized to receive the tang 580 therein in the following manner. As the driver staple 500g encounters the compression forces generated during the firing operation, the tang 580 is forced into the cavity 590. FIG. 49 illustrates the staple driver 500g in a fully collapsed or compressed position. The staple supporting portion 520g and/or tang 580 may be fabricated from a material that is somewhat more compliant than the material from which the base portion 502g is formed so that the tang 580 can be forced into the cavity 590 in the base portion 502g without substantially distorting the base portion 502g to the extent that it would hamper the ability of the staple driver 500g to be fully driven to a final firing position. For example, the staple supporting portion and/or the tang 580 may be fabricated from ULTEM® and the base portion 502g may be fabricated from glass filled Nylon to achieve the desired amount of driver compression when encountering the anticipated compression forces during the firing operation. In an alternative version, the tang 580 may be provided on the base portion 502g and the hole 590 be provided in the staple supporting portion 520g.

FIGS. 50-52 illustrate another staple driver 500h embodiment of the present invention that may be substantially identical in construction and operation to the staple drivers 500 described above, except that, instead of attachment rods, the staple supporting portion 520h has two tapered tangs 600 protruding therefrom designed to be compressed into a V-shaped cavity 610 formed in the base portion 502h. Prior to commencement of the firing operation, the staple supporting portion 520h is supported on the base portion 502h within the staple cartridge. As the staple supporting portion 520h and the base portion 502h are compressed together during the firing operation, the tapered tangs 600 are forced inwardly as shown in FIG. 52. The degree to which the tangs 600 are compressed into the V-shaped cavity 610 is dependent upon the magnitude of the compression forces encountered during the firing operation.

The staple supporting portion 500h and/or tangs 600 may be fabricated from a material that is somewhat more compliant than the material from which the base portion 502h is formed so that the tangs 600 can be forced into the V-shaped cavity 610 in the base portion 502h without substantially distorting the base portion 502h to the extent that it would hamper the ability of the staple driver 500h to be fully driven to a final firing position. For example, the staple supporting portion and/or the tangs 600 may be fabricated from Nylon with no fill and the base portion 502h may be fabricated from ULTEM® with glass or mineral fill to achieve the desired amount of staple driver compression when encountering the anticipated compression forces during the firing operation. In an alternative version, the tangs 600 may be provided on the base portion 502h and the cavity 610 may be provided in the staple supporting portion 520h.

Figure 53:
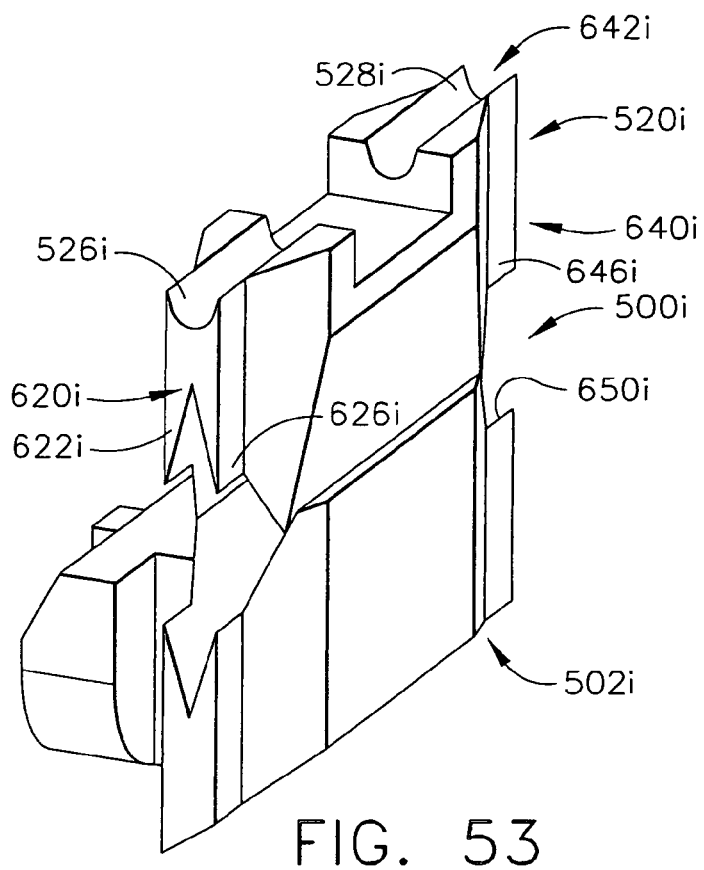
FIG. 53 is a perspective view of another collapsible staple driver embodiment of the present invention.
Figure 54:
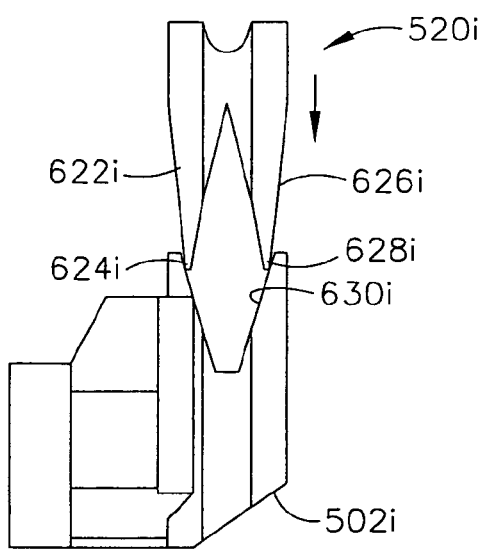
FIG. 54 is a side elevational view of the collapsible staple driver of FIG. 53 in a first (uncollapsed) position.
Figure 55:
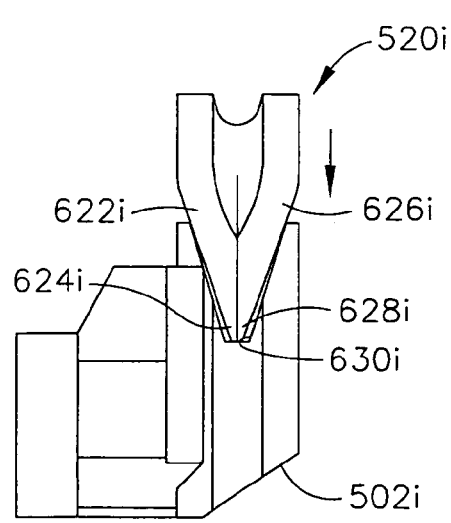
FIG. 55 is another side elevational view of the collapsible staple driver of FIGS. 53 and 54 after being compressed to a fully collapsed position.

FIGS. 53-55 illustrate yet another staple driver 500i embodiment of the present invention that includes a staple supporting portion 520i that has V-shaped staple supporting grooves 630i, 650i therein. In this embodiment, the staple supporting portion 520i has a first pair 620i of two tapered tangs 622i, 626i protruding therefrom oriented to be compressed into the first V-shaped groove or cavity 630i and a second pair 640i of two tapered tangs 642i, 646i oriented to be compressed into the second V-shaped groove or cavity 650i. More specifically and with reference to FIG. 54, the first tang 622i has an end 624i that is spaced from an end 628i of the second tang 626i prior to commencement of the staple firing operation. When in the position illustrated in FIG. 54, the ends 624i, 628i are biased outwardly into frictional contact with the upper side walls of the first V-shaped groove 630i to retain the staple supporting portion 520i in the uncollapsed position shown in FIG. 54. Although not shown, the second pair 640i of tangs 642i, 646i are also similarly configured as tangs 622i, 626i and serve to engage the second V-shaped groove 650i in the same manner.

As the staple supporting portion 520i and the base portion 502i are compressed together during the firing operation, the ends 624i, 628i of the first tangs 622i, 626i and the ends of the second tangs 642i, 646i are biased toward each other to permit the tangs to be driven deeper into their respective grooves 630i, 650i. FIG. 55 illustrates the first pair 620i of tangs 622i, 626i in their fully compressed state which also corresponds to the fully compressed state of the driver 500i. The degree to which the tangs are compressed into their respective V-shaped grooves is dependent upon the magnitude of the compression forces encountered during the firing operation.

The staple supporting portion 500i and/or tangs 622i, 626i, 642i, 646i may be fabricated from a material that is somewhat more compliant than the material from which the base portion 502i is formed so that the tangs 622i, 626i, 642i, 646i can be forced into their respective V-shaped grooves in the base portion 502i without substantially distorting the base portion 502i to the extent that it would hamper the ability of the driver 500i to be fully driven to a final firing position. For example, the staple supporting portion 520i and/or the tangs 622i, 626i, 642i, 646i may be fabricated from ULTEM® and the base portion 502i may be fabricated from Nylon with glass or mineral fill to achieve the desired amount of driver compression when encountering the anticipated compression forces during the firing operation. In an alternative version, the tangs 622i, 626i, 642i, 646i may be provided on the base portion 502i and the V-shaped grooves 630i, 650i may be provided in the staple supporting portion 520i.

The various embodiments of the present invention described above and their respective equivalent structures represent vast improvements over prior staple applying assemblies and end effectors. Various embodiments of the present invention provide anvils and/or channels with flexible portions that permit the overall staple height to increase as the compression within the assembly increases due to tissue thickness. Other embodiments employ anvil arrangements that have flexible forming pockets that can be compressed away from the staple cartridge in response to variations in tissue thickness. In doing so, the inherent gap between the forming pocket and the cartridge increases which serves to increase the formed height of the staple. Such advantages can result in improved staple line consistency and provide better clinical outcomes.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. For example, while various manually operated surgical instruments have been depicted for clarity, it should be appreciated that such devices may also be robotically manipulated. In addition, those skilled in the art will appreciate that the embodiments, features and improvements disclosed herein may be readily employed in connection with a variety of other known surgical cutter/staplers, staplers, etc. that may have application in open, laparoscopic, endoscopic and/or intralumenal surgical procedures. In particular, such unique and novel features may be practiced in connection with linear staplers, cutters, contour cutters, etc. Thus, the scope and protection afforded to the various embodiments disclosed herein should not be limited solely to endocutter-type surgical staplers.

While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

The devices disclosed herein can be designed to be disposed of after a single use, or they can be designed to be used multiple times. In either case, however, the device can be reconditioned for reuse after at least one use. Reconditioning can include an combination of the steps of disassembly of the device, followed by cleaning or replacement of particular pieces, and subsequent reassembly. In particular, the device can be disassembled, and any number of particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those of ordinary skill in the art will appreciate that the reconditioning of a device can utilize a variety of different techniques for disassembly, cleaning/replacement, and reassembly. Use of such techniques, and the resulting reconditioned device, are all within the scope of the present application.

Preferably, the invention described herein will be processed before surgery. First a new or used instrument is obtained and, if necessary, cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or higher energy electrons. The radiation kills bacteria on the instrument and in the container. The sterilized instrument can then be stored in the sterile container. The sealed container keeps the instrument sterile until it is opened in the medical facility.

As used herein, the term "fluidically coupled" means that the elements are coupled together with an appropriate line or other means to permit the passage of pressurized gas therebetween. As used herein, the term "line" as used in "supply line" or "return line" refers to an appropriate passage formed from rigid or flexible conduit, pipe, tubing, etc. for transporting fluid from one component to another.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A collapsible staple driver for use in a surgical staple cartridge, said collapsible staple driver comprising:
   a base portion configured to be operably supported by the surgical staple cartridge;
   a staple supporting portion configured to be operably supported within the surgical staple cartridge adjacent to said base portion; and
   at least one attachment member protruding from one of the base portion and the staple supporting portion to be received in a corresponding aperture in the other of the base portion and the staple supporting portion, each said at least one attachment member and the aperture corresponding thereto being configured relative to each other to establish a frictional fit therebetween such that the staple supporting portion in retained in a stationary positive relative to said base portion prior to an application of a compression force thereto and wherein said frictional fit is overcome upon the application of said compression force thereto.

2. The collapsible staple driver of claim 1 wherein each said at least one attachment member has a substantially round cross-sectional shape and the aperture corresponding thereto comprises a round hole.

3. The collapsible staple driver of claim 1 wherein each said at least one attachment member comprises a tapered member.

4. The collapsible staple driver of claim 1 wherein each said at least one attachment member has a shearable portion thereon that is configured to be sheared from at least another portion of said at least one attachment member as said at least one attachment member is driven into the aperture corresponding thereto during the application of the compression forces to said base portion and said staple supporting portion.

5. The collapsible staple driver of claim 1 wherein each said at least one attachment member comprises a rod having a substantially round cross-sectional shape and wherein the aperture corresponding thereto comprises a non-round hole.

6. The collapsible staple driver of claim 1 wherein each said at least one attachment member comprises a tang having tapered surfaces and wherein the aperture corresponding thereto has tapered surfaces similar to the tapered surfaces on said tang.

7. The collapsible staple driver of claim 1 wherein said at least one attachment member comprises at least one pair of tangs corresponding to one said aperture, said tangs of each said pair having ends spaced from each other to establish a frictional fit with said corresponding aperture to support said staple supporting portion in a first position and upon the application of said compression forces to said base portion and said staple supporting portion said end portions move inwardly toward each other to permit said staple supporting portion and said base portion to move toward each other.

8. The collapsible staple driver of claim 7 wherein said corresponding aperture comprises first and second grooves and wherein said at least one pair of tangs comprises:
   a first pair of tangs corresponding to said first groove; and
   a second pair of tangs corresponding to said second groove, said first pair of tangs coacting with said first groove and said second pair of tangs coacting with said second groove to retain said staple supporting portion in said first position prior to the application of the compression forces to said staple supporting portion and said base portion and permitting said staple supporting portion and said base portion to move toward each other upon the application of the compression forces thereto.

9. The collapsible staple driver of claim 1 wherein said staple supporting portion is fabricated from a first material and said base portion is fabricated from a second material that is more rigid than said first material.

10. A surgical stapling instrument, comprising:
   a cartridge supporting assembly for operably supporting a staple cartridge therein;
   a staple cartridge supported within said cartridge supporting assembly and operably supporting a plurality of collapsible staple supporting drivers therein, said staple supporting drivers comprising:
   a base portion movably supported within the staple cartridge;
   a staple supporting portion movably supported within the staple cartridge adjacent to said base portion; and
   at least one attachment member protruding from one of the base portion and the staple supporting portion to be received in a corresponding aperture in the other of the base portion and the staple supporting portion, each said at least one attachment member and the aperture corresponding thereto being configured relative to each other to establish a frictional fit therebetween such that the staple supporting portion is retained in a stationary position relative to said base portion prior to an application of a compression force that is overcome during the staple firing operation;

an anvil coupled to said cartridge supporting assembly and being selectively movable between an open position and a closed position; and a drive member operably supported relative to said cartridge supporting assembly for driving said collapsible staple supporting drivers toward said anvil when said anvil is in said closed position in response to a firing force applied to said drive member.

11. A method for processing an instrument for surgery, said method comprising:

obtaining said surgical instrument of claim 10;

sterilizing said surgical instrument; and storing said instrument in a sterile container.

12. The surgical stapling instrument of claim 10 wherein each said attachment member and said base portion are fabricated from different materials.

13. The surgical stapling instrument of claim 10 wherein said at least one attachment member protrudes from said base portion and said corresponding aperture is in said staple supporting portion.

14. The surgical instrument of claim 10 wherein said at least one attachment member is selected from the group of attachment members consisting of: a rod having a substantially round cross-sectional shape, a tapered rod, a tang having at least two tapered surfaces, and a pair of tangs having ends oriented in spaced relation to each other and being biasable towards each other upon the application of forces thereto.

15. A collapsible staple driver for use in a surgical staple cartridge, said collapsible staple driver comprising:

a base portion configured to be operably supported by the surgical staple cartridge;

a staple supporting portion configured to be operably supported within the surgical staple cartridge adjacent to said base portion; and at least one attachment member protruding from one of the base portion and the staple supporting portion to be received in a corresponding aperture in the other of the base portion and the staple supporting portion, at least one said at least one attachment member having a shearable portion thereon that is configured to be sheared from at least another portion of said at least one attachment member as said at least one attachment member is driven into the aperture corresponding thereto during the application of the compression forces to said base portion and said staple supporting portion.

16. A collapsible staple driver for use in a surgical staple cartridge, said collapsible staple driver comprising:

a base portion configured to be operably supported by the surgical staple cartridge;

a staple supporting portion configured to be operably supported within the surgical staple cartridge adjacent to said base portion; and at least one attachment member protruding from one of the base portion and the staple supporting portion to be received in a corresponding aperture in the other of the base portion and the staple supporting portion, each said at least one attachment member comprising a tang having tapered surfaces and wherein the aperture corresponding thereto has tapered surfaces similar to the tapered surfaces on said tang.

17. A collapsible staple driver for use in a surgical staple cartridge, said collapsible staple driver comprising:

a base portion configured to be operably supported by the surgical staple cartridge;

a staple supporting portion configured to be operably supported within the surgical staple cartridge adjacent to said base portion; and at least one attachment member protruding from one of the base portion and the staple supporting portion to be received in a corresponding aperture in the other of the base portion and the staple supporting portion, each said at least one attachment member comprising at least one pair of tangs corresponding to one said aperture, said tangs of each said pair having ends spaced from each other to establish a frictional fit with said corresponding aperture to support said staple supporting portion in a first position and upon the application of said compression forces to said base portion and said staple supporting portion said end portions move toward each other to permit said staple supporting portion and said base portion to move toward each other.

18. The collapsible staple driver of claim 17 wherein said corresponding aperture comprises first and second grooves and wherein said at least one pair of tangs comprises:

a first pair of tangs corresponding to said first groove; and a second pair of tangs corresponding to said second groove, said first pair of tangs coacting with said first groove and said second pair of tangs coacting with said second groove to retain said staple supporting portion in said first position prior to the application of the compression forces to said staple supporting portion and said base portion and permitting said staple supporting portion and said base portion to move toward each other upon the application of the compression forces thereto.

19. A surgical stapling instrument, comprising:

a cartridge supporting assembly for operably supporting a staple cartridge therein;

a staple cartridge supported within said cartridge supporting assembly and operably supporting a plurality of collapsible staple supporting drivers therein, said staple supporting drivers comprising:

a base portion movably supported within the staple cartridge;

a staple supporting portion movably supported within the staple cartridge adjacent to said base portion; and at least one attachment member protruding from one of the base portion and the staple supporting portion to be received in a corresponding aperture in the other of the base portion and the staple supporting portion, each said at least one attachment member and the aperture corresponding thereto being configured relative to each other to establish frictional fit therebetween that is overcome upon the application of said compression forces during the staple firing operation, said at least one attachment member being selected from the group of attachment members consisting of: a rod having a substantially round cross-sectional shape, a tapered rod, a tang having at least two tapered surfaces, and a pair of tangs having ends oriented in spaced relation to each other and being biasable towards each other upon the application of forces thereto;

an anvil coupled to said cartridge supporting assembly and being selectively movable between an open position and a closed position; and a drive member operably supported relative to said cartridge supporting assembly for driving said collapsible staple supporting drivers toward said anvil when said anvil is in said closed position in response to a firing force applied to said drive member.

20. A method for processing an instrument for surgery, said method comprising:
  obtaining said surgical instrument of claim 19;
  sterilizing said surgical instrument; and
  storing said instrument in a sterile container.

21. The surgical stapling instrument of claim 19 wherein each said attachment member and said base portion are fabricated from different materials.

22. The surgical stapling instrument of claim 19 wherein said at least one attachment member protrudes from said base portion and said corresponding aperture is in said staple supporting portion.

* * * * *